(12) United States Patent
Winter et al.

(10) Patent No.: US 11,324,852 B2
(45) Date of Patent: May 10, 2022

(54) COATED SILK FILMS, METHODS FOR THE PRODUCTION THEREOF AND USES THEREOF

(71) Applicants: AMSILK GMBH, Planegg/Martinsried (DE); LUDWIG-MAXIMILIANS-UNIVERSITAT MUNCHEN, Munich (DE)

(72) Inventors: Gerhard Winter, Penzberg (DE); Elisa Agostini, Munich (DE); Julia Engert, Munich (DE); Lin Romer, Ottobrunn (DE); Ute Slotta, Munich (DE)

(73) Assignee: Amsilk GmbH, Planegg/Martsinried (DE)

( * ) Notice: Subject to any disclaimer, the term of this patent is extended or adjusted under 35 U.S.C. 154(b) by 0 days.

(21) Appl. No.: 15/115,215

(22) PCT Filed: Jan. 29, 2015

(86) PCT No.: PCT/EP2015/051814
§ 371 (c)(1),
(2) Date: Jul. 28, 2016

(87) PCT Pub. No.: WO2015/117888
PCT Pub. Date: Aug. 13, 2015

(65) Prior Publication Data
US 2017/0202995 A1    Jul. 20, 2017

(30) Foreign Application Priority Data
Feb. 4, 2014 (EP) .................................. 14153872

(51) Int. Cl.
| A61L 15/32 | (2006.01) |
| A61K 8/64 | (2006.01) |
| A61L 15/44 | (2006.01) |
| A61Q 19/00 | (2006.01) |
| A61K 8/02 | (2006.01) |
| A61L 15/40 | (2006.01) |
| A61K 9/70 | (2006.01) |
| A61K 8/98 | (2006.01) |

(52) U.S. Cl.
CPC ............ *A61L 15/32* (2013.01); *A61K 8/0208* (2013.01); *A61K 8/64* (2013.01); *A61K 8/987* (2013.01); *A61K 9/7007* (2013.01); *A61L 15/40* (2013.01); *A61L 15/44* (2013.01); *A61Q 19/00* (2013.01); *A61L 2420/02* (2013.01)

(58) Field of Classification Search
None
See application file for complete search history.

(56) References Cited

U.S. PATENT DOCUMENTS

| 2004/0199241 | A1 | 10/2004 | Gravett et al. | |
| 2009/0263430 | A1* | 10/2009 | Scheibel | A61L 27/227 424/400 |
| 2011/0111031 | A1* | 5/2011 | Jiang | A61K 9/0024 424/484 |
| 2012/0095418 | A1* | 4/2012 | Stopek | A61P 35/00 604/304 |

FOREIGN PATENT DOCUMENTS

| WO | 2003-057727 A1 | 7/2003 |
| WO | 2013-119551 A1 | 8/2013 |
| WO | 2013-126799 A1 | 8/2013 |
| WO | 2013-159101 A1 | 10/2013 |

OTHER PUBLICATIONS

Wang et al., "Nanolayer Biomaterial Coatings of Silk Fibroin for Controlled Release," *Journal of Controlled Release*, Elsevier, Amsterdam, NL, vol. 121, No. 3, Aug. 10, 2007, pp. 190-199.
International Search Report in PCT/EP2015/051814, dated Apr. 23, 2015.

* cited by examiner

*Primary Examiner* — Robert A Wax
*Assistant Examiner* — Randeep Singh
(74) *Attorney, Agent, or Firm* — Kilpatrick Townsend & Stockton LLP

(57) ABSTRACT

The present invention relates to coated silk films. Further, the present invention relates to pharmaceutical or cosmetic compositions comprising the coated silk films. Furthermore, the present invention relates to coated silk films or pharmaceutical compositions comprising the coated silk films for use in medicine. In addition, the present invention relates to methods of producing the coated silk films.

10 Claims, 11 Drawing Sheets
Specification includes a Sequence Listing.

A

B

C

D

A

B

C

A

B

COATED SILK FILMS, METHODS FOR THE PRODUCTION THEREOF AND USES THEREOF

The present invention relates to coated silk films. Further, the present invention relates to pharmaceutical or cosmetic compositions comprising the coated silk films. Furthermore, the present invention relates to coated silk films or pharmaceutical compositions comprising the coated silk films for use in medicine. In addition, the present invention relates to methods of producing the coated silk films.

BACKGROUND OF THE INVENTION

In the past years, sophisticated drug depot systems for controlled delivery of drugs have been developed, for example to achieve constant drug levels during therapy. These systems have the advantage of reducing toxic side effects so that the number of drug administrations can be decreased, while at the same time improving cellular uptake and bioavailability. There is also an ongoing quest to design depot systems which facilitate controlled delivery of substances other than pharmaceutical compounds such as cosmetic compounds. In general, the material employed as a carrier for controlled delivery of a substance should offer control of structure, morphology and function, while also exhibiting good mechanical stability. For example, biodegradable and biocompatible polymers are preferred because of their ability to retain their properties for a limited period of time before gradually decomposing into soluble nontoxic degradation products which can be excreted from the body. Many synthetic polymers (e.g. polyester or polyurethane) and biopolymers (e.g. polysaccharides or proteins) have been employed to produce drug depot systems for encapsulation, incorporation, or binding of active compounds. In particular, the use of silk as biopolymer for drug depot systems, especially because of its biocompatibility, non-toxicity and biodegradability, has been investigated in the art. For example, silk films have been tested for their ability to deliver drugs and other substances. Especially, silk derived from spiders or insects has been used.

The inventors of the present invention studied silk films as drug release systems. Without wishing to be bound to any theory, they surprisingly found that drugs released faster through the side surfaces than through the upper and lower surfaces of silk films, thus, resulting in a(n) (initial) burst drug release profile. However, in many applications it is desirable to release the loaded drug over an extended period of time controllably, constantly, and sustainably. The inventors of the present invention surprisingly found that a controlled, constant, and sustained drug release profile can be achieved with silk films which comprise at least at their side surfaces a coating layer in order to reduce the rapid diffusion of compounds through said side surfaces. The favourable release profile of the coated silk films renders them eminently suitable for controlled, constant, and sustained delivery of pharmaceutical as well as cosmetic compounds. The compounds can be small molecular weight compounds such as drugs and/or proteins. Due to their stability and biocompatibility under physiological conditions, the coated silk films are especially suitable for in vivo applications. The casting of silk films from an aqueous solution avoids the use of organic solvents.

SUMMARY OF THE INVENTION

In a first aspect, the present invention relates to a coated silk film comprising
(i) an active agent release sheet which comprises one or more first silk film layers comprising at least one active agent, and
(ii) one or more release modifying layers covering at least the side surface(s) of the active agent release sheet.

In a second aspect, the present invention relates to a pharmaceutical composition comprising the coated silk film according to the first aspect, wherein the active agent is a pharmaceutical agent.

In a third aspect, the present invention relates to a cosmetic composition comprising the coated silk film according to the first aspect, wherein the active agent is a cosmetic agent.

In a fourth aspect, the present invention relates to a coated silk film according to the first aspect or pharmaceutical composition according to the second aspect for use in medicine.

In a fifth aspect, the present invention relates to a coated silk film according to the first aspect or pharmaceutical composition according to the second aspect for controlled and sustained release of at least one pharmaceutical agent.

In a sixth aspect, the present invention relates to a coated silk film according to the first aspect or pharmaceutical composition according to the second aspect for the treatment of wounds, skin diseases, or skin defects.

In a seventh aspect, the present invention relates to the use of the coated silk film according to the first aspect or cosmetic composition according to the third aspect for controlled and sustained release of at least one cosmetic agent.

In an eight aspect, the present invention relates to a method of producing a coated silk film comprising the steps of:
(i) providing an active agent release sheet which comprises one or more first silk film layers comprising at least one active agent, and
(ii) covering at least the side surface(s) of the active agent release sheet with one or more release modifying layers.

The following figures are merely illustrative of the present invention and should not be construed to limit the scope of the invention as indicated by the appended claims in any way.

DETAILED DESCRIPTION OF THE INVENTION

Figure 1:
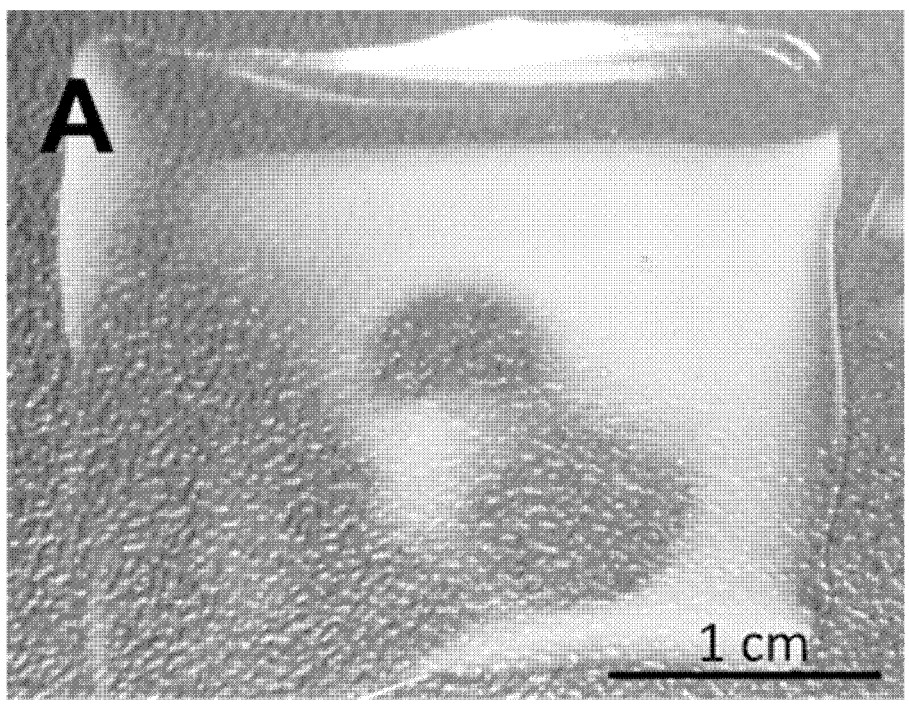
FIG. 1: Shows in (A) a photograph of a spider silk film comprising $C_{16}$ after casting from an aqueous solution using a digital camera (DSC-575, Sony Corporation, Tokyo, Japan) (scale bar=1 cm) and in (B) a photograph of a spider silk film comprising $C_{16}$ after casting from an aqueous solution with a film applicator using a digital camera (DSC-575, Sony Corporation, Tokyo, Japan) (scale bar=1 cm). In particular, the spider silk film comprising $C_{16}$ was cast on the plastic foil A5 22/5B from mtv-messtechnik (Koeln, Germany) at room temperature using the film applicator Coatmaster 510 (Erichsen, Hemer, Germany) having a casting knife of 2000 μm and with a velocity of 1 mm/sec.
Figure 1:
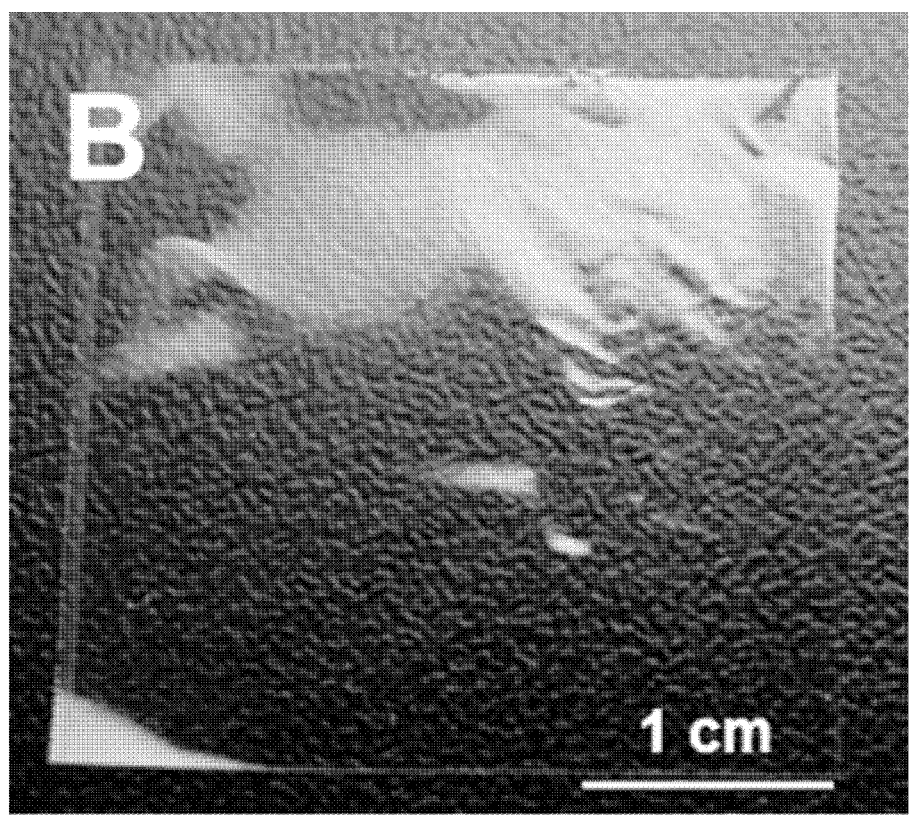

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment the coated silk film of the present invention comprises at least one pharmaceutical active agent and if in another preferred embodiment the one or more first silk film layer of the coated silk film comprise at least one silk polypeptide, it is a contemplated preferred embodiment that the coated silk film of the present invention comprises at least one pharmaceutical active agent and one or more first silk film layers comprising at least one silk polypeptide.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, definitions will be provided which apply to all aspects of the present invention.

Residues in two or more polypeptides are said to "correspond" to each other if the residues occupy an analogous position in the polypeptide structures. It is well known in the art that analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS: needle, Matrix: Blosum62, Gap Open 10.0, Gap Extend 0.5.

Unless otherwise indicated, the terms "polypeptide" and "protein" are used interchangeably herein and mean any peptide-linked chain of amino acids, regardless of length or post-translational modification.

The term "silk film", as described herein, refers to a self-supporting object. A self-supporting object is an object which has the capacity for supporting itself without the help of additional materials such as carrier elements. A silk film being self-supporting preferably has a thickness of at least 0.1 µm.

The term "silk film", as described herein, also refers to an object having a first surface and a second surface which are opposed to each other and having at least one connecting side surface. The first surface may also be designated as top surface and the second surface may also be designated as base surface. In one embodiment, the surface area of the first surface and second surface is larger than the surface area of the side surface(s). For example, the first and second surface area is at least 10 fold larger than the surface area of the side surface(s). The silk film may have the form of a pancake cylinder having a first surface and a second surface which are opposed to each other and a connecting side surface. The silk film may also have a flat rectangular block shape having a first surface and a second surface which are opposed to each other and connecting side surfaces. The first and second surfaces preferably have the same shape and/or dimension.

The term "coated silk film", as used herein, refers to a silk film which additionally comprises (a) release modifying layer(s) covering at least the side surface(s) of the silk film. In one embodiment, the modifying layer(s) completely cover(s) the silk film. The modifying layer(s) is (are) not necessarily self-supporting, but can be self-supporting. The release modifying layer preferably has a thickness of at least 0.05 µm, e.g. of at least 0.1 µm.

The term "coated silk film", as used herein, also refers to a silk film comprising or consisting of an active agent release sheet.

The term "active agent release sheet", as used herein, refers to a sheet comprising (an) active agent(s). The active agent release sheet is loaded with said active agent(s). In other words, the active agent(s) is (are) incorporated into and/or attached to the active agent release sheet. The active agent release sheet is designed to release the active agent(s) comprised therein, e.g. into a physiological environment.

Preferably, said release is a controlled, constant, and/or sustained release. In particular, the active agent release sheet is designed to release the active agent(s) at a predetermined rate in order to maintain a constant active agent concentration for a specific period of time with minimum side effects.

The term "active agent release sheet", as used herein, also refers to an object having a first surface and a second surface which are opposed to each other and having at least one connecting side surface. The first surface may also be designated as top surface and the second surface may also be designated as base surface. In one embodiment, the surface area of the first surface and second surface is larger than the surface area of the side surface(s). For example, the first and second surface area is at least 10 fold larger than the surface area of the side surface(s).

More precisely, the term "active agent release sheet", as used herein, refers to a sheet which comprises (a) first silk film layer(s) comprising (an) active agent(s). Said first silk film layer(s) is (are) loaded with said active agent(s) or the active agent(s) is (are) incorporated into and/or attached to the first silk film layer(s). The active agent release sheet can have a monolayered or multilayered form. In its monolayered form, the active agent release sheet comprises or consists of a first silk film layer comprising (an) active agent(s). In its multilayered form, the active agent release sheet comprises or consists of first silk film layers comprising (an) active agent(s), or (a) first silk film layer(s) comprising (an) active agent(s) and (a) second silk film layer(s). The active agent release sheet preferably has a thickness of at least 0.1 μm.

The term "first silk film layer", as used herein, refers to a film layer comprising or consisting of silk and (an) active agent(s). The term "second silk film layer", as used herein, refers to a film layer comprising or consisting of silk. Thus, the second silk film layer is a layer which does not comprise (an) active agent(s). In other words, the second silk film layer is active agent free. The first silk film layer preferably has a thickness of at least 0.1 μm. In addition, the second silk film layer preferably has a thickness of at least 0.1 μm.

The (coated) silk film, particularly the one or more first silk film layers and/or the one or more second silk film layers, comprise a silk material (e.g. a silk polypeptide).

In the coated silk film, the active agent release sheet is at least at its side surface(s) covered by (a) modifying layer(s). In one embodiment, the modifying layer(s) completely cover(s) the active agent release sheet.

In its broadest sense, the term "coated silk film", as used herein, refers to a silk film which comprises an active agent release sheet consisting of a first silk film layer comprising at least one active agent. Said release sheet is at least at its side surface(s) covered by a release modifying layer.

The term "release modifying layer", as used herein, refers to a layer which is designed to modify or modulate, preferably to reduce or delay, the release, e.g. by diffusion, of the active agent(s) from the side surface(s) of the silk film, particularly of the active agent release sheet, as compared to a silk film, particularly an active agent release sheet, lacking such a release modifying layer. In one embodiment, the release modifying layer completely covers the silk film, particularly the active agent release sheet, and, thus, modifies or modulates, preferably reduces or delays, the release, e.g. by diffusion, of the active agent(s) from any surface of the silk film, particularly of the active agent release sheet, as compared to a silk film, particularly an active agent release sheet, lacking such a release modifying layer. For example, the release modifying layer(s) modify/modifies or modulate(s), preferably reduce(s) or delay(s), the release of the active agent(s) from the side surface(s) of the silk film, particularly of the active agent release sheet, by at least 5, 10, 15, 20, 30, 40, 50, 60, 70, 80, 90, 95, 99, or even 100% compared to a silk film, particularly an active agent release sheet, lacking such a release modifying layer. The release modifying layer preferably has a thickness of at least 0.05 μm, e.g. of at least 0.1 μm. The release modifying layer comprises or consists of a release modifying material (e.g. a silk material such as a silk polypeptide).

The term "release modifying agent", as used herein, refers to an agent which is able to modify or modulate, preferably to reduce or delay, the release, e.g. by diffusion, of (an) active agent(s). Being comprised in the "release modifying layer" or forming the "release modifying layer", the release modifying agent particularly modifies or modulates, preferably reduces or delays, the release of (an) active agent(s) from the side surface(s) of the silk film, particularly of the active agent release sheet. If the release modifying layer completely covers the silk film, particularly the active agent release sheet, the release modifying agent particularly modifies or modulates, preferably reduces or delays, the release of (an) active agent(s) from any surface of the silk film, particularly of the active agent release sheet.

In the context of the present invention, the term "coating" refers to a covering that is applied to the silk film, particularly to the active agent release sheet, to be coated. Said coating covers or surrounds at least the side surface(s) of the silk film, particularly of the active agent release sheet. In one embodiment, said "coating" completely covers or surrounds the silk film, particularly the active agent release sheet. The coating preferably has a thickness of at least 0.05 μm, e.g. of at least 0.1 μm. In particular, the coating of the silk film is achieved with the release modifying layer(s) as described herein.

The term "completely covering", as used herein, means that the silk film, particularly the active agent release sheet, is covered with a continuous coating. Said covering may be evenly or unevenly, preferably evenly.

The term "active agent (also designated as active compound)", as used herein, relates to any substance having an activity when administered to an individual. Said substance may have a biological, pharmaceutical, or cosmetical activity when administered to an individual. A pharmaceutical agent may be any agent with therapeutic, diagnostic, or prophylactic effects, i.e. any therapeutic agent, diagnostic agent, or prophylactic agent. The term "active agent", as used herein, further relates to any substance which is capable of being released from the silk film, particularly the active agent release sheet. It is preferred that the active agent is capable of being released upon exposure of the silk film to physiological conditions, i.e. introducing the silk film, into a buffer or an aqueous solution. It is further preferred that the silk film shows a controlled, constant, and/or sustained release of the loaded active agent. The active agent may be comprised in the silk film, particularly in the active agent release sheet, in form of a particle, such as a nano-particle or micro-particle, or an aggregate.

The term "release", as used herein, refers to the release of (an) active agent(s) from the silk film, particularly from the active agent release sheet, over a period of time.

The term "sustained (or controlled) release" as used herein" refers to the gradual release of (an) active agent(s) from the silk film, particularly from the active agent release sheet, over a period of time. It is preferred that the release displays relatively linear kinetics, thereby providing a constant supply of the active agent over the release period. The release period may vary from several hours to several months depending upon the properties of the active agent(s) and its (their) intended use. For example, it can be desirable that the cumulative release of a pharmaceutical agent from the silk film over a certain treatment period be relatively high to avoid the need for excessive loading of the silk film and consequent waste of unreleased pharmaceutical agent. The active agent(s) is (are) released into a surrounding environment. The surrounding environment may be a physiological environment or a non-physiological environment. The physiological environment (e.g. the physiological medium) may be a physiological buffered solution or a body fluid, e.g. blood, lymph or liquor. The physiological environment may also be an organ (e.g. skin) or a part of an organ (e.g. tissue). The non-physiological environment (e.g. the non-physiological medium) may be an aqueous solution such as water or a buffered aqueous solution, an alcoholic solution, or an organic solution. It should be further noted that the active agent(s) can be released into a surrounding intracorporeal or extracorporeal environment.

The term "physiological environment", as used herein, refers, without limitation, to an environment characterized by a temperature of 37° C. and an atmospheric pressure of 1 bar (100 kPa). It further refers, without limitation, to an environment characterized by a temperature of 37° C., an atmospheric pressure of 1 bar (100 kPa), and a pH of between 4 and 8, particularly a pH of between 6 and 8. Blood as physiological environment has usually, for example, a pH of between 7.37 and 7.44, e.g. a pH of 7.40. Skin as physiological environment has usually, for example, a pH of between 4 and 6.5, e.g. a pH of 5.5.

As mentioned above, the inventors of the present invention studied silk films as drug release systems. Without wishing to be bound to any theory, they surprisingly found that drugs released faster through the side surfaces than through the upper and lower surfaces of silk films, thus, resulting in a(n) (initial) burst drug release profile. However, in many applications it is desirable to release the loaded drug over an extended period of time controllably, constantly, and sustainably. The inventors of the present invention surprisingly found that a controlled, constant, and sustained drug release profile can be achieved with silk films which comprise at least at their side surfaces a coating layer in order to reduce the rapid diffusion of compounds through said side surfaces. The favourable release profile of the coated silk films renders them eminently suitable for controlled, constant, and sustained delivery of pharmaceutical as well as cosmetic compounds. Due to their stability and biocompatibility under physiological conditions, the coated silk films are especially suitable for in vivo applications.

Thus, in a first aspect, the present invention relates to a coated silk film comprising or consisting of
(i) an active agent release sheet which comprises or consists of one or more first silk film layers comprising at least one active agent, and
(ii) one or more release modifying layers covering at least the side surface(s) of the active agent release sheet.

The coated silk film may comprise an active agent release sheet comprising 1, 2, 3, or more first silk film layers. Alternatively or additionally, the coated silk film may comprise 1, 2, 3, 4, 5, or more release modifying layers.

In one embodiment, the one or more release modifying layers completely cover the active agent release sheet. Thus, the coated silk film may comprise or consist of
(i) an active agent release sheet which comprises or consists of one or more first silk film layers comprising at least one active agent, and
(ii) one or more release modifying layers completely covering the active agent release sheet.

As mentioned above, the active agent release sheet may comprise two or more first silk film layers. Each first silk film layer of the active agent release sheet may comprise the same or (a) different active agent(s). The incorporation of different active agents in the first silk film layers of the active agent release sheet allows the modification of the release profile and the control of the interaction between different active agents. For example, if two active agents cannot be incorporated together in the same first silk film layer due to the negative interaction between said active agents, each active agent can be loaded in a different first silk film layer.

In one another embodiment, the active agent release sheet comprises one or more second silk film layers. Thus, the coated silk film may comprise or consist of
(i) an active agent release sheet which comprises or consists of one or more first silk film layers comprising at least one active agent and one or more second silk film layers, and
(ii) one or more release modifying layers covering at least the side surface(s) of the active agent release sheet.

The coated silk film may comprise an active agent release sheet comprising 1, 2, 3, or more first silk film layers and/or 1, 2, 3, 4, 5, 6, 7, 8, 9, 10, 11, 12, or more second silk film layers. Alternatively or additionally, the coated silk film may comprise 1, 2, 3, 4, 5, or more release modifying layers.

As mentioned above, in one embodiment, the one or more release modifying layers completely cover the active agent release sheet. Thus, the coated silk film may comprise or consist of
(i) an active agent release sheet which comprises or consists of one or more first silk film layers comprising at least one active agent and one or more second silk film layers, and
(ii) one or more release modifying layers completely covering the active agent release sheet.

In one preferred embodiment, the active agent release sheet comprises or consists of (a) first silk film layer(s) comprising at least one active agent which is (are) flanked by second silk film layers. In other word, the first silk film layer(s) comprising at least one active agent is (are) sandwiched or embedded between second silk film layers. The inventors of the present invention found that the number of second silk film layers flanking the first silk film layer(s) has an influence on the release of the active agent comprised therein. Thus, an increase of the number of second silk film layers flanking the first silk film layer(s) reduces the release of the active agent comprised therein. Thus, the variation of the number of second silk film layers flanking the first silk film layer(s) allows to adapt/change the release profile of the active agents comprised therein.

In one another preferred embodiment, the one or more first silk film layers and/or the one or more second silk film layers comprise at least one plasticizer. The inventors of the present invention found that the mechanical properties, e.g. the elasticity and/or flexibility, of the silk film can be improved using plasticizers. For example, the use of plasticizers, improves, particularly increases, the film elongation. Further, the inventors of the present invention found that the presence of plasticizers in the first silk film layers or in the first and second silk film layers improves the connection of the first silk film layers or of the first and second silk film layers with each other, or the coherence of the first silk film layers or of the first and second silk film layers to each other. Furthermore, the inventors of the present invention found that the presence of plasticizers in the silk film, particularly in the active agent release sheet, influences the release of active agents from the silk film, particularly from the active agent release sheet. In particular, the presence of plasticizers modifies or modulates, preferably increases or decreases, the release of active agents. For example, the presence of plasticizers such as glycerol increases the release of active agents, while the presence of plasticizers such as 2-pyrrolidone decreases the release of active agents. Thus, the presence of plasticizers in the first and/or second silk film layer(s) of the active agent release sheet of the silk film or not and, if yes, the variation of the amount of plasticizers in the first and/or second silk film layer(s) of the active agent release sheet of the silk film allows to adapt/change the release profile of the active agents comprised therein.

Figure 4:
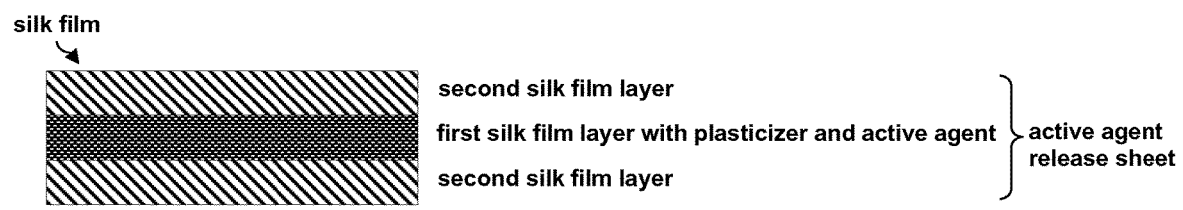
FIG. 4: Shows in (A) a schematic cross-sectional drawing of a silk film comprising an active agent release sheet which comprises one first silk film layer comprising an active agent and two second silk film layers (i.e. 3-layer silk film). (B) Cross section of a $C_{16}$ film schematically shown as silk film in (A) comprising an active agent release sheet which comprises one first $C_{16}$ film layer comprising an active agent and two second $C_{16}$ film layers (Digital Microscope Keyence VHX-500F) (i.e. 3-layer $C_{16}$ film). Scale bar: 50 μm. (C) Schematic drawing of a coated silk film of the present invention comprising an active agent release sheet which comprises one first silk film layer comprising an active agent and two second silk film layers, and one release modifying silk layer completely covering the active agent release sheet (i.e. 4-layer silk film). (D) Cross section of a coated $C_{16}$ film schematically shown in (C) comprising an active agent release sheet which comprises one first $C_{16}$ film layer comprising an active agent and two second $C_{16}$ film layers, and one release modifying $C_{16}$ film layer completely covering the active agent release sheet (i.e. 4-layer $C_{16}$ film). Scale bar: 250 μm.
Figure 4:
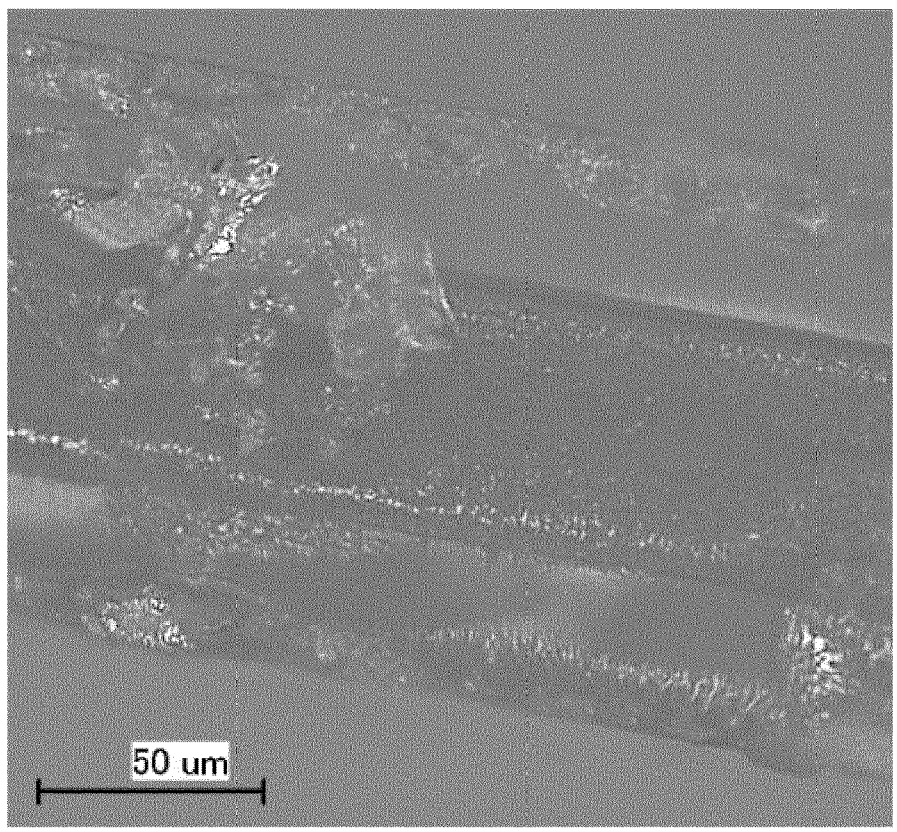
Figure 4:
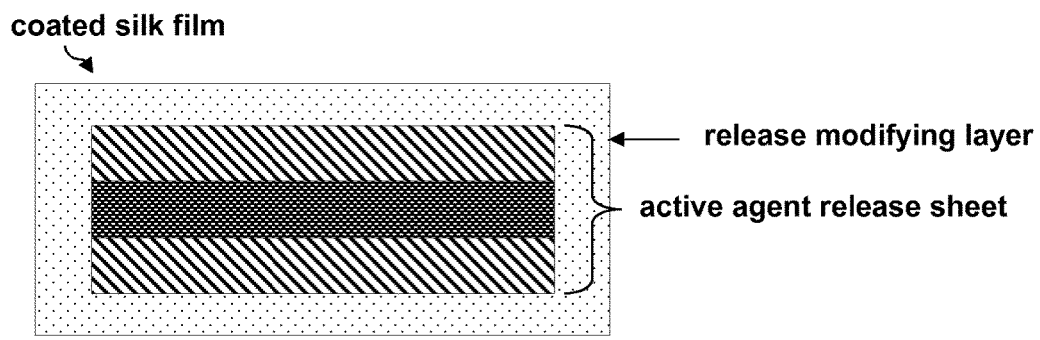
Figure 4:
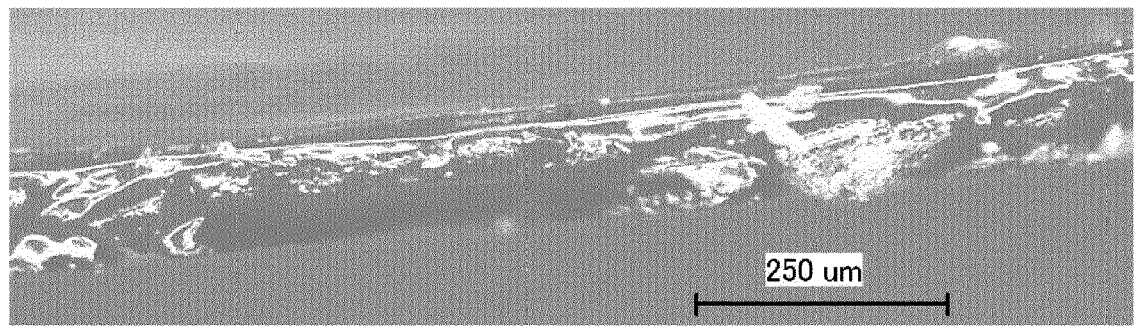
Figure 5:
FIG. 5: Shows in (A) a schematic cross-sectional drawing of a silk film comprising an active agent release sheet which comprises one first silk film layer comprising an active agent and six second silk film layers, wherein plasticizer containing second silk film layers and plasticizer free second silk film layers are arranged in alteration (i.e. 7-layer silk film). (B) Cross section of a $C_{16}$ film schematically shown as silk film in (A) comprising an active agent release sheet which comprises one first $C_{16}$ film layer comprising an active agent and six second $C_{16}$ film layers, wherein glycerol containing second $C_{16}$ film layers and glycerol free second $C_{16}$ film layers are arranged in alteration (Digital Microscope Keyence VHX-500F) (i.e. 7-layer $C_{16}$ film). Scale bar: 250 μm. (C) Schematic drawing of a coated silk film of the present invention comprising an active agent release sheet which comprises one first silk film layer comprising an active agent and six second silk film layers, wherein plasticizer containing second silk film layers and plasticizer free second silk film layers are arranged in alteration and one release modifying silk layer completely covering the active agent release sheet (i.e. 8-layer silk film).
Figure 5:
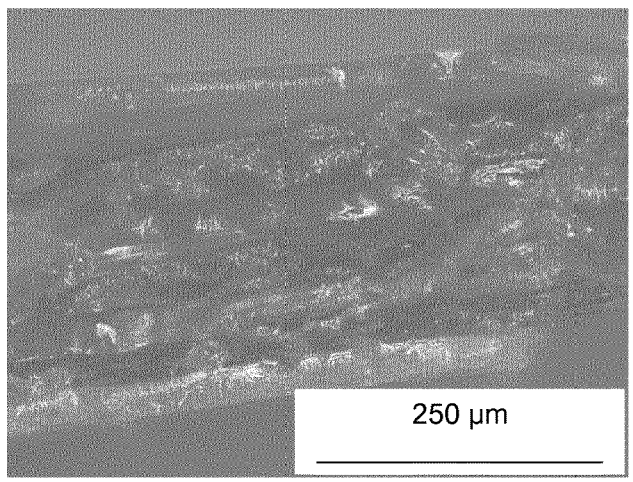
Figure 5:
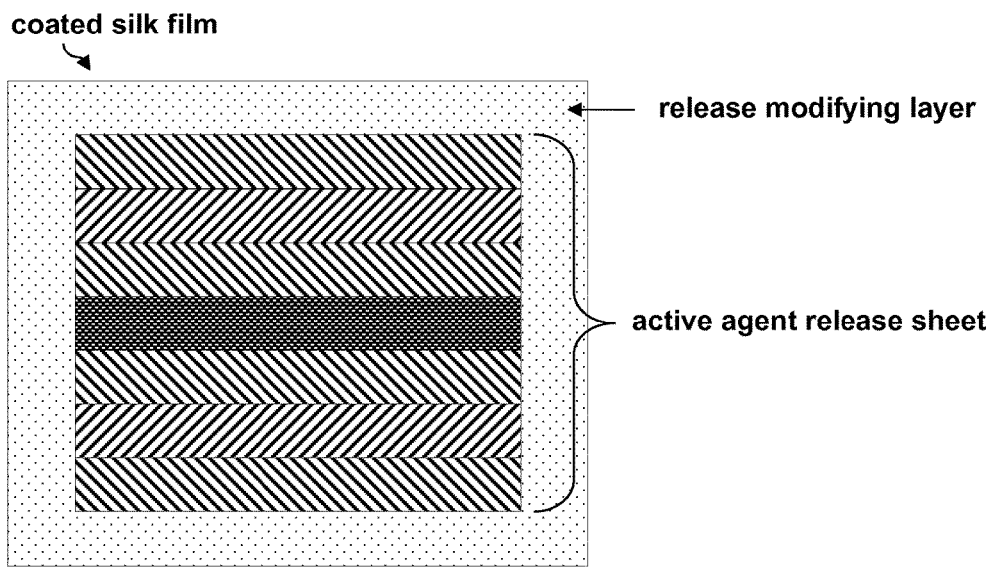

In one further preferred embodiment, the active agent release sheet comprises plasticizer containing first and/or second silk film layers and plasticizer free first and/or second silk film layers in alteration. For example, the active agent release sheet may comprise one plasticizer containing first silk film layer and one plasticizer free second silk film layer. Further, the active agent release sheet may comprise one plasticizer containing first silk film layer and two plasticizer free second silk film layers, wherein both plasticizer free second silk film layers are attached to the plasticizer containing first silk film layer, thereby forming a sandwich structure. Furthermore, the active agent release sheet may comprise one plasticizer containing first silk film layer, one or more plasticizer containing second silk film layers and one or more plasticizer free second silk film layers, wherein the plasticizer containing silk film layers and plasticizer free silk film layers are arranged alternately. The active agent release sheet may have a structure as described in FIGS. 4A and 4B, and FIGS. 5A and 5B. The coated silk film may have a structure as described in FIGS. 4C and 4D and FIG. 5C.

In one embodiment, the one or more release modifying layers do not contain a plasticizer. In other words, in one embodiment, the one or more release modifying layers are plasticizer free. In one preferred embodiment, the one or more release modifying layers do not contain a plasticizer which increases the release of active agents. As mentioned above, the presence of plasticizers such as glycerol may increase the release of active agents. The release modifying layers may, however, be layers which are designed to reduce or delay/sustain the release of active agents at least at the side surface(s) of the active agent release sheet. In this case, the presence of plasticizers which increase the release of active agents in said release modifying layer(s) is not preferred. In another preferred embodiment, the one or more release modifying layers contain a plasticizer which decreases the release of active agents. As mentioned above, the presence of plasticizers such as 2-pyrrolidone may decrease the release of active agents. The release modifying layers may also be layers which are designed to reduce or delay/sustain the release of active agents at least at the side surface(s) of the active agent release sheet. In this case, the presence of plasticizers which decrease the release of active agents in said release modifying layer(s) is preferred.

It is preferred that the amount of the plasticizer in the one or more first silk film layers and/or one or more second silk film layers is of between 0.1% (w/w) and 70% (w/w), more preferably of between 5% (w/w) and 70% (w/w) or of between 15% (w/w) and 70% (w/w), even more preferably of between 15% (w/w) and 55% (w/w) or of between 30% (w/w) and 55% (w/w), and most preferably of 30% (w/w). It is further preferred that the amount of the plasticizer in the one or more first silk film layers and/or one or more second silk film layers is of at least 0.1, 1, 5, 10, 15, 20, 25, 30, 35, 40, 45, 50, 55, 60, 65, or 70% (w/w).

Preferred plasticizers are selected from glycerol, 2-pyrrolidone, polyethylenglycol (PEG), polyvinylalcohol (PVA), poloxamer, polyvinylpirrolidone (PVP), polyacrylic acid, polyorthoester, gelatine, collagen, cellulose, cellulose derivates, and sorbitol. More preferred plasticizers are selected from glycerol and 2-pyrrolidone.

It is further preferred that the active agent has a molecular weight of between 50 Da and 300 kDa, preferably of between 80 Da and 250 kDa, more preferably of between 100 Da and 200 kDa, and most preferably of between 150 Da and 150 kDa. The active agent may further have a molecular weight of between 50 Da and <50 kDa or a molecular weight of between 50 kDa and 150 kDa. The inventors of the present invention found that the release rate of active agents depends on their molecular weight. In particular, they found that the higher the molecular weight of the active agents, the slower is their release. For example, active agents having a molecular weight of between 50 kDa and 150 kDa are released slower from the silk film, particularly from the active agent release sheet, compared to active agents having a molecular weight of between 50 Da and <50 kDa.

Preferred active agents are selected from the group consisting of a biological agent, a pharmaceutical agent, a cosmetic agent, a nutrient, and a dietary supplement.

The term "biological agent (also designated as biological material)", as used herein, relates to any substance or material having a biological origin. For example, the term "biological agent" covers cells (including stem cells), proteins, peptides, or nucleic acids (DNA or RNA such as mRNA, miRNA, or siRNA).

The term "pharmaceutical agent (also designated as pharmaceutical compound)", as used herein, refers to any biological or chemical substance, particularly pharmacological, metabolic, or immunological substance, which may be used in the treatment, cure, prophylaxis, prevention, or diagnosis of a pathological condition, e.g. a disease or disorder, or which may be used to otherwise enhance the physical, psychical, or mental well-being. Accordingly, the term "pharmaceutical agent" envisaged in the context of the present invention includes any agent with therapeutic, diagnostic, or prophylactic effects, i.e. any therapeutic agent, diagnostic agent, or prophylactic agent.

The pharmaceutical agent may be an agent that affects or participates in tissue growth, cell growth, cell differentiation, an agent that is able to invoke a biological action such as an immune response, or an agent that can play any other role in one or more biological processes. Preferably, the pharmaceutical agent is selected from the group consisting of an anti-microbial agent, such as an antibacterial agent (e.g. an antibiotic), an anti-viral agent or an anti-fungal agent, an immunosuppressive agent, an anti-inflammatory agent, an anti-allergic agent, an anti-coagulant, an anti-rheumatic agent, an anti-psoriatic agent, a sedative agent, a muscle relaxant, an anti-migraine agent, an anti-depressant, an insect repellent, a growth factor, a hormone, a hormone antagonist, an antibody, an adjuvant, e.g. in combination with an immunological active compound such as an antibody, an antioxidant, a protein, such as a glycoprotein, lipoprotein, or an enzyme (e.g. hyaluronidases), a polysaccharide, a free radical scavenger, a radio-therapeutic agent, a photodynamic therapy agent, a dye such as a fluorescent dye, a contrast agent, a disinfectant, a preservative, a vitamin, a tissue substituent, and a blood substituent. The pharmaceutical agent may also be a small molecule compound. The term "small molecule compound" refers to a molecule that can act to affect biological processes. Small molecules can include any number of therapeutic agents presently known and used, or can be small molecules synthesized in a library of such molecules for the purpose of screening for biological function(s). The small molecule compound usually have a molecular weight less than about 5,000 daltons (Da), preferably less than about 2,500 Da, more preferably less than 1,000 Da, most preferably less than about 500 Da. The small molecule compound preferably serves as regulating molecule of biological processes such as an enzyme substrate, an antagonist, or an allosterically activating or an allosterically inhibiting molecule. It is preferred, that the molecule is capable of binding to another molecule, such as a protein, nucleic acid or polysaccharide, and acting as an effector, altering the activity of the other molecule.

The term "cosmetic agent (also designated as cosmetic compound)", as used herein, refers to a substance intended mainly for external use on the body surface of an individual. The body surface includes skin, hair, nails, and related muscle and glands. In particular, it is meant that a cosmetic substance is a molecule which shows a certain predictable effect. Such an effect molecule can be, for example, a proteinaceous molecule (e.g. an enzyme) or a non-proteinaceous molecule (e.g. a dye, pigment, photo-protective agent, vitamin, provitamin, an antioxidant, conditioner, or a compound comprising metal ions).

Among the proteinaceous molecules, enzymes are preferred. Examples for useful enzymes include, but are not limited to, oxidases, peroxidases, proteases, glucanases, mutanases, tyrosinases, metal-binding enzymes, lactoperoxidases, lysozymes, aminoglycosidases, glucose oxidases, super oxide dismutases, photolyases, proteins binding heavy metals, T4 endonucleases, catalases, and reductases such as thioredoxin-reductases. Also preferred are proteinaceous substances which do not possess an enzymatic function. Examples for non-enzymatic proteinaceous molecules include, but are not limited to, antimicrobial peptides, hydrophobins, collagens, keratins, proteins binding heavy metals, proteins binding odorants, proteins binding cellulose, proteins binding starch, and proteins binding keratin. Other preferred proteinaceous molecules are, for example, protein hydrolysates, e.g. protein hydrolysates of plant or animal sources. Among the non-proteinaceous molecules, UV-protective agents, antioxidants, vitamins, provitamins and their precursors and derivatives, dyes, polysaccharides, or fragrances are preferred. A UV-protective agent is an organic substance which can absorb specific wavelengths in the range of UV-wavelengths. The absorbed energy can then be emitted in form of longer wave radiation, e.g. heat. An antioxidant is a compound that interrupts the photochemical reaction chain triggered by UV radiation when penetrating into the skin. Typical examples of antioxidants include, but are not limited to, super oxide dismutase, catalase, tocopherol (vitamin E), ascorbic acid (vitamin C), coenzyme Q10 (ubiquinane), and quinione. Examples of vitamins, provitamins and their precursors include, but are not limited to, β-carotene (provitamin of vitamin A), ascorbic acid (vitamin C), tocopherol (vitamin E), the vitamins, provitamins and their precursors of the vitamin B group encompassing vitamin $B_1$ (thiamine), vitamin $B_2$ (riboflavin), vitamin $B_3$ (nicotinic acid or nicotinamid), vitamin $B_5$ (panthothenic acid and panthenol), vitamin $B_6$ (5-hydroxymethyl-2-methylpyridin-3-ol, also known as pyridoxine, pyridoasamine or pyridoxal) and vitamin $B_7$ (biotin). Examples of dyes include, but are not limited to, food dyes, semi-permanent dyes, permanent dyes, reactive dyes, and oxidation dyes. Useful dyes are for example described in Rowe Colour Index, $3^{rd}$ edition, Society of Dyers and Colourists, Bradford, England, 1971. In addition, the cosmetic agent may be a protein, particularly a glycoprotein or lipoprotein, a dye, a fragrance, an infrared-reflective compound, an infrared-absorbent compound, argan oil, hyaluronic acid, sea silt extract, gelee royale, gold extract, medihoney, sacha inchi-oil, or allatonin.

As used herein, a "nutrient" is a chemical that an organism needs to live and grow or a substance used in an organism's metabolism which must be taken in from its environment. Organic nutrients include carbohydrates, fats, proteins (amino acids), and vitamins. Inorganic nutrients are dietary minerals, water, and oxygen. Preferred nutrients are macronutrients such as carbohydrates, amino acids or proteins and micronutrients such as vitamins.

Examples of useful carbohydrates include, but are not limited to, monosaccharides such as, glyceraldehyde, erythrose, threose, ribose, arabinose, xylose, lyxose, allose, altrose, glucose, mannose, gulose, idose, galactose, talose, dihydroxyacetone, erythrulose, ribulose, xylulose, psicose, fructose, sorbose, tagatose or stereoisomers thereof, amino sugars such as galactosamine, glucosamine, sialic acid, N-acetylglucosamine, sulfo sugars such as sulfoquinovose, disaccharides such as sucrose, lactulose, lactose, maltose, trehalose or maltobiose, and oligosacharides such as Fructooligosaccharides (FOS), Galactooligosaccharides (GOS) or Mannan-oligosaccharides (MOS).

The term "dietary supplement (also designated as food supplement or nutritional supplement)", as used herein, refers to a preparation intended to provide nutrients such as vitamins, minerals, fiber, fatty acids or amino acids, that are missing or are not consumed in sufficient quantity in a person's diet. Depending on the country dietary supplements are either defined as foods or as drugs.

Examples of other dietary supplements include, but are not limited to, steroids such as dehydroepiandrosterone (DHEA), pregnenolone, or derivatives thereof, hormones such as melatonin, and other substances such as hydrazine sulfate, caffeine (1,3,7-trimethylxanthine), catechins, soy isoflavones, glucosamine, coenzyme-Q10, or ephedrine-type alkaloids such as ephedrine, synephrine, norephedrine, or pseudoephedrine.

The term "dye", as used herein, refers to a coloured substance having affinity to a substrate to which it is being applied. Dyes are generally applied in aqueous solution. In contrast, pigments are typically insoluble and possess no affinity to the substrate. Both dyes and pigments appear to be coloured because of their ability to absorb specific wavelength of light. The dye can be a naturally occurring or synthetic organic dye or a food dye.

The active agent may be positively or negatively charged. The active agent may also be electroneutral. Preferably, the active agent is positively or negatively charged. The terms "positive charge" and "cationic" as well as "negative charge" and "anionic" can be used interchangeably. As will be shown in detail in the examples, especially positively and negatively charged active agents are well-suited for the remote loading of silk films. For direct loading, the active agent is preferably electroneutral or has the same charge as the silk film. As used herein, "positive charge" means that the active agent possesses at least one elementary charge of a proton and "negative charge" means that the active agent possesses at least one elementary charge of an electron.

The skilled person knows that the charge of an active agent is dependent on factors such as the $pK_a$-value of the active agent and the pH of the aqueous solvent. As used herein, the term "$pK_a$-value", (also known as acidity constant, or acid-ionization constant) is a quantitative measure of the strength of an acid in solution. It is derived from the dissociation constant $K_a$ which describes the equilibrium for a chemical reaction known as dissociation in the context of an acid-base reaction. Due to the many orders of magnitude spanned by $K_a$ values, a logarithmic measure of the acid dissociation constant is more commonly used in practice. The larger the value $pK_a$ the smaller the extent of dissociation and the less strong is an acid. Accordingly, the $pK_b$ value describes the strength of a base in solution.

In aqueous solutions the $pK_a$-value may give an indication whether an active agent has a positive charge or not, thus, having, for example, a negative charge. Preferably, the active agent is positively or negatively charged at the pH used for film formation.

Various other methods for determining or measuring the charge of a compound are known to one of skill in the art. For example, the charge can typically be measured using electrophoretic methods. The charge of a molecule in aqueous solution may also be predicted using suitable software such as ACD/ChemSketch (available at Advanced Chemistry Development, ACD/labs, http://www.acdlabs.com).

The person skilled in the art also knows how to determine which active agents are suitable for loading silk films, i.e. whether an active agent of interest possesses, for example, at least one positive charge at the pH of the aqueous solution which is used for silk film loading, or which active agents are suitable for being incorporated into silk films, i.e. whether an active agent of interest possesses, for example, at least one positive charged at the pH of the aqueous solution which is used for silk film casting. Suitable methods include titration methods and the measurement of the zeta-potential during titration.

If the active agent is a peptide or a protein or any other amphiphilic compound, the presence of an overall positive net charge is dependent on the isoelectric point (pI) value of the active agent. The isoelectric point, sometimes abbreviated IEP, is the pH at which a particular molecule or surface carries no net electrical charge. For example, amphoteric molecules or zwitterions contain both positive and negative charges depending on the functional groups present in the molecule. The net charge on the molecule is affected by pH of their surrounding environment and can become more positively or negatively charged due to the loss or gain of protons. The pI the pH value at which the molecule carries no electrical charge or the negative and positive charges are equal.

Methods for determining whether a peptide or protein at a certain pH has a predominant net charge are known in the art. For example, suitable tools for calculating the pI value of peptides or proteins are provided by ExPasyProteomic server (www.expasy.ch). The program "Compute pI/Mw" is a tool which allows the computation of the theoretical pI (isoelectric point) and Mw (molecular weight) for a list of database entries (UniProtKnowledgebase (Swiss-prot or TrEMBL)) or for user entered sequences. Prediction of pI values are also described in Bjellqvist et al. (1993) and Gasteider et al. (2005) (Bjellqvist, B., The focusing positions of polypeptides in immobilized pH gradients can be predicted from their amino acid sequences. Electrophoresis 1993, 14, 1023-1031. Gasteiger E., Protein Identification and Analysis Tools on the ExPASy Server, (In) John M. Walker (ed): The Proteomics Protocols Handbook, Humana Press (2005).

The inventors of the present invention observed that the use of an aqueous solution or dispersion having a pH that is lower than the pI of the silk used for silk film formation results in a positively charged silk film. In this respect, it is preferred that the active agent added to the aqueous solution or dispersion is negatively charged at the pH of the aqueous solution or dispersion in order to achieve effective incorporation of the active agent into the silk film. Further, the inventors of the present invention observed that the use of an aqueous solution or dispersion having a pH that is higher than the pI of the silk used for silk film formation results in a negatively charged film. In this respect, it is preferred that the active agent added to the aqueous solution or dispersion is positively charged at the pH of the aqueous solution or dispersion in order to achieve effective incorporation of the active agent into the silk film. The incorporation of the active agent into the silk film preferably arises from electrostatic and/or hydrophobic interactions between the silk material and the active agent.

Thus, it is preferred that the active agent comprised in the silk film is positively charged, if the silk film has a negative net charge. It is further preferred that the active agent comprised in the silk film is negatively charged, if the silk film has a positive net charge.

The active agent may be released from the silk film, particularly from the active agent release sheet being part of the silk film or forming the silk film, by diffusion and/or degradation upon exposure to a surrounding environment.

In one embodiment, the surrounding environment is a physiological environment (e.g. a physiological medium). It is preferred that the physiological environment (e.g. the physiological medium) is selected from the group consisting of a physiological buffered solution or a body fluid, e.g. blood, lymph or liquor. It is also preferred that the physiological environment is an organ (e.g. skin) or a part of an organ (e.g. tissue). The release of the active agent from the silk film, particularly from the active agent release sheet being part of the silk film or forming the silk film, can be induced by introducing the silk film into a physiological buffered aqueous solution or a body fluid such as blood, lymph or liquor, or by applying the silk film onto an organ (e.g. skin) or part of an organ (e.g. tissue).

In one another embodiment, the surrounding environment is a non-physiological environment (e.g. a non-physiological medium). It is preferred that the non-physiological environment (e.g. the non-physiological medium) is selected from the group consisting of an aqueous solution such as water or a buffered aqueous solution, an alcoholic solution, and an organic solution.

It should be further noted that the active agent(s) may be released from the silk film, particularly from the active agent release sheet being part of the silk film or forming the silk film, by diffusion and/or degradation upon exposure to a surrounding intracorporeal or extracorporeal environment.

Preferably, the release of the active agent displays relatively linear kinetics, thereby providing a constant supply of the active agent over the release period.

It is preferred that less than 20%, preferably less than 15%, more preferably less than 10%, and most preferably less than 5%, e.g. less than 20, 19, 18, 17, 16, 15, 14, 13, 12, 11, 10, 9, 8, 7, 6, or 5%, of the active agent is released, particularly into the surrounding environment such as physiological environment or non-physiological environment (see above), within the first 24 hours.

It is, alternatively or additionally, preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 36 hours. It is, alternatively or additionally, preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 48 hours. It is, alternatively or additionally, preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 72 hours.

It is, alternatively or additionally, more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 7 days. It is, alternatively or additionally, more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 14 days. It is, alternatively or additionally, more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 20 days. It is, alternatively or additionally, more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 30 days. It is, alternatively or additionally, more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 35 days.

It is, alternatively or additionally, even more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 5 weeks. It is, alternatively or additionally, even more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 6 weeks. It is, alternatively or additionally, even more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 7 weeks. It is, alternatively or additionally, even more preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 8 weeks.

It is, alternatively or additionally, most preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 3 months. It is, alternatively or additionally, most preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 4 months. It is, alternatively or additionally, most preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 5 months. It is, alternatively or additionally, most preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 6 months. It is, alternatively or additionally, most preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 7 months. It is, alternatively or additionally, most preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 8 months. It is, alternatively or additionally, most preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 9 months. It is, alternatively or additionally, most preferred that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released, particularly into the surrounding environment such as physiological environment or non-physiological environment (see above), within 10 months.

It is particularly preferred that less than 20%, preferably less than 15%, more preferably less than 10%, and most preferably less than 5%, e.g. less than 20, 19, 18, 17, 16, 15, 14, 13, 12, 11, 10, 9, 8, 7, 6, or 5%, of the active agent is released into the physiological environment such as physiological buffered solution or body fluid, e.g. blood, lymph or liquor, within the first 24 hours, and/or that more than 50%, preferably more than 70%, more preferably more than 80%, and most preferably 100%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, of the active agent is released into the physiological environment such as physiological buffered solution or body fluid, e.g. blood, lymph or liquor, within 30 days.

The one or more release modifying layers comprise or consist of a release modifying material (e.g. a silk material). In one embodiment, the one or more release modifying layers comprise or consist of at least one release modifying agent. It is preferred that the release modifying agent is selected from the group consisting of a (i) silk polypeptide, (ii) polyester, preferably polylactide, polyglycolide, polylactic polyglycolic copolymer (PLGA), and blend of polylactic polyglycolic copolymer (PLGA) and polylactide, (iii) polyether, preferably polycaprolactone (PCL), (iv) polyanhydride, (v) polyalkylcyanoacrylate, preferably n-butyl cyanoacrylate, (vi) polyacrylamide, (vii) polyurethane, and (viii) polyvinylpirrolidone (PVP). It is more preferred that the release modifying agent is a silk polypeptide.

The silk film, particularly the one or more first silk film layers and/or the one or more second silk film layers, comprise a silk material. In one embodiment, the silk film, particularly the one or more first silk film layers and/or the one or more second silk film layers, comprise at least one silk polypeptide.

Naturally, the silk polypeptide of the silk film, particularly of the one or more first silk film layers and/or of the one or more second silk film layers, possess at least one negative charge at the carboxyl terminus. The person skilled in the art also knows how to select appropriate amino acid sequences in order obtain a silk polypeptide having an overall negative or positive net charge. For example, this can be achieved by selecting or generating silk sequences comprising negatively charged amino acids or positively charged amino acids. A suitable negatively charged silk polypeptide is, for example, the silk polypeptide $C_{16}$ which comprises 16 repeats of the sequence of module C (SEQ ID NO: 21) or variants thereof. In addition, a suitable positively charged silk polypeptide is, for example, the silk polypeptide $C^{Kappa}_{16}$ which comprises 16 repeats of the sequence of module $C^{Kappa}$ (SEQ ID NO: 43) or variants thereof.

Preferably, the silk polypeptide consists of between 6 to 1500 amino acids, more preferably of between 200 to 1300 amino acids, even more preferably of between 250 to 1200 amino acids, and most preferably of between 500 to 1000 amino acids.

The silk polypeptide may be expressed in a recombinant, e.g. microbial, insect, plant, or mammalian expression system, i.e. separated from its natural milieu, (recombinant silk polypeptide), or may be harvested from natural sources, e.g. spider, silk worm, bee, mussel, or fly larvae. The silk polypeptide may be an isolated or a purified silk polypeptide. In particular, a "purified silk polypeptide" or an "isolated silk polypeptide" is free or substantially free of cellular material, production/fermentation remnants, and/or other contaminating proteins from the cell or tissue source from which the silk polypeptide is purified or isolated. The language "substantially free of cellular material" includes preparations of a silk polypeptide in which the silk polypeptide is separated from cellular components of the cells from which it is produced or harvested. A silk polypeptide that is "substantially free" of cellular material, production/fermentation remnants, and/or other contaminating proteins from the cell or tissue source from which the silk polypeptide is purified or isolated includes preparations of silk polypeptides having less than about 30%, 20%, 10%, 5%, 1%, or 0.1% (by dry weight) of contaminating protein and/or less than about 30%, 20%, 10%, 5%, 1%, or 0.1% (by dry weight) of contaminating lipid, DNA or salt.

It is preferred that the silk polypeptide is a recombinant silk polypeptide. It is further preferred that the silk polypeptide is a (recombinant) spider silk polypeptide, more preferably a (recombinant) major ampullate silk polypeptide such as a (recombinant) dragline silk polypeptide, a (recombinant) minor ampullate silk polypeptide, or a (recombinant)

flagelliform silk polypeptide of an orb-web spider (e.g. Araneidae or Araneoids), an (recombinant) insect silk polypeptide, a (recombinant) mussel byssus silk polypeptide, or a mixture thereof. The orb-web spider may be selected from the group consisting of *Araneus diadematus, Nephila clavipes*, and *Latrodectus hesperus*. The insect silk polypeptide may be of Lepidoptera, particularly Bombycidae such as *Bombyx mori*. The insect silk polypeptide may also be of Hymenoptera, particularly Apoidea such as Anthophila.

It is, alternatively or additionally, preferred that the silk polypeptide comprises or consists of at least two repetitive units. It should be noted that the terms "repetitive unit" and "repeat unit" can interchangeable be used in the context of the present invention.

The term "repetitive unit", as used herein, refers to a region which corresponds in amino acid sequence to a region that comprises or consists of at least one peptide motif (e.g. AAAAAA (SEQ ID NO: 13) or GPGQQ (SEQ ID NO: 4)) that repetitively occurs within a naturally occurring silk polypeptide (e.g. MaSpI, ADF-3, ADF-4, or Flag) (i.e. identical amino acid sequence) or to an amino acid sequence substantially similar thereto (i.e. variational amino acid sequence). In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over the whole length of the respective reference naturally occurring amino acid sequence.

A "repetitive unit" having an amino acid sequence which is "substantially similar" to a corresponding amino acid sequence within a naturally occurring silk polypeptide (i.e. wild-type repetitive unit) is also similar with respect to its functional properties; e.g. a silk polypeptide comprising a "substantially similar repetitive unit" is still capable of forming a film. The skilled person can readily assess whether a silk polypeptide comprising a "substantially similar repetitive unit" is still capable of forming a film, e.g. by producing an aqueous (buffered) solution comprising the silk polypeptide comprising the "substantially similar repetitive unit", casting said solution onto a solid support and subsequently drying said solution (see experimental section). Preferably, the produced silk film is a self-supporting film, i.e. a silk film that has the capacity for supporting itself without the help of additional materials such as carrier elements.

A "repetitive unit" having an amino acid sequence which is "identical" to the amino acid sequence of a naturally occurring silk polypeptide can be, for example, a portion of a silk polypeptide corresponding to one or more peptide motifs of MaSp I (SEQ ID NO: 35) MaSp II (SEQ ID NO: 36), ADF-3 (SEQ ID NO: 1) and/or ADF-4 (SEQ ID NO: 2). A "repetitive unit" having an amino acid sequence which is "substantially similar" to the amino acid sequence of a naturally occurring silk polypeptide can be, for example, a portion of a silk polypeptide corresponding to one or more peptide motifs of MaSpI (SEQ ID NO: 35) MaSpII (SEQ ID NO: 36), ADF-3 (SEQ ID NO: 1) and/or ADF-4 (SEQ ID NO: 2), but having one or more amino acid substitution(s) at (a) specific amino acid position(s).

The term, a "repetitive unit", as used herein, does not include the non-repetitive hydrophilic amino acid domain generally thought to be present at the amino terminus and/or carboxyl terminus of naturally occurring silk polypeptides.

The term a "repetitive unit", as used herein, further refers to an amino acid sequence with a length of 3 to 200 amino acids, or 5 to 150 amino acids, preferably with a length of 10 to 100 amino acids, or 15 to 80 amino acids and more preferably with a length of 18 to 60, or 20 to 40 amino acids. For example, the repetitive unit according to the present invention can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 amino acids. Preferably, the repetitive unit consists of 3, 4, 5, 6, 7, 8, 9, 10, 12, 15, 18, 20, 24, 27, 28, 30, 34, 35, or 39 amino acids.

Preferably, the silk polypeptide comprises of between 2 to 100 repetitive units, i.e. at least 2, 3, 4, 5, 6, 7, 8, 9, 10, 11, 12, 13, 14, 15, 16, 17, 18, 19, 20, 21, 22, 23, 24, 25, 26, 27, 28, 29, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 repetitive units. The repetitive units in the silk polypeptide may be the same (identical) or different. It is preferred that the same (identical) repetitive unit is used in the silk polypeptide at least 2 times, preferably 3, 4, 5, 6, 7, 8, 9, 10, 11, 12, 13, 14, 15, 16, 17, 18, 19, 20, 21, 22, 23, 24, or more times.

It is preferred that the silk polypeptide comprises or consists of at least 50%, 60%, 65%, 70%, 75%, 80%, 85%, 90%, preferably at least 95% and most preferably 100% of repetitive units. It is particularly preferred that the silk polypeptide comprises or consists of at least 50%, 60%, 65%, 70%, 75%, 80%, 85%, 90%, preferably at least 95% and most preferably 100% of multiple copies of one identical repetitive unit (e.g. $A_2$, $Q_6$, or $C_{16}$, wherein the numerical 2, 6, or 16 represent the number of repetitive units) or multiple copies of two or more different repetitive units (e.g. $(AQ)_{24}$, or $(AQ)_{12}C_{16}$). Said silk polypeptide can further be modified by adding an artificial tag to facilitate the detection or purification of said polypeptide (e.g. T7 tag or His Tag).

The repetitive unit of the silk polypeptide can comprise or consist of an amino acid sequence of any region that comprises or consists of at least one peptide motif that repetitively occurs within a naturally occurring silk polypeptide known to one skilled in the art. Preferably, the repetitive unit of the silk polypeptide comprises or consists of an amino acid sequence of a region that comprises or consists of at least one peptide motif that repetitively occurs within an arthropod silk polypeptide, more preferably within a spider silk polypeptide, or an insect silk polypeptide. The repetitive unit of the silk polypeptide can also comprise or consist of an amino acid sequence of a region that comprises or consists of at least one peptide motif that repetitively occurs within a mussel silk polypeptide.

It is preferred that the spider silk repetitive unit comprises or consists of an amino acid sequence of a region that comprises or consists of at least one peptide motif that repetitively occurs within a naturally occurring major ampullate silk polypeptide (MaSp), such as a dragline silk polypeptide, a minor ampullate silk polypeptide (MiSp), or a flagelliform (FLAG) silk polypeptide. Most preferably, the repetitive unit comprises or consists of an amino acid sequence of a region that comprises or consists of at least one peptide motif that repetitively occurs within a naturally occurring dragline silk polypeptide or flagelliform silk polypeptide.

It is also preferred that the insect silk repetitive unit comprises or consists of an amino acid sequence of a region that comprises or consists of at least one peptide motif that repetitively occurs within a naturally occurring silk polypeptide of Lepidoptera. More preferably, the insect silk repetitive unit comprises or consists of an amino acid sequence of a region that comprises or consists of at least one peptide motif that repetitively occurs within a naturally occurring insect silk polypeptide of Bombycidae, most preferably of *Bombyx mori*.

Preferably, the silk polypeptide comprises or consists of at least two repetitive units each comprising at least one, preferably one, consensus sequence selected from the group consisting of:
(i) GPGXX (SEQ ID NO: 3), wherein X is any amino acid, preferably in each case independently selected from A, S, G, Y, P, and Q;
(ii) GGX, wherein X is any amino acid, preferably in each case independently selected from Y, P, R, S, A, T, N and Q, more preferably in each case independently selected from Y, P and Q;
(iii) $A_x$, wherein x is an integer from 5 to 10;
(iv) GGRPSDTYG (SEQ ID NO: 18); and
(v) GGRPSSSYG (SEQ ID NO: 19).

The above mentioned silk polypeptide preferably has a molecular weight of at least 5 kDa, e.g. of at least 5, 6, 7, 8, 9, 10, 11, 12, 13, 14, 15, 16, 17, 18, 19, or 20 kDa.

The term "consensus sequence", as used herein, refers to an amino acid sequence which contains amino acids which frequently occur in a certain position (e.g. "G") and wherein, other amino acids which are not further determined are replaced by the place holder "X".

The iterated (peptide) motifs GPGXX (SEQ ID NO: 3) and GGX, i.e. glycine rich motifs, provide flexibility to the silk polypeptide and thus, to the film formed from the silk polypeptide containing said motifs. In detail, the iterated GPGXX (SEQ ID NO: 3) motif forms β-turn spiral structures, which imparts elasticity to the silk polypeptide. Major ampullate and flagelliform silks both have a GPGXX (SEQ ID NO: 3) motif. The iterated GGX motif is associated with a helical structure having three amino acids per turn and is found in most spider silks. The GGX motif may provide additional elastic properties to the silk. The iterated polyalanine $A_x$ (peptide) motif forms a crystalline β-sheet structure that provides strength to the silk polypeptide. (WO 03/057727). The GGRPSDTYG (SEQ ID NO: 18) and GGRPSSSYG (SEQ ID NO: 19) (peptide) motifs have been selected from Resilin (WO 08/155304). Resilin is an elastomeric protein found in most arthropods (arthropoda). It is located in specialised regions of the cuticle, providing low stiffness and high strength (Elvin et al., Nature (473): 999-1002, 2005).

Thus, in one preferred embodiment, the silk polypeptide comprises or consists of repetitive units each comprising at least one (e.g. 1, 2, 3, 4, 5, 6, 7, 8, or 9), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), and GPGGS (SEQ ID NO: 11). In one further preferred embodiment of the present invention, the silk polypeptide comprises or consists of repetitive units each comprising at least one (e.g. 1, 2, 3, 4, 5, 8, 7, or 8), preferably one, amino acid sequence selected from the group consisting of GGY, GGP, GGA, GGR, GGS, GGT, GGN, and GGQ. In one additionally preferred embodiment of the present invention, the silk polypeptide comprises or consists of repetitive units each comprising at least one (e.g. 1, 2, 3, 4, 5, or 6), preferably one, amino acid sequence selected from the group consisting of AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), and AAAAAAAAAA (SEQ ID NO: 17).

In one another preferred embodiment, the silk polypeptide comprises or consists of repetitive units each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

More preferably, the silk polypeptide comprises or consists of repetitive units, which comprise or consist of
(i) GPGAS (SEQ ID NO: 5), AAAAAA (SEQ ID NO: 13), GGY, and GPGSG (SEQ ID NO: 6) as amino acid sequence, preferably in this order,
(ii) AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
(iii) GPGQQ (SEQ ID NO: 4), GPGQQ (SEQ ID NO: 4), GPGQQ (SEQ ID NO: 4) and GPGQQ (SEQ ID NO: 4) as amino acid sequence,
(iv) GPGGA (SEQ ID NO: 9), GGP, GPGGA (SEQ ID NO: 9), GGP, GPGGA (SEQ ID NO: 9), and GGP as amino acid sequence, preferably in this order,
(v) AAAAAAAA (SEQ ID NO: 15), GPGQG (SEQ ID NO: 40), and GGR as amino acid sequence, preferably in this order,
(vi) AAAAAAAA (SEQ ID NO: 15), GPGGG (SEQ ID NO: 10), GGR, GGN, and GGR as amino acid sequence, preferably in this order,
(vii) GGA, GGA, GGA, GGS, GGA, and GGS as amino acid sequence, preferably in this order, and/or
(viii) GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It is further preferred that the repetitive units are independently selected from module A (SEQ ID NO: 20) or variants thereof, module C (SEQ ID NO: 21) or variants thereof, module Q (SEQ ID NO: 22) or variants thereof, module S (SEQ ID NO: 23) or variants thereof, and module R (SEQ ID NO: 24) or variants thereof. Modules A (SEQ ID NO: 20) and Q (SEQ ID NO: 22) are based on the amino acid sequence of ADF-3 of the spider *Araneus diadematus*. Module C (SEQ ID NO: 21) is based on the amino acid sequence of ADF-4 of the spider *Araneus diadematus*. Modules S (SEQ ID NO: 23) and R (SEQ ID NO: 24) are based on Resilin (Arthropoda) (WO 2008/155304).

Thus, in one preferred embodiment, the repetitive units of the silk polypeptide consist of module A: GPYGP-GASAAAAAAGGYGPGSGQQ (SEQ ID NO: 20), module C: GSSAAAAAAAAASGPGGYGPENQGPSGPG-GYGPGGP (SEQ ID NO: 21), module Q: GPGQQGPGQQGPGQQGPGQQ (SEQ ID NO: 22), module S: PGSSAAAAAAAASGPGQGQGQGQGQG-GRPSDTYG (SEQ ID NO: 23), module R: SAAAAAAAAGPGGGNGGRPSDTYGAPGGGNG-GRPSSSYG (SEQ ID NO: 24), or variants thereof.

The silk polypeptide may comprise combined repeats of only one of these modules or of combinations thereof. Preferred combinations are characterized as follows (the repetitive units are arranged from N- to C-terminus): XY, wherein X and Y are independently selected from A, C, Q, R and S or variant thereof and are each different, i.e. X and Y are not C at the same time. Preferred combinations that are combined with each other are CA, AC, CQ, QC, CS, SC, CR, RC, SR, RS, AQ, QA, AS, SA, AR, RA, QS, SQ, QR, RQ, SR, and RS. In further preferred combinations blocks of three repetitive units are formed, which follow the following construction scheme: XYZ, wherein X and Y are independently selected from A, C, Q, R and S or variant thereof and are each different and Z is independently selected from A, C, Q, R and S or variant thereof, is preferably identical to X. Preferred combinations that are combined with each other are CAA, CAC, CAQ, CAR, CAS, ACA, ACC. ACQ, ACR, ACS, CQA, CQC, CQQ, CQR, CQS, QCA, QCC, QCQ, QCR, QCS, CSA; CSC, CSQ, CSR, CSS, SCA, SCC, SCQ, SCR, SCS, CRA, CRC, CRQ, CRR, CRS, RCA, RCC, RCQ, RCR, RCS, SRA, SRC, SRQ, SRR, SRS, RSA, RSC, RSQ, RSR, RSS, AQA, AQC, AQQ, AQR, AQS, QAA, QAC, QAQ, QAR, QAS, ASA; ASC, ASQ, ASR, ASS, SAA, SAC, SAQ, SAR, SAS, ARA, ARC, ARQ, ARR; ARS, RAA, RAC, RAQ, RAR, RAS, QSA, QSC, QSQ, QSR, QSS, SQA, SQC, SQQ, SQR, SQS, QRA, QRC, QRQ, QRR, QRS, RQA, RQC, RQQ, RQR, RQS, SRA. SRC. SRQ, SRE, SRS, RSA, RSC, RSQ, RSR, and RSS. It is noted that it is in each case possible that one of the repetitive units is a variant of the respectively indicated repetitive unit. Accordingly, preferred repetitive units comprised in the silk polypeptide follow the general structure $X_m$, $XY_n$ or $XYZ_o$, wherein m is between 4 and 100, i.e. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 or more; n is between 2 and 60, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60; and o is between 2 and 40, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40.

The terms "combined with each other" or "concatenated with each other", as used herein, mean that the modules (repetitive units) are directly combined or concatenated with each other, or mean that the modules (repetitive units) are combined or concatenated with each other via one or more spacer amino acids. Thus, in one embodiment, the modules (repetitive units) comprised in the silk polypeptide are directly combined or concatenated with each other. In one another embodiment, the modules (repetitive units) comprised in the silk polypeptide are combined or concatenated with each other via one or more spacer amino acids, preferably via 1 to 25 or 1 to 20 spacer amino acids, more preferably via 1 to 15 or 1 to 10 spacer amino acids, and most preferably, via 1 to 5 spacer amino acids, e.g. via 1, 2, 3, 4, 5, 6, 7, 8, 9, 10, 11, 12, 13, 14, 15, 16, 17, 18, 19, 20, 21, 22, 23, 24, or 25 spacer amino acids. Said spacer amino acid may be any amino acid naturally occurring in proteins. Preferably, said spacer amino acid is not proline. It is preferred that the spacer amino acid contains a charged group(s). Preferably, the spacer amino acid containing a charged group(s) is independently selected from the group consisting of aspartate, glutamate, histidine, and lysine. Said spacer amino acid should be an amino acid which does not negatively affect the ability of a silk polypeptide to form a film. Further, said spacer amino acid should be an amino acid which does not cause steric hindrance, e.g. an amino acid having a small size such as lysine and cysteine. In one more preferred embodiments, the silk polypeptide comprises modules which are directly combined with each other and modules which are combined with each other via 1 to 25 or 1 to 20 spacer amino acids, more preferably via 1 to 15 or 1 to 10 spacer amino acids, and most preferably, via 1 to 5 spacer amino acids, e.g. via 2, 3, 4, 5, 6, 7, 8, 9, 10, 11, 12, 13, 14, 15, 16, 17, 18, 19, 20, 21, 22, 23, 24, or 25 spacer amino acids.

A module A, C, Q, S, or R variant differs from the reference (wild-type) module A, C, Q, S, or R from which it is derived by up to 1, 2, 3, 4, 5, 6, 7, 8, 9, 10, 11, 12, 13, 14, or 15 amino acid changes in the amino acid sequence (i.e. substitutions, additions, insertions, deletions, N-terminal truncations and/or C-terminal truncations). Such a module variant can alternatively or additionally be characterised by a certain degree of sequence identity to the reference (wild-type) module from which it is derived. Thus, a module A, C, Q, S, or R variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) module A, C, Q, S, or R. Preferably, the sequence identity is over a continuous stretch of at least 10, 15, 18, 20, 24, 27, 28, 30, 34, 35, or more amino acids, preferably over the whole length of the respective reference (wild-type) module A, C, Q, S, or R.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) module A, C, Q, S, or R. It is further particularly preferred that the sequence identity is at least 80% over a continuous stretch of at least 10, 15, 18, 20, 24, 28, or 30 amino acids, is at least 85% over a continuous stretch of at least 10, 15, 18, 20, 24, 28, or 30 amino acids, is at least 90% over a continuous stretch of at least 10, 15, 18, 20, 24, 28, or 30 amino acids, is at least 95% over a continuous stretch of at least 10, 15, 18, 20, 24, 28, or 30 amino acids, is at least 98% over a continuous stretch of at least 10, 15, 18, 20, 24, 28, or 30 amino acids, or is at least 99% over a continuous stretch of at least 10, 15, 18, 20, 24, 28, or 30 amino acids of the respective reference (wild-type) module A, C, Q, S, or R.

A fragment (or deletion variant) of module A, C, Q, S, or R has preferably a deletion of up to 1, 2, 3, 4, 5, 6, 7, 8, 9, 10, 11, 12, 13, 14, or 15 amino acids at its N-terminus and/or at its C-terminus. The deletion can also be internally.

Additionally, the module A, C, Q, S, or R variant or fragment is only regarded as a module A, C, Q, S, or R variant or fragment within the context of the present invention, if the modifications with respect to the amino acid sequence on which the variant or fragment is based do not negatively affect the ability of the silk polypeptide to form a film. The skilled person can readily assess whether the silk polypeptide comprising a module A, C, Q, S, or R variant or fragment is still capable of forming a film, e.g. by producing an aqueous (buffered) solution comprising a silk polypeptide comprising a module A, C, Q, S, or R variant or fragment, casting said solution onto a solid support and subsequently drying said solution (see experimental section). Preferably, the produced silk film is a self-supporting film, i.e. a silk film that has the capacity for supporting itself without the help of additional materials such as carrier elements.

It is also preferred that the repetitive units are independently selected from module $A^C$ (SEQ ID NO: 25), module $A^K$ (SEQ ID NO: 26), module $C^C$ (SEQ ID NO: 27), module $C^{K1}$ (SEQ ID NO: 28), module $C^{K2}$ (SEQ ID NO: 29), module $C^{KC}$ (SEQ ID NO: 30), and module $C^{Kappa}$ (SEQ ID NO: 43). The modules $A^C$ (SEQ ID NO: 25), $A^K$ (SEQ ID NO: 26), $C^C$ (SEQ ID NO: 27), $C^{K1}$ (SEQ ID NO: 28), $C^{K2}$ (SEQ ID NO: 29), $C^{KC}$ (SEQ ID NO: 30) are variants of the module A which is based on the amino acid sequence of ADF-3 of the spider Araneus diadematus and of module C which is based on the amino acid sequence of ADF-4 of the spider Araneus diadematus (WO 2007/025719). In module $A^C$ (SEQ ID NO: 25) the amino acid S (serine) at position 21 has been replaced by the amino acid C (cysteine), in module $A^K$ (SEQ ID NO: 26) the amino acid S at position 21 has been replaced by the amino acid K (lysine), in module $C^C$ (SEQ ID NO: 27) the amino acid S at position 25 has been replaced by the amino acid 25 by C, in module $C^{K1}$ (SEQ ID NO: 28) the amino acid S at position 25 has been replaced by the amino acid K, in module $C^{K2}$ (SEQ ID NO: 29) the amino acid E (glutamate) at position 20 has been replaced by the amino acid K, and in module $C^{KC}$ (SEQ ID NO: 30) the amino acid E at position 20 has been replaced by the amino acid K and the amino acid S at position 25 has been replaced by the amino acid C (WO 2007/025719), and in module $C^{Kappa}$ (SEQ ID NO: 43), the amino acid E at position 20 has been replaced by the amino acid K. Thus, in a more preferred embodiment, the repetitive units in the silk polypeptide consist of module $A^C$: GPYGPGASAAAAAGGYGPGCGQQ (SEQ ID NO: 25), module $A^K$: GPYGPGASAAAAAGGYGPGKGQQ (SEQ ID NO: 26), module $C^C$: GSSAAAAAAAASGPGGYG-PENQGPCGPGGYGPGGP (SEQ ID NO: 27), module $C^{K1}$: GSSAAAAAAAASGPGGYGPENQGPKGPGGYGPGGP (SEQ ID NO: 28), module $C^{K2}$: GSSAAAAAAAASGPG-GYGPKNQGPSGPGGYGPGGP (SEQ ID NO: 29), module $C^{KC}$: GSSAAAAAAAASGPGGYGPKNQGPCGPG-GYGPGGP (SEQ ID NO: 30), or module $C^{Kappa}$: GSSAAAAAAAASGPGGYGPKNQGPSGPGGYGPGGP (SEQ ID NO: 43).

The modules $A^K$, $C^C$, $C^{K1}$, $C^{K2}$, $C^{KC}$, and $C^{Kappa}$ can also be combined with the modules A, C, Q, S, or R, i.e. module (repetitive unit) $A^K$ can be combined with module (repetitive unit) C (i.e. combination $A^K$C), or module (repetitive unit) $C^C$ can be combined with module (repetitive unit) C (i.e. combination $C^C$C), etc., under the proviso that the silk polypeptide comprises or consists of at least two repetitive units which are identical. Thus, the silk polypeptide can also comprise or consist of the modules $(AQA^K)_n$, $(QA^K)_n$, $(QA^KQ)_n$, $(A^KQA)_n$, $(A^KQA^K)_n$, $(CC^C)_n$, $(CC^CC)_n$, $(C^CC^CC)_n$, $(CC^CC^C)_n$, $(C^CQ)_n$, $(QC^C)_n$, $(QC^CQ)_n$, $(C^CQC)_n$, $(CQC^C)_n$, $(C^CQC^C)_n$, $(CC^{K1})_n$, $(C^{K1}C)_n$, $(C^{K1}CC)_n$, $(CC^{K1}C)_n$, $(C^{KC}C^{KC}C)_n$, $(CC^{KC}C^{KC})_n$, $(C^{KC}Q)_n$, $(QC^{KC})_n$, $(QC^{KC}Q)_n$, $(A^KC^{K1}Q)_n$, $(QC^{K2}A^K)_n$, or $(C^{K1}C^{K2}C)_n$, wherein n is at least 2, preferably 4, 5, 6, 7, 8, 10, 12, 16, or 20. As to the terms "combined with each other" or "concatenated with each other", it is referred to the definitions provided above. For example, the silk polypeptide comprises or consists of the modules $C_{16}C^C$, $C^CC_{16}$, $C_8C^CC_8$, $C_8C^C{}_8$, $C^C{}_8C_8$, $C_4C^C{}_8C_4$, $C^C{}_4C_8C^C{}_4$, $C^C(AQ)_{24}$, or $(AQ)_{24}C^C$.

It is more preferred that the repetitive units are independently selected from module A (SEQ ID NO: 20) or variants thereof, module C (SEQ ID NO: 21) or variants thereof, module Q (SEQ ID NO: 22) or variants thereof, module S (SEQ ID NO: 23) or variants thereof, module R (SEQ ID NO: 24) or variants thereof, module $A^C$ (SEQ ID NO: 25), module $A^K$ (SEQ ID NO: 26), module $C^C$ (SEQ ID NO: 27), module $C^{K1}$ (SEQ ID NO: 28), module $C^{K2}$ (SEQ ID NO: 29), module $C^{KC}$ (SEQ ID NO: 30), and module $C^{Kappa}$ (SEQ ID NO: 43).

The silk polypeptide can further comprise at least one non-repetitive (NR) unit, e.g. at least 1, 2, 3, 4, 5, 6, or more NR unit(s), preferably one NR unit. In the context of the present invention, the term "non-repetitive (NR) unit" refers to a region of amino acids present in a naturally occurring silk polypeptide that displays no obvious repetition pattern (non-repetitive unit or NR unit). Preferably, the amino acid sequence of the non-repetitive unit corresponds to a non-repetitive amino acid sequence of naturally occurring dragline polypeptides, preferably of ADF-3 (SEQ ID NO: 1) or ADF-4 (SEQ ID NO: 2), or to an amino acid sequence substantially similar thereto. The amino acid sequence of the non-repetitive unit may also correspond to a non-repetitive amino acid sequence of black widow. More preferably, the amino acid sequence of the non-repetitive unit corresponds to a non-repetitive carboxy terminal amino acid sequence of naturally occurring dragline polypeptides, preferably of ADF-3 (SEQ ID NO: 1) or ADF-4 (SEQ ID NO: 2), or to an amino acid sequence substantially similar thereto. Even more preferably, the amino acid sequence of the non-repetitive unit corresponds to a non-repetitive carboxy terminal amino acid sequence of ADF-3 (SEQ ID NO: 1) which comprises amino acids 513 through 636, or of ADF-4 (SEQ ID NO: 2) which comprises amino acids 302 through 410, or to an amino acid sequence substantially similar thereto.

In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over 20, 30, 40, 50, 60, 70, 80 or more amino acids, more preferably over the whole length of the respective reference non-repetitive (carboxy terminal) amino acid sequence of naturally occurring dragline polypeptides, preferably of ADF-3 (SEQ ID NO: 1) or ADF-4 (SEQ ID NO: 2). A "non-repetitive unit" having an amino acid sequence which is "substantially similar" to a corresponding non-repetitive (carboxy terminal) amino acid sequence within a naturally occurring dragline polypeptide (i.e. wild-type non-repetitive (carboxy terminal) unit), preferably within ADF-3 (SEQ ID NO: 1) or ADF-4 (SEQ ID NO: 2), is also similar with respect to its functional properties; e.g. a silk polypeptide comprising a "substantially similar non-repetitive unit" is still capable of forming a film. The skilled person can readily assess whether a silk polypeptide comprising a "substantially similar non-repetitive unit" is still capable of forming a film, e.g. by producing an aqueous (buffered) solution comprising the silk polypeptide comprising the "substantially similar non-repetitive unit", casting said solution onto a solid support and subsequently drying said solution (see experimental section). Preferably, the produced silk film is a self-supporting film, i.e. a silk film that has the capacity for supporting itself without the help of additional materials such as carrier elements.

Most preferably, the non-repetitive (NR) unit is selected from NR3 (SEQ ID NO: 31) or variants thereof, NR4 (SEQ ID NO: 32) or variants thereof, NR5 (SEQ ID NO: 33) or variants thereof, and NR6 (SEQ ID NO: 34) or variants thereof. The NR3 (SEQ ID NO: 31) unit is based on the amino acid sequence of ADF-3 of the spider *Araneus diadematus* and the NR4 (SEQ ID NO: 32) unit is based on the amino acid sequence of ADF-4 of the spider *Araneus diadematus* (WO 2006/008163). In addition, the NR5 (SEQ ID NO: 33) unit and the NR6 (SEQ ID NO: 34) unit is derived from *Latrodectus hesperus*.

A NR3, NR4, NR5, or NR6 unit variant differs from the reference NR3 (SEQ ID NO: 31), NR4 (SEQ ID NO: 32), NR5 (SEQ ID NO: 33), or NR6 (SEQ ID NO: 34) unit from which it is derived by up to 1, 2, 3, 4, 5, 6, 7, 8, 9, 10, 11, 12, 13, 14, 15, 16, 17, 18, 19, 20, 25, or 30 amino acid changes in the amino acid sequence (i.e. exchanges, insertions, deletions, N-terminal truncations and/or C-terminal truncations). Such a NR3, NR4, NR5, or NR6 unit variant can alternatively or additionally be characterised by a certain degree of sequence identity to the reference NR3, NR4, NR5, or NR6 unit from which it is derived. Thus, a NR3, NR4, NR5, or NR6 unit variant has a sequence identity of at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference NR3, NR4, NR5, or NR6 unit. Preferably, the sequence identity is over a continuous stretch of at least 10, 20, 30, 40, 50, 60, 70, 80, 90, or more amino acids, preferably over the whole length of the respective reference NR3, NR4, NR5, or NR6 unit.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference NR3, NR4, NR5, or NR6 unit. It is further particularly preferred that the sequence identity is at least 80% over a continuous stretch of at least 20, 30, 40, 50, 60, 70, or 80 amino acids, is at least 85% over a continuous stretch of at least 20, 30, 40, 50, 60, 70, or 80 amino acids, is at least 90% over a continuous stretch of at least 20, 30, 40, 50, 60, 70, or 80 amino acids, is at least 95% over a continuous stretch of at least 20, 30, 40, 50, 60, 70, or 80 amino acids, is at least 98% over a continuous stretch of at least 20, 30, 40, 50, 60, 70, or 80 amino acids, or is at least 99% over a continuous stretch of at least 20, 30, 40, 50, 60, 70, or 80 amino acids of the respective reference NR3, NR4, NR5, or NR6 unit.

A fragment (or deletion variant) of a NR3, NR4, NR5, or NR6 unit has preferably a deletion of up to 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 amino acids at its N-terminus and/or at its C-terminus. The deletion can also be internally.

Additionally, the NR3, NR4, NR5, or NR6 unit variant or fragment is only regarded as a NR3, NR4, NR5, or NR6 unit variant or fragment within the context of the present invention, if the modifications with respect to the amino acid sequence on which the variant or fragment is based do not negatively affect the ability of a silk polypeptide to form a film. The skilled person can readily assess whether the silk polypeptide comprising a NR3, NR4, NR5, or NR6 unit variant or fragment is still capable of forming a film, e.g. by producing an aqueous (buffered) solution comprising a silk polypeptide comprising a NR3, NR4, NR5, or NR6 unit variant or fragment, casting said solution onto a solid support and subsequently drying said solution (see experimental section). Preferably, the produced silk film is a self-supporting film, i.e. a silk film that has the capacity for supporting itself without the help of additional materials such as carrier elements.

It is even more preferred that the silk polypeptide is selected from the group consisting of ADF-3 (SEQ ID NO: 1) or variants thereof, ADF-4 (SEQ ID NO: 2) or variants thereof, MaSp I (SEQ ID NO: 35) or variants thereof, MaSp II (SEQ ID NO: 36) or variants thereof, $(C)_m$, $(C)_m NR_z$, $NR_z(C)_m$, $(C^{Kappa})_m$, $(C^{Kappa})_m NR_z$, $NR_z(C^{Kappa})_m$, $(AQ)_n$, $(AQ)_n NR_z$, $NR_z(AQ)_n$, $(QAQ)_o$, $NR_z(QAQ)_o$, and $(QAQ)_o NR_z$, wherein m is an integer of 4 to 64, i.e. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, n is an integer of 6 to 40, i.e. 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, o is an integer of 8 to 40, i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, z is an integer of 1 to 3, i.e. 1, 2, or 3, and NR is in each case independently a non-repetitive unit, preferably a NR3, NR4, NR5, or NR6 non-repetitive unit or a variant thereof.

The above mentioned formulas are defined by one of the following: In the formula (i) $(C)_m$, a "m" number of C modules, namely 4 to 64 C modules, represented by the amino acid sequence according to SEQ ID NO: 21, are combined with each other (ii) $(C)_m NR_z$, a "m" number of C modules, namely 4 to 64 C modules, represented by the amino acid sequence according to SEQ ID NO: 21, are combined with each other, wherein said C modules are further combined with a "z" number of non-repetitive (NR) units, namely 1 to 3 non-repetitive (NR) units, e.g. the non-repetitive (NR) units NR3 represented by the amino acid sequence according to SEQ ID NO: 31, NR4 represented by the amino acid sequence according to SEQ ID NO: 32, NR5 represented by the amino acid sequence according to SEQ ID NO: 33, or NR6 represented by the amino acid sequence according to SEQ ID NO: 34, (iii) $NR_z(C)_m$, a "z" number of non-repetitive (NR) units, namely 1 to 3 non-repetitive (NR) units, e.g. the non-repetitive (NR) units NR3 represented by the amino acid sequence according to SEQ ID NO: 31, NR4 represented by the amino acid sequence according to SEQ ID NO: 32, NR5 represented by the amino acid sequence according to SEQ ID NO: 33, or NR6 represented by the amino acid sequence according to SEQ ID NO: 34, is present (z=1) or are combined with each other (z=2 or 3), wherein said non-repetitive (NR) unit(s) is (are) further combined with a "m" number of C modules, namely 4 to 64 C modules, represented by the amino acid sequence according to SEQ ID NO: 21, (iv) $(AQ)_n$, a "n" number of A and Q module combinations, namely 6 to 40 A and Q module combinations, wherein module A is represented by the amino acid sequence according to SEQ ID NO: 20 and module Q is represented by the amino acid sequence according to SEQ ID NO: 22, are combined with each other, (v) $(AQ)_n NR_z$, a "n" number of A and Q module combinations, namely 6 to 40 A and Q module combinations, wherein module A is represented by the amino acid sequence according to SEQ ID NO: 20 and module Q is represented by the amino acid sequence according to SEQ ID NO: 22, are combined with each other, and wherein said A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 31, NR4 represented by the amino acid sequence according to SEQ ID NO: 32, NR5 represented by the amino acid sequence according to SEQ ID NO: 33, or NR6 represented by the amino acid sequence according to SEQ ID NO: 34, (vi) $NR_z(AQ)_n$, a "z" number of non-repetitive (NR) units, namely 1 to 3 non-repetitive (NR) units, e.g. the non-repetitive (NR) units NR3 represented by the amino acid sequence according to SEQ ID NO: 31, NR4 represented by the amino acid sequence according to SEQ ID NO: 32, NR5 represented by the amino acid sequence according to SEQ ID NO: 33, or NR6 represented by the amino acid sequence according to SEQ ID NO: 34, is present (z=1) or are combined with each other (z=2 or 3), wherein said non-repetitive (NR) unit(s) is (are) further combined with a "n" number of A and Q module combinations, namely 6 to 40 A and Q module combinations, wherein module A is represented by the amino acid sequence according to SEQ ID NO: 20 and module Q is represented by the amino acid sequence according to SEQ ID NO: 22, (vii) $(QAQ)_o$, a "o" number of Q, A and Q module combinations, namely 8 to 40 Q, A and Q module combinations, wherein module Q is represented by an amino acid sequence according to SEQ ID NO: 22 and module A is represented by the amino acid sequence according to SEQ ID NO: 20, are combined with each other, (viii) $(QAQ)_o NR_z$, a "o" number of Q, A and Q module combinations, namely 8 to 40 Q, A and Q module combinations, wherein module Q is represented by an amino acid sequence according to SEQ ID NO: 22 and module A is represented by the amino acid sequence according to SEQ ID NO: 20, are combined with each other, and wherein said Q, A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 31, NR4 represented by the amino acid sequence according to SEQ ID NO: 32, NR5 represented by the amino acid sequence according to SEQ ID NO: 33, or NR6 represented by the amino acid sequence according to SEQ ID NO: 34, and (ix) $NR_z(QAQ)_o$, a "z" number of non-repetitive (NR) units, namely 1 to 3 non-repetitive (NR) units, e.g. the non-repetitive (NR) units NR3 represented by the amino acid sequence according to SEQ ID NO: 31, NR4 represented by the amino acid sequence according to SEQ ID NO: 32, NR5 represented by the amino acid sequence according to SEQ ID NO: 33, or NR6 represented by the amino acid sequence according to SEQ ID NO: 34, is present (z=1) or are combined with each other (z=2 or 3), wherein said non-repetitive (NR) unit(s) is (are) further combined with a "o" number of Q, A and Q module combinations, namely 8 to 40 Q, A and Q module combinations, wherein module Q is represented by an amino acid sequence according to SEQ ID NO: 22 and module A is represented by the amino acid sequence according to SEQ ID NO: 20.

It is most preferred that the silk polypeptide is selected from the group consisting of $C_8$, $C_8NR4$, $NR4C_8$, $C_8NR3$, $NR3C_8$, $NR4C_8NR4$, $NR3C_8NR3$, $NR4C_8NR3$, $NR3C_8NR4$, $C_{16}$, $C_{16}NR4$, $NR4C_{16}$, $C_{16}NR3$, $NR3C_{16}$, $NR4C_{16}NR4$, $NR3C_{16}NR3$, $NR4C_{16}NR3$, $NR3C_{16}NR4$, $C_{32}$, $C_{32}NR4$, $NR4C_{32}$, $C_{32}NR3$, $NR3C_{32}$, $NR4C_{32}NR4$, $NR3C_{32}NR3$, $NR4C_{32}NR3$, $NR3C_{32}NR4$, $C^{Kappa}_{16}$, $C^{Kappa}_{16}NR4$, $NR4C^{Kappa}_{16}$, $C^{Kappa}_{16}NR3$, $NR3C^{Kappa}_{16}$, $NR4C^{Kappa}_{16}NR4$, $NR3C^{Kappa}_{16}NR3$, $NR4C^{Kappa}_{16}NR3$, $NR3C^{Kappa}_{16}NR4$, $(AQ)_{12}$, $(AQ)_{12}NR3$, $NR3(AQ)_{12}$, $(AQ)_{12}NR4$, $NR4(AQ)_{12}$, $NR3$ $(AQ)_{12}NR3$, $NR4$ $(AQ)_{12}NR4$, $NR3(AQ)_{12}NR4$, $NR4(AQ)_{12}NR3$, $(AQ)_{24}$, $(AQ)_{24}NR3$, $NR3(AQ)_{24}$, $(AQ)_{24}NR4$, $NR4(AQ)_{24}$, $NR3$ $(AQ)_{24}NR3$, $NR4(AQ)_{24}NR4$, $NR3(AQ)_{24}NR4$, $NR4(AQ)_{24}NR3$, $(QAQ)_8$, and $(QAQ)_{16}$.

An ADF-3, ADF-4, MaSp I or MaSp II variant differs from the reference (wild-type) ADF-3 (SEQ ID NO: 1), ADF-4 (SEQ ID NO: 2), MaSp I (SEQ ID NO: 35) or MaSp II (SEQ ID NO: 36) polypeptide from which it is derived by up to 150 (up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150) amino acid changes in the amino acid sequence (i.e. substitutions, insertions, deletions, N-terminal truncations and/or C-terminal truncations). Such a variant can alternatively or additionally be characterised by a certain degree of sequence identity to the reference (wild-type) polypeptide from which it is derived. Thus, an ADF-3, ADF-4, MaSp I or MaSp II variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) ADF-3, ADF-4, MaSp I or MaSp II polypeptide. Preferably, the sequence identity is over a continuous stretch of at least 20, 25, 30, 35, 40, 50, 60, 70, 80, 90, 100, 120, 150, 180, 200, 250, 300, 350, 400, or more amino acids, preferably over the whole length of the respective reference (wild-type) ADF-3, ADF-4, MaSp I or MaSp II polypeptide.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) ADF-3, ADF-4, MaSp I or MaSp II polypeptide. It is further particularly preferred that the sequence identity is at least 80% over a continuous stretch of at least 20, 30, 50, 100, 150, 200, 250, or 300 amino acids, is at least 85% over a continuous stretch of at least 20, 30, 50, 100, 150, 200, 250, or 300 amino acids, is at least 90% over a continuous stretch of at least 20, 30, 50, 100, 150, 200, 250, or 300 amino acids, is at least 95% over a continuous stretch of at least 20, 30, 50, 100, 150, 200, 250, or 300 amino acids, is at least 98% over a continuous stretch of at least 20, 30, 50, 100, 150, 200, 250, or 300 amino acids, or is at least 99% over a continuous stretch of at least 20, 30, 50, 100, 150, 200, 250, or 300 amino acids of the respective reference (wild-type) ADF-3, ADF-4, MaSp I or MaSp II polypeptide.

A fragment (or deletion variant) of the ADF-3 (SEQ ID NO: 1) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 350, 370, 400, 420, 450, 470, 500, 520, 550, 570, 600, or 610 amino acids at its N-terminus and/or at its C-terminus. The deletion can also be internally.

A fragment (or deletion variant) of the ADF-4 (SEQ ID NO: 2) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 330, 340, 350, 360, 370, 380, or 390 amino acids at its N-terminus and/or at its C-terminus. The deletion can also be internally.

A fragment (or deletion variant) of the MaSp I (SEQ ID NO: 35) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 620, 640, 660, 670, 680, or 690 amino acids at its N-terminus and/or at its C-terminus. The deletion can also be internally.

A fragment (or deletion variant) of the MaSp II (SEQ ID NO: 36) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 520, 540, 560, or 570 amino acids at its N-terminus and/or at its C-terminus. The deletion can also be internally.

Additionally, the ADF-3, ADF-4, MaSp I or MaSp II variant or fragment is only regarded as an ADF-3, ADF-4, MaSp I or MaSp II variant or fragment within the context of the present invention, if the modifications with respect to the amino acid sequence on which the variant or fragment is based do not negatively affect the ability of the silk polypeptide to form a film. The skilled person can readily assess whether the silk polypeptide comprising a ADF-3, ADF-4, MaSp I or MaSp II variant or fragment is still capable of forming a film, e.g. by producing an aqueous (buffered) solution comprising a silk polypeptide comprising a ADF-3, ADF-4, MaSp I or MaSp II variant or fragment, casting said solution onto a solid support and subsequently drying said solution (see experimental section). Preferably, the produced silk film is a self-supporting film, i.e. a silk film that has the capacity for supporting itself without the help of additional materials such as carrier elements.

The silk polypeptide may further comprise an amino terminal and/or a carboxy terminal TAG selected from the group consisting of (i) TAG$^{CYS1}$ consisting of the amino acid sequence GCGGGGGGSGGGG (SEQ ID NO: 37), (ii) TAG$^{CYS2}$ consisting of the amino acid sequence GCGGGGGG (SEQ ID NO: 38), (iii) TAG$^{CYS3}$ consisting of the amino acid sequence GCGGSGGGGSGGGG (SEQ ID NO: 39), (iv) TAG$^{LYS1}$ consisting of the amino acid sequence GKGGGGGGSGGGG (SEQ ID NO: 41), and (v) TAG$^{LYS2}$ consisting of the amino acid sequence GKGGGGGG (SEQ ID NO: 42). Said amino terminal and/or a carboxy terminal TAGs allow the coupling (by forming covalent bounds) of active agents to the silk polypeptide and, thus, to the silk film.

In one embodiment, the one or more first silk film layers have a thickness of at least 0.1, 0.5, 1, 2, 3, 4, 5, 10, 15, 20, 25, 30, 35, 40, 45, 50, 60, 70, 80, 90, 100, 110, 120, 130, 140, 150, 160, 170, 180, 190, 200, 300, 400, 500, 600, 700, 800, 900 µm, 1, 2, 3, 4, 5, 6, 7, 8, 9 mm, or 1 cm. In one further embodiment, the one or more first silk film layers have a thickness of between 0.1 µm and 1 cm, preferably of between 1 µm and 5 mm or of between 1 µm and 1 mm, more preferably of between 1 µm and 200 µm or of between 1 µm and 100 µm, and most preferably of between 1 µm and 50 µm or of between 1 µm and 40 µm. In this respect, it should be noted that the thickness of the first silk film layers may be varied depending on the amount of the active agent to be incorporated. For example, an increased thickness of the first silk film layers allows the incorporation of a higher amount of the active agent.

In one another embodiment, the one or more release modifying layers have a thickness of at least 0.05, 0.1, 0.5, 1, 2, 3, 4, 5, 10, 15, 20, 25, 30, 35, 40, 45, 50, 60, 70, 80, 90, 100, 110, 120, 130, 140, 150, 160, 170, 180, 190, 200, 300, 400, or 500 µm. In one further embodiment, the one or more release modifying layers have a thickness of between 0.05 µm and 500 µm or of between 0.1 µm and 500 µm, preferably of between 0.5 µm and 200 µm or of between 0.5 µm and 100 µm, even more preferably of between 0.5 µm and 80 µm or of between 0.5 µm and 50 µm, and most preferably of between 0.5 µm and 40 µm or of between 0.5 µm and 20 µm. In this respect, it should be noted that the thickness of the release modifying layers may be varied depending on the desired release of the active agent. For example, an increased thickness of the release modifying layers allows a slower release of the active agent.

In one alternative or additional embodiment, the one or more second silk film layers have a thickness of at least 0.1, 0.5, 1, 2, 3, 4, 5, 10, 15, 20, 25, 30, 35, 40, 45, 50, 60, 70, 80, 90, 100, 110, 120, 130, 140, 150, 160, 170, 180, 190, 200, 300, 400, 500, 600, 700, 800, 900 µm, 1, 2, 3, 4, 5, 6, 7, 8, 9 mm, or 1 cm. In one further embodiment, the one or more second silk film layers have a thickness of between 0.1 µm and 1 cm, preferably of between 1 µm and 5 mm or of between 1 µm and 1 mm, more preferably of between 1 µm and 200 µm or of between 1 µm and 100 µm, and most preferably of between 1 µm and 50 µm or of between 1 µm and 40 µm. In this respect, it should be noted that the thickness of the second silk film layers may be varied depending on the desired retardation of the active agent. For example, an increased thickness of the second silk film layers allows a better retardation of release of the active agent.

In one further embodiment, the coated silk film is water-soluble or water-insoluble. As to the production of water-insoluble coated silk films, it is referred to the eighth aspect of the present invention.

In a second aspect, the present invention relates to a pharmaceutical composition comprising or consisting of the coated silk film according to the first aspect, wherein the active agent is a pharmaceutical agent. As to the preferred pharmaceutical agents, it is referred to the first aspect of the present invention.

The coated silk film of the present invention may be administered in the form of any suitable pharmaceutical composition. Said pharmaceutical compositions include, but are not limited to, wound closure or coverage systems, such as plaster, patches, and wound dressings, protection systems, such as bandages, skin substitution systems, such as skin grafts like autografts, implants, contact lenses, and depot systems. The contact lenses may comprise the coated silk film of the first aspect. The pharmaceutical agents comprised therein may be anti-inflammatory agents. The depot systems may comprise contraceptive agents.

The pharmaceutical composition may further comprise one or more pharmaceutically acceptable carriers, diluents and/or excipients. Said pharmaceutically acceptable carriers, diluents and/or excipients may already be comprised in the aqueous solution or dispersion used for silk film formation or may subsequently be added to or loaded into the silk film. The term "pharmaceutically acceptable", as used herein, refers to the non-toxicity of a material which does not interact with the action of the active component of the pharmaceutical composition. The term "carrier", as used herein, relates to one or more compatible solid or liquid fillers or diluents, which are suitable for an administration to an individual. The term "carrier" relates to a natural or synthetic organic or inorganic component which is combined with an active agent in order to facilitate the application of the active agent. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds. The term "diluent", as used herein, relates a diluting and/or thinning agent. Moreover, the term "diluent" includes any one or more of fluid, liquid or solid suspension and/or mixing media. The term "excipient", as used herein, is intended to indicate all substances in a pharmaceutical composition which are not active ingredients such as binders, lubricants, thickeners, surface active agents, preservatives, emulsifiers, buffers, flavoring agents, or colorants.

Preferably, the pharmaceutical composition is useful for treating or reducing the severity of a disease or medical condition by administering said pharmaceutical composition to an individual. The pharmaceutical composition can be administered locally or systemically, preferably locally. Said treatment includes, but is not limited to, therapeutical treatment, prophylactic treatment, and preventive treatment.

The terms "individual" and "subject" are used herein interchangeably. They preferably refer to a human or another mammal (e.g. mouse, rat, rabbit, dog, cat, cattle, swine, sheep, horse or primate). Unless otherwise stated, the terms "individual" and "subject" do not denote a particular age and, thus, encompass adults, elderlies, children, and newborns.

The term "disease (also designated as disorder)", as used herein, refers to an abnormal condition that affects the body of an individual. A disease is often construed as a medical condition associated with specific symptoms and signs. A disease may be caused by factors originally from an external source, such as infectious disease, or it may be caused by internal dysfunctions. In humans, a disease is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

Preferably, the disease is selected from the group consisting of an infectious disease, such as herpes, an autoimmune disease, such as psoriasis, a cutaneous disease, such as acne, rosacea, dermatitis or eczema, and a gastro-intestinal disease, such as dyspepsia or indigestion. The term "infectious disease", as used herein, refers to any disease which can be transmitted from individual to individual or from organism to organism, and is caused by a microbial agent. Infectious diseases are known in the art and include, for example, a viral disease, a bacterial disease, or a parasitic disease, which diseases are caused by a virus, a bacterium, and a parasite, respectively. The term "cutaneous disease", as used herein, refers to any disease that affects the integumentary system, the organ system that encloses the body and includes skin, hair, nails, and related muscle and glands.

Preferably, the medical condition is selected from the group consisting of burns, skin lesions, and wounds, such as superficial or inner wounds.

The term "therapeutic treatment", as used herein, relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease. The terms "prophylactic treatment" or "preventive treatment", as used herein, relate to any treatment that is intended to prevent a disease from occurring in an individual. The terms "prophylactic treatment" or "preventive treatment" are used herein interchangeably.

As mentioned above, the pharmaceutical composition may be administered to an individual in need thereof. The term "administration", as used herein, refers to the manner in which the pharmaceutical composition is presented to an individual. The pharmaceutical composition according to the invention may be administered to an individual using several ways. Preferred forms of administration include, but are not limited to, intradermal, transdermal, and topical administrations, particularly to the skin or tissue.

Preferably, the pharmaceutical composition is useful for controlled and sustained delivery of the pharmaceutical agent. Due the constant release profile of the coated silk film, the pharmaceutical composition comprising or consisting of the coated silk film is capable of releasing the loaded, attached, and/or incorporated pharmaceutical agent over a period of time, e.g. several days or weeks.

It is also possible to apply the coated silk film comprised in the pharmaceutical composition to several preferential objects including, but not limited to, meshes, scaffolds, patches, and nonwovens.

In a third aspect, the present invention relates to a cosmetic composition comprising or consisting of the coated silk film according to the first aspect, wherein the active agent is a cosmetic agent. As to the preferred cosmetic agents, it is referred to the first aspect of the present invention.

The coated silk film of the present invention may be administered in the form of any suitable cosmetic composition. Said cosmetic compositions include, but are not limited to, skin care products, such as skin masks, cleaning wipes, cleaning pads, creams, lotions or gels, and hair care products, such as conditioners or shampoos.

The cosmetic composition may further comprise one or more cosmetically acceptable carriers, diluents and/or excipients. Said cosmetically acceptable carriers, diluents and/or excipients may already be comprised in the aqueous solution used for silk film formation or may subsequently be added to or loaded into the silk film. The term "cosmetically acceptable", as used herein, refers to the non-toxicity of a material which does not interact with the action of the active component of the cosmetic composition.

The cosmetic composition according to the invention may be administered to an individual using several ways. A preferred form of administration is the topical administration, particularly to the skin.

Preferably, the cosmetic composition is useful for controlled and sustained delivery of the cosmetic agent. Due the constant release profile of the coated silk film, the cosmetic composition comprising or consisting of the coated silk film is capable of releasing the loaded, attached, and/or incorporated cosmetic agent over a period of time, e.g. several days or weeks.

It is also possible to apply the coated silk film comprised in the cosmetic composition to several preferential objects including, but not limited to, meshes, scaffolds, patches, and nonwovens.

In a fourth aspect, the present invention relates to a coated silk film according to the first aspect or pharmaceutical composition according to the second aspect for use in medicine. Preferably, the coated silk film according to the first aspect or the pharmaceutical composition according to the second aspect is for the treatment of a disease or medical condition.

It is preferred that the coated silk film comprises an active agent such as a biological agent, pharmaceutical agent, or cosmetic agent, preferably a pharmaceutical agent. As to the preferred biological agents, pharmaceutical agents, or cosmetic agents, it is referred to the first aspect of the present invention.

It is further preferred that the disease is selected from the group consisting of an infectious disease, such as herpes, an autoimmune disease, such as psoriasis, a cutaneous disease, such as acne, rosacea, dermatitis or eczema, and a gastrointestinal disease, such as dyspepsia or indigestion. It is also preferred that the medical condition is selected from the group consisting of burns, skin lesions, and wounds such as superficial wounds or inner wounds.

In a fifth aspect, the present invention relates to a coated silk film according to the first aspect or pharmaceutical composition according to the second aspect for controlled and sustained release of at least one pharmaceutical agent. As to the preferred pharmaceutical agents, it is referred to the first aspect of the present invention.

The pharmaceutical agent may be released from the coated silk film or pharmaceutical composition comprising or consisting of the coated silk film by diffusion and/or degradation upon exposure to a physiological environment (e.g. a physiological medium). The physiological environment (e.g. the physiological medium) may be a physiological buffered solution or a body fluid, e.g. blood, lymph or liquor. The release of the pharmaceutical agent from the coated silk film or pharmaceutical composition comprising or consisting of the coated silk film may be induced by introducing the coated silk film or pharmaceutical composition comprising or consisting of the coated silk film into a body fluid such as blood, lymph or liquor, or by applying the coated silk film or pharmaceutical composition comprising or consisting of the coated silk film onto an organ (e.g. skin) or a part of an organ (e.g. tissue).

Preferably, the release of the pharmaceutical agent displays relatively linear kinetics, thereby providing a constant supply of the pharmaceutical agent over the release period.

It is preferred that less than 20%, preferably less than 15%, more preferably less than 10%, and most preferably less than 5%, e.g. less than 20, 19, 18, 17, 16, 15, 14, 13, 12, 11, 10, 9, 8, 7, 6, or 5%, of the pharmaceutical agent is released, particularly into the physiological environment, within the first 24 hours.

It is, alternatively or additionally, preferred that more than 50%, preferably more than 70%, more preferably more than 80%, and most preferably 100% of the pharmaceutical agent is released, particularly into the physiological environment, within 36 hours. It is, alternatively or additionally, preferred that more than 50%, preferably more than 70%, more preferably more than 80%, and most preferably 100% of the pharmaceutical agent is released, particularly into the physiological environment, within 48 hours. It is, alternatively or additionally, preferred that more than 50%, preferably more than 70%, more preferably more than 80%, and most preferably 100% of the pharmaceutical agent is released, particularly into the physiological environment, within 72 hours.

It is, alternatively or additionally, more preferred that more than 50%, preferably more than 70%, more preferably more than 80%, and most preferably 100% of the pharmaceutical agent is released, particularly into the physiological environment, within 7 days. It is, alternatively or additionally, more preferred that more than 50%, preferably more than 70%, more preferably more than 80%, and most preferably 100% of the pharmaceutical agent is released, particularly into the physiological environment, within 14 days. It is, alternatively or additionally, more preferred that more than 50%, preferably more than 70%, more preferably more than 80%, and most preferably 100% of the pharmaceutical agent is released, particularly into the physiological environment, within 20 days. It is, alternatively or additionally, more preferred that more than 50%, preferably more than 70%, more preferably more than 80%, and most preferably 100% of the pharmaceutical agent is released, particularly into the physiological environment, within 30 days. It is, alternatively or additionally, more preferred that more than 50%, preferably more than 70%, more preferably more than 80%, and most preferably 100% of the pharmaceutical agent is released, particularly into the physiological environment, within 35 days.

It is, alternatively or additionally, even more preferred that more than 50%, preferably more than 70%, more preferably more than 80%, and most preferably 100% of the pharmaceutical agent is released, particularly into the physiological environment, within 5 weeks. It is, alternatively or additionally, even more preferred that more than 50%, preferably more than 70%, more preferably more than 80%, and most preferably 100% of the pharmaceutical agent is released, particularly into the physiological environment, within 6 weeks. It is, alternatively or additionally, even more preferred that more than 50%, preferably more than 70%, more preferably more than 80%, and most preferably 100% of the pharmaceutical agent is released, particularly into the physiological environment, within 7 weeks. It is, alternatively or additionally, even more preferred that more than 50%, preferably more than 70%, more preferably more than 80%, and most preferably 100% of the pharmaceutical agent is released, particularly into the physiological environment, within 8 weeks.

It is, alternatively or additionally, most preferred that more than 50%, preferably more than 70%, more preferably more than 80%, and most preferably 100% of the pharmaceutical agent is released, particularly into the physiological environment, within 3 months. It is, alternatively or additionally, most preferred that more than 50%, preferably more than 70%, more preferably more than 80%, and most preferably 100% of the pharmaceutical agent is released, particularly into the physiological environment, within 4 months. It is, alternatively or additionally, most preferred that more than 50%, preferably more than 70%, more preferably more than 80%, and most preferably 100% of the pharmaceutical agent is released, particularly into the physiological environment, within 5 months. It is, alternatively or additionally, most preferred that more than 50%, preferably more than 70%, more preferably more than 80%, and most preferably 100% of the pharmaceutical agent is released, particularly into the physiological environment, within 6 months. It is, alternatively or additionally, most preferred that more than 50%, preferably more than 70%, more preferably more than 80%, and most preferably 100% of the pharmaceutical agent is released, particularly into the physiological environment, within 7 months. It is, alternatively or additionally, most preferred that more than 50%, preferably more than 70%, more preferably more than 80%, and most preferably 100% of the pharmaceutical agent is released, particularly into the physiological environment, within 8 months. It is, alternatively or additionally, most preferred that more than 50%, preferably more than 70%, more preferably more than 80%, and most preferably 100% of the pharmaceutical agent is released, particularly into the physiological environment, within 9 months. It is, alternatively or additionally, most preferred that more than 50%, preferably more than 70%, more preferably more than 80%, and most preferably 100% of the pharmaceutical agent is released, particularly into the physiological environment, within 10 months.

In a sixth aspect, the present invention relates to a coated silk film according to the first aspect or pharmaceutical composition according to the second aspect for the treatment of wounds, skin diseases, or skin defects. The coated silk film according to the first aspect preferably comprises a pharmaceutical agent. As to the preferred embodiments of the pharmaceutical agent, it is referred to the first aspect of the present invention.

The term "wound", as used herein, includes damages to any organ, particularly tissue, in an individual. The wound may be comprised on the surface of the body of an individual, (i.e. a superficial wound), or may be comprised within the body of an individual (i.e. an internal wound). The wound may have been caused by any means including, but not limited to, infections, inflammations, surgical interventions, external components such as sharp objects, e.g. scalpels, knifes or nails, and external circumstances, such as accidents, e.g. bicycle, motor vehicle, or auto accidents.

The wound may be comprised on the surface (e.g. skin) of the body of an individual (i.e. a superficial wound), or may be comprised within the body of an individual (i.e. an internal wound). The wound may have been caused by any means including, but not limited to, infections, inflammations, surgical interventions, external components such as sharp objects, e.g. scalpels, knifes or nails, and external circumstances, such as accidents, e.g. bicycle, motor vehicle, or auto accidents.

It is particularly preferred that the wound is selected from the group consisting of a topical wound, deep wound, gaping wound, stab wound, puncture wound, penetration wound, surgical incision, laceration, and cut. The term "topical wound", as used herein, refers to a wound on the tissue surface. The term "puncture wound", as used herein, refers to a wound caused by an object puncturing tissue(s), e.g. multiple (different) tissues, particularly an organ, e.g. skin, such as a nail or needle. The term "penetration wound", as used herein, refers to a wound caused by an object entering and coming out from the tissue(s), e.g. multiple (different) tissues, particularly an organ, e.g. skin, such as a nail or needle. The term "surgical incision", as used herein, refers to a wound caused by a sharp object, e.g. a scalpel or knife, during surgery.

The wound may be located in or on the surface of a tissue. The tissue may be selected form the group consisting of connective tissue, muscle tissue, nervous tissue, epithelial tissue, and combinations thereof, e.g. multiple (different) tissues. An organ, e.g. stomach, small intestine, large intestine, bowel, rectum, oesophagus, lung, spleen, brain, heart, kidney, liver, skin, glands such as lymph and thyroid glands, eye, or pancreas, is, for example, comprised of multiple (different) tissues. Thus, the wound may also be located in an organ, particularly encompassing multiple (different) tissues or tissue layers. Particularly, the wound is a skin lesion.

Preferably, the coated silk film according to the first aspect or pharmaceutical composition according to the second aspect is for the topical treatment of a wound site and/or for the treatment of an internal wound site, e.g. in case of deeper wounds or during surgical procedures.

It is preferred that the skin disease is selected from the group consisting of an infectious disease, such as herpes, an autoimmune disease, such as psoriasis, a cutaneous disease, such as acne, rosacea, dermatitis or eczema, and a gastrointestinal disease, such as dyspepsia or indigestion. It is further preferred that the skin defect is selected from the group consisting of burns, skin lesions, and wounds, such as superficial or inner wounds.

In a seventh aspect, the present invention relates to the use of the coated silk film according to the first aspect or cosmetic composition according to the third aspect for controlled and sustained release of at least one cosmetic agent. As to the preferred embodiments of the cosmetic agent, it is referred to the first aspect of the present invention.

The cosmetic agent may be released from the coated silk film or cosmetic composition comprising or consisting of the coated silk film by diffusion and/or degradation upon exposure to a physiological environment. The physiological environment may be skin. The release of the cosmetic agent from the coated silk film or cosmetic composition comprising or consisting of the coated silk film can be induced by applying the coated silk film or cosmetic composition comprising or consisting of the coated silk film onto skin.

Preferably, the release of the cosmetic agent displays relatively linear kinetics, thereby providing a constant supply of the cosmetic agent over the release period.

It is preferred that less than 20%, preferably less than 15%, more preferably less than 10%, and most preferably less than 5%, e.g. less than 20, 19, 18, 17, 16, 15, 14, 13, 12, 11, 10, 9, 8, 7, 6, or 5%, of the cosmetic agent is released, particularly into the physiological environment, within the first 24 hours.

It is, alternatively or additionally, preferred that more than 50%, preferably more than 70%, more preferably more than 80%, and most preferably 100% of the cosmetic agent is released, particularly into the physiological environment, within 36 hours. It is, alternatively or additionally, preferred that more than 50%, preferably more than 70%, more preferably more than 80%, and most preferably 100% of the cosmetic agent is released, particularly into the physiological environment, within 48 hours. It is, alternatively or additionally, preferred that more than 50%, preferably more than 70%, more preferably more than 80%, and most preferably 100% of the cosmetic agent is released, particularly into the physiological environment, within 72 hours.

It is, alternatively or additionally, more preferred that more than 50%, preferably more than 70%, more preferably more than 80%, and most preferably 100% of the cosmetic agent is released, particularly into the physiological environment, within 7 days. It is, alternatively or additionally, more preferred that more than 50%, preferably more than 70%, more preferably more than 80%, and most preferably 100% of the cosmetic agent is released, particularly into the physiological environment, within 14 days. It is, alternatively or additionally, more preferred that more than 50%, preferably more than 70%, more preferably more than 80%, and most preferably 100% of the cosmetic agent is released, particularly into the physiological environment, within 20 days. It is, alternatively or additionally, more preferred that more than 50%, preferably more than 70%, more preferably more than 80%, and most preferably 100% of the cosmetic agent is released, particularly into the physiological environment, within 30 days. It is, alternatively or additionally, more preferred that more than 50%, preferably more than 70%, more preferably more than 80%, and most preferably 100% of the cosmetic agent is released, particularly into the physiological environment, within 35 days.

It is, alternatively or additionally, even more preferred that more than 50%, preferably more than 70%, more preferably more than 80%, and most preferably 100% of the cosmetic agent is released, particularly into the physiological environment, within 5 weeks. It is, alternatively or additionally, even more preferred that more than 50%, preferably more than 70%, more preferably more than 80%, and most preferably 100% of the cosmetic agent is released, particularly into the physiological environment, within 6 weeks. It is, alternatively or additionally, even more preferred that more than 50%, preferably more than 70%, more preferably more than 80%, and most preferably 100% of the cosmetic agent is released, particularly into the physiological environment, within 7 weeks. It is, alternatively or additionally, even more preferred that more than 50%, preferably more than 70%, more preferably more than 80%, and most preferably 100% of the cosmetic agent is released, particularly into the physiological environment, within 8 weeks.

It is, alternatively or additionally, most preferred that more than 50%, preferably more than 70%, more preferably more than 80%, and most preferably 100% of the cosmetic agent is released, particularly into the physiological environment, within 3 months. It is, alternatively or additionally, most preferred that more than 50%, preferably more than 70%, more preferably more than 80%, and most preferably 100% of the cosmetic agent is released, particularly into the physiological environment, within 4 months. It is, alternatively or additionally, most preferred that more than 50%, preferably more than 70%, more preferably more than 80%, and most preferably 100% of the cosmetic agent is released, particularly into the physiological environment, within 5 months. It is, alternatively or additionally, most preferred that more than 50%, preferably more than 70%, more preferably more than 80%, and most preferably 100% of the cosmetic agent is released, particularly into the physiological environment, within 6 months. It is, alternatively or additionally, most preferred that more than 50%, preferably more than 70%, more preferably more than 80%, and most preferably 100% of the cosmetic agent is released, particularly into the physiological environment, within 7 months. It is, alternatively or additionally, most preferred that more than 50%, preferably more than 70%, more preferably more than 80%, and most preferably 100% of the cosmetic agent is released, particularly into the physiological environment, within 8 months. It is, alternatively or additionally, most preferred that more than 50%, preferably more than 70%, more preferably more than 80%, and most preferably 100% of the cosmetic agent is released, particularly into the physiological environment, within 9 months. It is, alternatively or additionally, most preferred that more than 50%, preferably more than 70%, more preferably more than 80%, and most preferably 100% of the cosmetic agent is released, particularly into the physiological environment, within 10 months.

In a further aspect, the present invention relates to an active agent delivery device or active agent depot system comprising the coated silk film according to the first aspect.

The active agent depot system comprising the coated silk film according to the first aspect may comprise conceptive agents.

In another aspect, the present invention relates to a coating comprising the coated silk film according to the first aspect.

In an eight aspect, the present invention relates to a method of producing a coated silk film comprising the steps of:
(i) providing an active agent release sheet which comprises or consists of one or more first silk film layers comprising at least one active agent, and
(ii) covering at least the side surface(s) of the active agent release sheet with one or more release modifying layers.

Due to the covering of at least the side surface(s) of the active agent release sheet with one or more release modifying layers, the coated silk film is obtained. Said coated silk film comprises or consists of an active agent release sheet which comprises or consists of one or more first silk film layers comprising at least one active agent, and one or more release modifying layers covering at least the side surface(s) of the active agent release sheet.

The active agent release sheet may comprise 1, 2, 3, or more first silk film layers. Alternatively or additionally, at least the side surface(s) of the active agent release sheet may be covered with 1, 2, 3, 4, 5, or more release modifying layers.

In one embodiment, the active agent release sheet is completely covered with one or more release modifying layers. Thus, the method of producing a coated silk film may comprise the steps of:
(i) providing an active agent release sheet which comprises or consists of one or more first silk film layers comprising at least one active agent, and
(ii) completely covering the active agent release sheet with one or more release modifying layers.

Due to the complete covering of the active agent release sheet with one or more release modifying layers, the coated silk film is obtained. Said coated silk film comprises or consists of an active agent release sheet which comprises or consists of one or more first silk film layers comprising at least one active agent, and one or more release modifying layers completely covering the active agent release sheet.

In one another embodiment, the active agent release sheet comprises one or more second silk film layers. Thus, method of producing a coated silk film may comprise the steps of:
(i) providing an active agent release sheet which comprises or consists of one or more first silk film layers comprising at least one active agent and one or more second silk film layers, and
(ii) covering at least the side surface(s) of the active agent release sheet with one or more release modifying layers.

The active agent release sheet may comprise 1, 2, 3, or more first silk film layers and/or 1, 2, 3, 4, 5, 6, 7, 8, 9, 10, 11, 12, or more second silk film layers. Alternatively or additionally, at least the side surface(s) of the active agent release sheet may be covered with 1, 2, 3, 4, 5, or more release modifying layers.

As mentioned above, in one embodiment, the active agent release sheet is completely covered with one or more release modifying layers. Thus, the method of producing a coated silk film may comprise the steps of:
(i) providing an active agent release sheet which comprises or consists of one or more first silk film layers comprising at least one active agent and one or more second silk film layers, and (ii) completely covering the active agent release sheet with one or more release modifying layers.

In one preferred embodiment, the active agent release sheet comprises or consists of (a) first silk film layer(s) comprising at least one active agent which is (are) flanked by second silk film layers. In other word, the first silk film layer(s) comprising at least one active agent is (are) sandwiched or embedded between second silk film layers.

It one another preferred embodiment, the one or more first silk film layers and/or the one or more second silk film layers comprise at least one plasticizer.

In one further preferred embodiment, the active agent release sheet comprises plasticizer containing first and/or second silk film layers and plasticizer free first and/or second silk film layers in alteration. For example, the active agent release sheet may comprise one plasticizer containing first silk film layer and one plasticizer free second silk film layer. Further, the active agent release sheet may comprise one plasticizer containing first silk film layer and two plasticizer free second silk film layers, wherein both plasticizer free second silk film layers are attached to the plasticizer containing first silk film layer, thereby forming a sandwich structure. Furthermore, the active agent release sheet may comprise one plasticizer containing first silk film layer, one or more plasticizer containing second silk film layers and one or more plasticizer free second silk film layers, wherein the plasticizer containing silk film layers and plasticizer free silk film layers are arranged alternately. The active agent release sheet may have a structure as described in FIGS. 4A and 5A. The advantages of the use of plasticizers are described with respect to the first aspect of the present invention.

Preferably, the one or more release modifying layers does not contain a plasticizer. In other words, it is preferred that the one or more release modifying layers are plasticizer free.

It is preferred that the amount of the plasticizer in the one or more first silk film layers and/or one or more second silk film layers is of between 0.1% (w/w) and 70% (w/w), more preferably of between 5% (w/w) and 70% (w/w) or of between 15% (w/w) and 70% (w/w), even more preferably of between 15% (w/w) and 55% (w/w) or of between 30% (w/w) and 55% (w/w), and most preferably of 30% (w/w). It is further preferred that the amount of the plasticizer in the one or more first silk film layers and/or one or more second silk film layers is of at least 0.1, 1, 5, 10, 15, 20, 25, 30, 35, 40, 45, 50, 55, 60, 65, or 70% (w/w).

Preferred plasticizers are selected from glycerol, 2-pyrrolidone, polyethylenglycol (PEG), polyvinylalcohol (PVA), poloxamer, polyvinylpirrolidone (PVP), polyacrylic acid, polyorthoester, gelatine, collagen, cellulose, cellulose derivates, and sorbitol. More preferred plasticizers are selected from glycerol and 2-pyrrolidone.

It is further preferred that the active agent has a molecular weight of between 50 Da and 300 kDa, preferably of between 80 Da and 250 kDa, more preferably of between 100 Da and 200 kDa, and most preferably of between 150 Da and 150 kDa. The active agent may further have a molecular weight of between 50 Da and <50 kDa or a molecular weight of between 50 kDa and 150 kDa.

Preferred active agents are selected from the group consisting of a biological agent, a pharmaceutical agent, a cosmetic agent, a nutrient, and a dietary supplement. As to the preferred embodiments of a biological agent, pharmaceutical agent, cosmetic agent, nutrient, or dietary supplement, it is referred to the first aspect of the present invention.

The active agent may be positively or negatively charged. The active agent may also be electroneutral. Preferably, the active agent is positively or negatively charged. The silk film comprising or consisting of an active agent release sheet may have a positive or negative net charge. Thus, it is preferred that the active agent comprised in the first silk film layer(s) of the active agent release sheet is positively charged, if the silk film has a negative net charge. It is further preferred that the active agent comprised in the first silk film layer(s) of the active agent release sheet is negatively charged, if the silk film has a positive net charge.

The one or more release modifying layers comprise or consist of a release modifying material (e.g. a silk material). In one embodiment, the one or more release modifying layers comprise or consist of at least one release modifying agent. It is preferred that the release modifying agent is selected from the group consisting of a (i) silk polypeptide, (ii) polyester, preferably polylactide, polyglycolide, polylactic polyglycolic copolymer (PLGA), and blend of polylactic polyglycolic copolymer (PLGA) and polylactide, (iii) polyether, preferably polycaprolactone (PCL), (iv) polyanhydride, (v) polyalkylcyanoacrylate, preferably n-butyl cyanoacrylate, (vi) polyacrylamide, (vii) polyurethane, and (viii) polyvinylpirrolidone (PVP). It is more preferred that the release modifying agent is a silk polypeptide.

The silk film, particularly the one or more first silk film layers and/or the one or more second silk film layers, comprise a silk material. In one embodiment, the silk film, particularly the one or more first silk film layers and/or the one or more second silk film layers, comprise at least one silk polypeptide.

It is preferred that the silk polypeptide is a recombinant silk polypeptide. It is further preferred that the silk polypeptide is a (recombinant) spider silk polypeptide, more preferably a (recombinant) major ampullate silk polypeptide such as a (recombinant) dragline silk polypeptide, a (recombinant) minor ampullate silk polypeptide, or a (recombinant) flagelliform silk polypeptide of an orb-web spider (e.g. Araneidae or Araneoids), an (recombinant) insect silk polypeptide, a (recombinant) mussel byssus silk polypeptide, or a mixture thereof. The orb-web spider may be selected from the group consisting of *Araneus diadematus, Nephila clavipes*, and *Latrodectus hesperus*. The insect silk polypeptide may be of Lepidoptera, particularly Bombycidae such as *Bombyx mori*. The insect silk polypeptide may also be of Hymenoptera, particularly Apoidea such as Anthophila.

It is, alternatively or additionally, preferred that the silk polypeptide comprises or consists of at least two repetitive units.

Preferably, the silk polypeptide comprises or consists of at least two repetitive units each comprising at least one, preferably one, consensus sequence selected from the group consisting of:
(i) GPGXX (SEQ ID NO: 3), wherein X is any amino acid, preferably in each case independently selected from A, S, G, Y, P, and Q;
(ii) GGX, wherein X is any amino acid, preferably in each case independently selected from Y, P, R, S, A, T, N and Q, more preferably in each case independently selected from Y, P and Q;
(iii) $A_x$, wherein x is an integer from 5 to 10;

```
(iv)     GGRPSDTYG;    (SEQ ID NO: 18)
and
(v)      GGRPSSSYG.    (SEQ ID NO: 19)
```

The above mentioned silk polypeptide preferably has a molecular weight of at least 5 kDa, e.g. of at least 5, 6, 7, 8, 9, 10, 11, 12, 13, 14, 15, 16, 17, 18, 19, or 20 kDa.

It is preferred that the repetitive units are independently selected from module A (SEQ ID NO: 20) or variants thereof, module C (SEQ ID NO: 21) or variants thereof, module Q (SEQ ID NO: 22) or variants thereof, module S (SEQ ID NO: 23) or variants thereof, and module R (SEQ ID NO: 24) or variants thereof.

It is further preferred that the repetitive units are independently selected from module $A^C$ (SEQ ID NO: 25), module $A^K$ (SEQ ID NO: 26), module $C^C$ (SEQ ID NO: 27), module $C^{K1}$ (SEQ ID NO: 28), module $C^{K2}$ (SEQ ID NO: 29), module $C^{KC}$ (SEQ ID NO: 30), and module $C^{Kappa}$ (SEQ ID NO: 43).

It is more preferred that the repetitive units are independently selected from module A (SEQ ID NO: 20) or variants thereof, module C (SEQ ID NO: 21) or variants thereof, module Q (SEQ ID NO: 22) or variants thereof, module S (SEQ ID NO: 23) or variants thereof, module R (SEQ ID NO: 24) or variants thereof, module $A^C$ (SEQ ID NO: 25), module $A^K$ (SEQ ID NO: 26), module $C^C$ (SEQ ID NO: 27), module $C^{K1}$ (SEQ ID NO: 28), module $C^{K2}$ (SEQ ID NO: 29), module $C^{KC}$ (SEQ ID NO: 30), and module $C^{Kappa}$ (SEQ ID NO: 43).

The silk polypeptide can further comprise at least one non-repetitive (NR) unit, e.g. at least 1, 2, 3, 4, 5, 6, or more NR unit(s), preferably one NR unit. It is preferred that the non-repetitive (NR) unit is selected from NR3 (SEQ ID NO: 31) or variants thereof, NR4 (SEQ ID NO: 32) or variants thereof, NR5 (SEQ ID NO: 33) or variants thereof, or NR6 (SEQ ID NO: 34) or variants thereof.

It is even more preferred that the silk polypeptide is selected from the group consisting of ADF-3 (SEQ ID NO: 1) or variants thereof, ADF-4 (SEQ ID NO: 2) or variants thereof, MaSp I (SEQ ID NO: 35) or variants thereof, MaSp II (SEQ ID NO: 36) or variants thereof, $(C)_m$, $(C)_mNR_z$, $NR_z(C)_m$, $(C^{Kappa})_m$, $(C^{Kappa})_mNR_z$, $NR_z(C^{Kappa})_m$, $(AQ)_n$, $(AQ)_n NR_z$, $NR_z(AQ)_n$, $(QAQ)_o$, $NR_z(QAQ)_o$, and $(QAQ)_oNR_z$, wherein m is an integer of 4 to 64, i.e. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, n is an integer of 6 to 40, i.e. 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, o is an integer of 8 to 40, i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, z is an integer of 1 to 3, i.e. 1, 2, or 3, and NR is in each case independently a non-repetitive unit, preferably a NR3, NR4, NR5, or NR6 non-repetitive unit or a variant thereof.

It is most preferred that the silk polypeptide is selected from the group consisting of $C_{16}$, $C_{16}NR4$, $NR4C_{16}$, $C_{16}NR3$, $NR3C_{16}$, $NR4C_{16}NR4$, $NR3C_{16}NR3$, $NR4C_{16}NR3$, $NR3C_{16}NR4$, $C_{32}$, $C_{32}NR4$, $NR4C_{32}$, $C_{32}NR3$, $NR3C_{32}NR4C_{32}NR4$, $NR3C_{32}NR3$, $NR4C_{32}NR3$, $NR3C_{32}NR4$, $C^{Kappa}{}_{16}$, $C^{Kappa}{}_{16}NR4$, $NR4C^{Kappa}{}_{16}$, $C^{Kappa}{}_{16}NR3$, $NR3C^{Kappa}{}_{16}$, $NR4C^{Kappa}{}_{16}NR4$, $NR3C^{Kappa}{}_{16}NR3$, $NR4C^{Kappa}{}_{16}NR3$, $NR3C^{Kappa}{}_{16}NR4$, $(AQ)_{12}$, $(AQ)_{12}NR3$, $NR3(AQ)_{12}$, $(AQ)_{12}NR4$, $NR4(AQ)_{12}$, $NR3(AQ)_{12}NR3$, $NR4(AQ)_{12}NR4$, $NR3(AQ)_{12}NR4$, $NR4(AQ)_{12}NR3$, $(AQ)_{24}$, $(AQ)_{24}NR3$, $NR3(AQ)_{24}$, $(AQ)_{24}NR4$, $NR4(AQ)_{24}$, $NR3(AQ)_{24}NR3$, $NR4(AQ)_{24}NR4$, $NR3(AQ)_{24}NR4$, $NR4(AQ)_{24}NR3$, $(QAQ)_8$, and $(QAQ)_{16}$.

The silk polypeptide may further comprise an amino terminal and/or a carboxy terminal TAG selected from the group consisting of (i) $TAG^{CYS1}$ consisting of the amino acid sequence GCGGGGGGSGGGG (SEQ ID NO: 37), (ii) $TAG^{CYS2}$ consisting of the amino acid sequence GCGGGGGG (SEQ ID NO: 38), (iii) $TAG^{CYS3}$ consisting of the amino acid sequence GCGGSGGGGSGGGG (SEQ ID NO: 39), (iv) $TAG^{LYS1}$ consisting of the amino acid sequence GKGGGGGGSGGGG (SEQ ID NO: 41), and (v) $TAG^{LYS2}$ consisting of the amino acid sequence GKGGGGGG (SEQ ID NO: 42). Said amino terminal and/or a carboxy terminal TAGs allow the coupling (by forming covalent bounds) of active agents to the silk polypeptide and, thus, to the silk film.

As to further preferred embodiments of the silk polypeptide, it is referred to the first aspect of the present invention.

In one embodiment, the one or more first silk film layers have a thickness of at least 0.1, 0.5, 1, 2, 3, 4, 5, 10, 15, 20, 25, 30, 35, 40, 45, 50, 60, 70, 80, 90, 100, 110, 120, 130, 140, 150, 160, 170, 180, 190, 200, 300, 400, 500, 600, 700, 800, 900 µm, 1, 2, 3, 4, 5, 6, 7, 8, 9 mm, or 1 cm. In one further embodiment, the one or more first silk film layers have a thickness of between 0.1 µm and 1 cm, preferably of between 1 µm and 5 mm or of between 1 µm and 1 mm, more preferably of between 1 µm and 200 µm or of between 1 µm and 100 µm, and most preferably of between 1 µm and 50 µm or of between 1 µm and 40 µm. In this respect, it should be noted that the thickness of the first silk film layers may be varied depending on the amount of the active agent to be incorporated. For example, an increased thickness of the first silk film layers allows the incorporation of a higher amount of the active agent.

In one another embodiment, the one or more release modifying layers have a thickness of at least 0.05, 0.1, 0.5, 1, 2, 3, 4, 5, 10, 15, 20, 25, 30, 35, 40, 45, 50, 60, 70, 80, 90, 100, 110, 120, 130, 140, 150, 160, 170, 180, 190, 200, 300, 400, or 500 µm. In one further embodiment, the one or more release modifying layers have a thickness of between 0.05 µm and 500 µm or of between 0.1 µm and 500 µm, preferably of between 0.5 µm and 200 µm or of between 0.5 µm and 100 µm, even more preferably of between 0.5 µm and 80 µm or of between 0.5 µm and 50 µm, and most preferably of between 0.5 µm and 40 µm or of between 0.5 µm and 20 µm. In this respect, it should be noted that the thickness of the release modifying layers may be varied depending on the desired release of the active agent. For example, an increased thickness of the release modifying layers allows a slower release of the active agent.

In one alternative or additional embodiment, the one or more second silk film layers have a thickness of at least 0.1, 0.5, 1, 2, 3, 4, 5, 10, 15, 20, 25, 30, 35, 40, 45, 50, 60, 70, 80, 90, 100, 110, 120, 130, 140, 150, 160, 170, 180, 190, 200, 300, 400, 500, 600, 700, 800, 900 µm, 1, 2, 3, 4, 5, 6, 7, 8, 9 mm, or 1 cm. In one further embodiment, the one or more second silk film layers have a thickness of between 0.1 µm and 1 cm, preferably of between 1 µm and 5 mm or of between 1 µm and 1 mm, more preferably of between 1 µm and 200 µm or of between 1 µm and 100 µm, and most preferably of between 1 µm and 50 µm or of between 1 µm and 40 µm. In this respect, it should be noted that the thickness of the second silk film layers may be varied depending on the desired retardation of the active agent. For example, an increased thickness of the second silk film layers allows a better retardation of release of the active agent.

It is preferred that the method further comprises the step of drying the one or more release modifying layers. The drying can be carried out, for example, by drying in the air, baking, using a heat chamber, a vacuum chamber, laminar flow (e.g. of a gas such as nitrogen or carbon dioxide), radiation, or a fan (at low temperatures, at room temperature or at elevated temperatures).

It is further preferred that the method further comprises the step of applying pressure to the one or more release modifying layers. The inventors of the present invention found that the application of pressure to the one or more release modifying layers increases and improves the connection of the release modifying layer(s) to the active agent release sheet of the silk film, which, in turn, results in an increase of the packing density of the coated silk film. The inventors of the present invention further found that an increased packing density of the coated silk film has an influence on the release of active agents from said film. Particularly, an increased packing density of the coated silk film reduces the release of active agents from said film. Thus, the application of pressure to the release modifying layer(s) or not and, if yes, the variation of the pressure applied to the release modifying layer(s) allows to adapt/change the release profile of the active agents from the coated silk film. The application of pressure to the one or more release modifying layer(s) may further improve, particularly increase, the film elongation. Preferably, the pressure applied to the one or more release modifying layers corresponds to a weight force of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2 t/m$^2$. A weight force of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2 t/m$^2$ corresponds to 1, 2, 3, 4, 5, 6, 7, 8, 9, 10, 11, 12, 13, 14, 15, 16, 17, 18, 19, or 20 kN/m$^2$, respectively.

It is, alternatively or additionally, also preferred that the method further comprises the step of applying water vapour to the one or more release modifying layers. The inventors of the present invention found that the application of water vapour allows the transformation of a water-soluble coated silk film into a water-insoluble coated silk film. Thus, a coated silk film, which initially was water-soluble, can be processed with water vapour leading to water-insolubility. The conversion of a water-soluble coated silk film into a water-insoluble coated silk film is attributable to, on a structural basis, an increased β-sheet structure content.

It is preferred that the water vapour has a temperature of between 1° C. and 121° C., preferably of between 1° C. and 80° C., more preferably of between 4° C. and 50° C., even more preferably of between 15° C. and 40° C., and most preferably of between of between 19° C. or 20° C. (room temperature) and 35° C., e.g. a temperature of 19, 20, 21, 22, 23, 24, 25, 26, 27, 28, 29, 30, 31, 32, 33, 34, or 35° C. It is, alternatively or additionally, preferred that the water vapour has a relative humidity of between 50% and 100%, preferably of between 50% and 90%, more preferably of between 60% and 90%, and most preferably of between 70% and 80%, e.g. a relative humidity of 70, 71, 72, 73, 74, 75, 76, 77, 78, 79, or 80%.

Thus, the method may further comprise the steps of (i) drying the one or more release modifying layers and applying pressure to the one or more release modifying layers, (ii) drying the one or more release modifying layers and applying water vapour to the one or more release modifying layers, (iii) drying the one or more release modifying layers, applying pressure to the one or more release modifying layers and applying water vapour to the one or more release modifying layers, or (iv) drying the one or more release modifying layers, applying water vapour to the one or more release modifying layers, and applying pressure to the one or more release modifying layers.

In one embodiment, the active agent release sheet is at least at its side surface(s) covered with one release modifying layer by
(i) immersing the active agent release sheet at least at its side surface(s) into an aqueous solution or dispersion comprising or consisting of a release modifying material (e.g. at least one release modifying agent), or spraying an aqueous solution or dispersion comprising or consisting of a release modifying material (e.g. at least one release modifying agent) on at least the side surface(s) of the active agent release sheet,
(ii) forming one release modifying layer which covers at least the side surface(s) of the active agent release sheet, particularly by drying the aqueous solution or dispersion comprising or consisting of a release modifying material (e.g. at least one release modifying agent), and
(iii) optionally applying pressure and/or water vapour to the one release modifying layer.

Preferably, steps (i) and (ii) and optionally step (iii) are repeated one or more times to form further release modifying layers on the release modifying layer formed in step (ii).

As mentioned above, in one embodiment, the active agent release sheet is completely covered with one or more release modifying layers. In this case, the active agent release sheet is completely covered with one release modifying layer by
(i) completely immersing the active agent release sheet into an aqueous solution or dispersion comprising or consisting of a release modifying material (e.g. at least one release modifying agent), or spraying an aqueous solution or dispersion comprising or consisting of a release modifying material (e.g. at least one release modifying agent) on the active agent release sheet,
(ii) forming one release modifying layer which completely covers the active agent release sheet, particularly by drying the aqueous solution or dispersion comprising or consisting of a release modifying material (e.g. at least one release modifying agent), and
(iii) optionally applying pressure and/or water vapour to the one release modifying layer.

Preferably, steps (i) and (ii) and optionally step (iii) are repeated one or more times to form further release modifying layers on the release modifying layer formed in step (ii).

The drying can be carried out, for example, by drying in the air, baking, using a heat chamber, a vacuum chamber, laminar flow (e.g. of a gas such as nitrogen or carbon dioxide), radiation, or a fan (at low temperatures, at room temperature or at elevated temperatures).

If pressure is applied to the release modifying layer(s), it is preferred that the pressure corresponds to a weight force of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2 t/m$^2$. A weight force of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2 t/m$^2$ corresponds to 1, 2, 3, 4, 5, 6, 7, 8, 9, 10, 11, 12, 13, 14, 15, 16, 17, 18, 19, or 20 kN/m$^2$, respectively.

If water vapour is applied to the release modifying layer(s), it is further preferred that the water vapour has a temperature of between 1° C. and 121° C., preferably of between 1° C. and 80° C., more preferably of between 4° C. and 50° C., even more preferably of between 15° C. and 40° C., and most preferably of between of between 19° C. or 20° C. (room temperature) and 35° C., e.g. a temperature of 19, 20, 21, 22, 23, 24, 25, 26, 27, 28, 29, 30, 31, 32, 33, 34, or 35° C. It is, alternatively or additionally, also preferred that the water vapour has a relative humidity of between 50% and 100%, preferably of between 50% and 90%, more preferably of between 60% and 90%, and most preferably of between 70% and 80%, e.g. a relative humidity of 70, 71, 72, 73, 74, 75, 76, 77, 78, 79, or 80%.

It is preferred that the release modifying agent is comprised in the aqueous solution or dispersion in a concentration of between 0.5 mg/ml and 15 mg/ml, preferably in a concentration of between 1 mg/ml and 10 mg/ml, and more preferably in a concentration of between 1 mg/ml and 5 mg/ml. Preferably, the release modifying agent is a silk polypeptide.

It is further preferred that the aqueous solution or dispersion mentioned above comprises at least one plasticizer. Preferably, the plasticizer is comprised in the aqueous solution or dispersion in a concentration of between 0.1% (w/v) and 10% (w/v), more preferably of between 0.5% (w/v) and 5% (w/v) or between 1% (w/v) and 5% (w/v), even more preferably of between 1% (w/v) and 3% (w/v) or between 1% (w/v) and 2% (w/v), and most preferably of between 3% (w/v). Preferred plasticizers are selected from glycerol, 2-pyrrolidone, polyethylenglycol (PEG), polyvinylalcohol (PVA), poloxamer, polyvinylpirrolidone (PVP), polyacrylic acid, polyorthoester, gelatine, collagen, cellulose, cellulose derivates, and sorbitol. More preferred plasticizers are selected from glycerol and 2-pyrrolidone.

The aqueous solution or dispersion may be a buffered aqueous solution or dispersion, preferably TRIS buffer-HCl (pH 8), particularly 5 mM TRIS puffer-HCl (pH 8).

The active agent release sheet of the silk film provided in step (i) of the method of producing a coated silk film may be produced in several ways which are described below: In one embodiment, the active agent release sheet is produced by the steps of:
(a) providing an aqueous solution or dispersion comprising or consisting of a silk material (e.g. at least one silk polypeptide) and at least one active agent, and
(b) forming a first silk film layer comprising at least one active agent from the aqueous solution or dispersion comprising or consisting of a silk material (e.g. at least one silk polypeptide) and at least one active agent, particularly by applying the aqueous solution or dispersion comprising or consisting of a silk material (e.g. at least one silk polypeptide) and at least one active agent on a support material and drying said aqueous solution or dispersion, and
(c) optionally applying water vapour to the first silk film layer.

In one embodiment, the method of producing the active agent release sheet further comprises the steps of:
(d) providing an aqueous solution or dispersion comprising or consisting of a silk material (e.g. at least one silk polypeptide) and at least one active agent, or providing an aqueous solution or dispersion comprising or consisting of a silk material (e.g. at least one silk polypeptide),
(e) forming a further first silk film layer comprising or consisting of at least one active agent from the aqueous solution or dispersion comprising or consisting of a silk material (e.g. at least one silk polypeptide) and at least one active agent on the first silk film layer formed in step (b), particularly by applying the aqueous solution or dispersion comprising or consisting of a silk material (e.g. at least one silk polypeptide) and at least one active agent on said first silk film layer and drying said aqueous solution or dispersion, or forming a second silk film layer from the aqueous solution or dispersion comprising or consisting of a silk material (e.g. at least one silk polypeptide) on the first silk film layer formed in step (b), particularly by applying the aqueous solution or dispersion comprising or consisting of a silk material (e.g. at least one silk polypeptide) on said first silk film layer and drying said aqueous solution or dispersion, and
(f) optionally applying pressure and/or water vapour to the first silk film layer or second silk film layer.

Preferably, steps (d) and (e) and optionally step (f) are repeated one or more times (e.g. 1, 2, 3 4, 5, 6, 7, 8, 9, 10, or more times) to form further first and/or second silk film layers on the first silk film layer formed in step (b).

In one another embodiment, the active agent release sheet is produced by the steps of:
(a) providing an aqueous solution or dispersion comprising or consisting of a silk material (e.g. at least one silk polypeptide), and
(b) forming a second silk film layer from the aqueous solution or dispersion comprising or consisting of a silk material (e.g. at least one silk polypeptide), particularly by applying the aqueous solution or dispersion comprising or consisting of a silk material (e.g. at least one silk polypeptide) on a support material and drying said aqueous solution or dispersion, and
(c) optionally applying water vapour to the second silk film layer.

In one embodiment, the method of producing the active agent release sheet further comprises the steps of:
(d) providing an aqueous solution or dispersion comprising or consisting of a silk material (e.g. at least one silk polypeptide) and at least one active agent, or providing an aqueous solution or dispersion comprising or consisting of a silk material (e.g. at least one silk polypeptide),
(e) forming a first silk film layer comprising or consisting of at least one active agent from the aqueous solution or dispersion comprising or consisting of a silk material (e.g. at least one silk polypeptide) and at least one active agent on the second silk film layer formed in step (b), particularly by applying the aqueous solution or dispersion comprising or consisting of a silk material (e.g. at least one silk polypeptide) and at least one active agent on said second silk film layer and drying said aqueous solution or dispersion, or forming a further second silk film layer from the aqueous solution or dispersion comprising or consisting of a silk material (e.g. at least one silk polypeptide) on the second silk film layer formed in step (b), particularly by applying the aqueous solution or dispersion comprising or consisting of a silk material (e.g. at least one silk polypeptide) on said second silk film layer and drying said aqueous solution or dispersion, and
(f) optionally applying pressure and/or water vapour to the first silk film layer or second silk film layer.

Preferably, steps (d) and (e) and optionally step (f) are repeated one or more times (e.g. 1, 2, 3 4, 5, 6, 7, 8, 9, 10, or more times) to form further first and/or second silk film layers on the second silk film layer formed in step (b).

In this respect, it should be noted that any variations and arrangements of silk film layers are possible, provided that the active agent release sheet comprises at least one first silk film layer.

The support material may be any solid support material such as polystyrene, glass, polytetrafluoroethylene, or silane. The application of the aqueous solution or dispersion comprising or consisting of a silk material (e.g. at least one silk polypeptide) and at least one active agent or the aqueous solution or dispersion comprising or consisting of a silk material (e.g. at least one silk polypeptide) may take place by casting, spraying, or dropping said aqueous solution or dispersion on the support material or on the already existing/formed first and/or second silk film layers.

It is preferred to produce with the above described methods an active agent release sheet which comprises or consists of (a) first silk film layer(s) comprising at least one active agent which is (are) flanked by second silk film layers. In other word, the first silk film layer(s) comprising at least one active agent is (are) sandwiched or embedded between second silk film layers.

The technique in which the at least one active agent is directly comprised in the aqueous solution or dispersion can be designated as "direct loading technique".

In one alternative embodiment, the active agent release sheet is produced by the steps of:
(a) providing an aqueous solution or dispersion comprising or consisting of a silk material (e.g. at least one silk polypeptide),
(b) forming a silk film layer from the aqueous solution or dispersion comprising or consisting of a silk material (e.g. at least one silk polypeptide), particularly by applying the aqueous solution or dispersion comprising or consisting of a silk material (e.g. at least one silk polypeptide) on a support material and drying said aqueous solution or dispersion, and
(c) loading at least one active agent into and/or onto the silk film layer, thereby producing a first silk film layer comprising or consisting of at least one active agent, and
(d) optionally applying water vapour to the first silk film layer.

In one embodiment, the method of producing the active agent release sheet further comprises the steps of:
(e) providing an aqueous solution or dispersion comprising or consisting of a silk material (e.g. at least one silk polypeptide),
(f) forming a second silk film layer from the aqueous solution or dispersion comprising or consisting of a silk material (e.g. at least one silk polypeptide) on the first silk film layer produced in step (c), particularly by applying the aqueous solution or dispersion comprising or consisting of a silk material (e.g. at least one silk polypeptide) on said first silk film layer and drying said aqueous solution or dispersion, and
(g) optionally applying pressure and/or water vapour to the second silk film layer.

Preferably, steps (e) and (f) and optionally step (g) are repeated one or more times to form further second silk film layers on the first silk film layer produced in step (c).

The loading of the at least one active agent into the silk film layer may take place by introducing/placing the silk film layer into an aqueous solution or dispersion comprising the at least one active agent.

The technique in which the at least one active agent is loaded into the (already produced/existing) silk film (layer) can be designated as "remote loading technique".

The support material may be any solid support material such as polystyrene, glass, polytetrafluoroethylene, or silane. The application of the aqueous solution or dispersion comprising or consisting of a silk material (e.g. at least one silk polypeptide) may take place by casting, spraying, or dropping said aqueous solution or dispersion on the support material or on the already existing/formed first and/or second silk film layers.

It is preferred to produce with the above described method an active agent release sheet which comprises or consists of (a) first silk film layer(s) comprising at least one active agent which is (are) flanked by second silk film layers. In other word, the first silk film layer(s) comprising at least one active agent is (are) sandwiched or embedded between second silk film layers.

Within the context of the present invention, the loading and the loading efficiency of the silk film, particularly of the active agent release sheet of the silk film, can be calculated on basis of the following equations:

$$\text{loading (w/w \%)} = \frac{\text{amount active agent in the silk film}}{\text{amount of the silk film}} \times 100$$

For example the "loading" is calculated to be 80% with the following data: amount of active agent non-covalently bound to the surface of the silk film and/or incorporated into the silk film: 0.8 g, amount of active agent initially added: 1.0 g.

$$\text{loading (w/w \%)} = \frac{0.8 \text{ g}}{1.0 \text{ g}} \times 100 = 80\%$$

$$\text{loading efficiency (w/w \%)} = \frac{\text{amount of active agent in the silk film}}{\text{active agent in the aqueous solution/dispersion}} \times 100$$

For example, the "encapsulation efficiency" is calculated to be 66% with the following data: amount of active agent non-covalently bound to the surface of the silk film and/or incorporated into the silk film: 0.1 g, amount of active compound initially added: 0.15 g.

$$\text{loading efficiency (w/w \%)} = \frac{0.1 \text{ g}}{0.15 \text{ g}} \times 100 = 66\%$$

The loading and the loading efficiency of the silk film, particularly of the active agent release sheet of the silk film, can be determined using UV-Vis spectroscopy.

In one another alternative embodiment, the active agent release sheet is produced by the steps of:
(a) providing two or more first silk film layers comprising or consisting of at least one active agent and preferably one or more second silk film layers, or providing one or more first silk film layers comprising or consisting of at least one active agent and one or more second silk film layers,
(b) stacking up the two or more first silk layers comprising or consisting of at least one active agent and preferably the one or more second silk film layers, or the one or more first silk film layer comprising or consisting of at least one active agent and the one or more second silk film layers, and
(c) applying pressure to the stacked layers in order to combine or connect said layers with each other.

It is preferred that the first silk film layer used above is produced by:
providing an aqueous solution or dispersion comprising or consisting of a silk material (e.g. at least one silk polypeptide) and at least one active agent, forming a first silk film layer comprising or consisting of at least one active agent from the aqueous solution or dispersion comprising or consisting of a silk material (e.g. at least one silk polypeptide) and at least one active agent, particularly by applying the aqueous solution or dispersion comprising or consisting of a silk material (e.g. at least one silk polypeptide) and at least one active agent on a support material and drying said aqueous solution or dispersion, and optionally applying water vapour to the first silk film layer.

Alternatively, it is preferred that the first silk film layer is produced by:
providing an aqueous solution or dispersion comprising or consisting of a silk material (e.g. at least one silk polypeptide), forming a silk film layer from the aqueous solution or dispersion comprising or consisting of a silk material (e.g. at least one silk polypeptide), particularly by applying the aqueous solution or dispersion comprising or consisting of a silk material (e.g. at least one silk polypeptide) on a support material and drying said aqueous solution or dispersion, loading at least one active agent into and/or onto the silk film layer, thereby producing a first silk film layer comprising or consisting of at least one active agent, and optionally applying water vapour to the first silk film layer.

It is preferred that the second silk film layer is produced by:
providing an aqueous solution or dispersion comprising or consisting of a silk material (e.g. at least one silk polypeptide), forming a second silk film layer from the aqueous solution or dispersion comprising or consisting of a silk material (e.g. at least one silk polypeptide), particularly by applying the aqueous solution or dispersion comprising or consisting of a silk material (e.g. at least one silk polypeptide) on a support material and drying said aqueous solution or dispersion, and optionally applying water vapour to the second silk film layer.

The application of the aqueous solution or dispersion comprising or consisting of a silk material (e.g. at least one silk polypeptide) and at least one active agent or the aqueous solution or dispersion comprising or consisting of a silk material (e.g. at least one silk polypeptide) may take place by casting, spraying, or dropping said aqueous solution or dispersion on a support material. The support material may be any solid support material such as polystyrene, glass, polytetrafluoroethylene, or silane.

It is preferred to produce with the above described method an active agent release sheet which comprises or consists of (a) first silk film layer(s) comprising at least one active agent which is (are) flanked by second silk film layers. In other word, the first silk film layer(s) comprising at least one active agent is (are) sandwiched or embedded between second silk film layers.

The drying can be carried out, for example, by drying in the air, baking, using a heat chamber, a vacuum chamber, laminar flow (e.g. of a gas such as nitrogen or carbon dioxide), radiation, or a fan (at low temperatures, at room temperature or at elevated temperatures).

If pressure is applied to the first and/or second silk film layer(s) or to the stacked first and/or second silk film layers, it is preferred that the pressure corresponds to a weight force of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2 t/m². A weight force of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2 t/m² corresponds to 1, 2, 3, 4, 5, 6, 7, 8, 9, 10, 11, 12, 13, 14, 15, 16, 17, 18, 19, or 20 kN/m², respectively.

If water vapour is applied to the first and/or second silk film layer(s) or to the silk film layer, it is further preferred that the water vapour has a temperature of between 1° C. and 121° C., preferably of between 1° C. and 80° C., more preferably of between 4° C. and 50° C., even more preferably of between 15° C. and 40° C., and most preferably of between of between 19° C. or 20° C. (room temperature) and 35° C., e.g. a temperature of 19, 20, 21, 22, 23, 24, 25, 26, 27, 28, 29, 30, 31, 32, 33, 34, or 35°. It is, alternatively or additionally, also preferred that the water vapour has a relative humidity of between 50% and 100%, preferably of between 50% and 90%, more preferably of between 60% and 90%, and most preferably of between 70% and 80%, e.g. a relative humidity of 70, 71, 72, 73, 74, 75, 76, 77, 78, 79, or 80%.

It is preferred that the aqueous solution or dispersion mentioned above comprises at least one plasticizer. Preferably, the plasticizer is comprised in the aqueous solution or dispersion in a concentration of between 0.1% (w/v) and 10% (w/v), more preferably of between 0.5% (w/v) and 5% (w/v) or between 1% (w/v) and 5% (w/v), even more preferably of between 1% (w/v) and 3% (w/v) or between 1% (w/v) and 2% (w/v), and most preferably of between 3% (w/v). Preferred plasticizers are selected from glycerol, 2-pyrrolidone, polyethylenglycol (PEG), polyvinylalcohol (PVA), poloxamer, polyvinylpirrolidone (PVP), polyacrylic acid, polyorthoester, gelatine, collagen, cellulose, cellulose derivates, and sorbitol. More preferred plasticizers are selected from glycerol and 2-pyrrolidone.

The aqueous solution or dispersion may be a buffered aqueous solution or dispersion, preferably TRIS buffer-HCl (pH 8), particularly 5 mM TRIS puffer-HCl (pH 8).

It is further preferred that the concentration of the at least one silk polypeptide in the aqueous solution is of between 0.1% (w/v) and 30% (w/v), preferably of between 0.5% (w/v) and 20% (w/v), and more preferably of between 1% (w/v) and 10% (w/v).

It is, alternatively or additionally, also preferred that the active agent is comprised in the aqueous solution or dispersion in a concentration of between 0.5 mg/ml and 15 mg/ml, preferably in a concentration of between 1 mg/ml and 10 mg/ml, and more preferably in a concentration of between 1 mg/ml and 5 mg/ml.

In this respect, the following should be noted: The inventors of the present invention observed that the use of an aqueous solution or dispersion having a pH that is lower than the pI of the silk material (e.g. at least one silk polypeptide) used for silk film formation results in a positively charged silk film. In this respect, it is preferred that the active agent added to the aqueous solution or dispersion is negatively charged at the pH of the aqueous solution or dispersion in order to achieve effective incorporation of the active agent into the silk film. Further, the inventors of the present invention observed that the use of an aqueous solution or dispersion having a pH that is higher than the pI of the silk material (e.g. at least one silk polypeptide) used for silk film formation results in a negatively charged film. In this respect, it is preferred that the active agent added to the aqueous solution or dispersion is positively charged at the pH of the aqueous solution or dispersion in order to achieve effective incorporation of the active agent into the silk film. The incorporation of the active agent into the silk film preferably arises from electrostatic and/or hydrophobic interactions between the silk material (e.g. at least one silk polypeptide) and the active agent.

For example, the spider silk polypeptide $C_{16}$ has a pI of 3.48 and the spider silk polypeptide $C^{Kappa}_{16}$ has a pI of 9.7. Thus, the use of an aqueous solution or dispersion comprising the spider silk polypeptide $C_{16}$ and having a pH of <3.48 results in a positively charged spider silk polypeptide $C_{16}$ film. Accordingly, the active agent added to this aqueous solution or dispersion should be negatively charged at this pH in order achieve effective loading of the silk film. In contrast thereto, the use of an aqueous solution or dispersion comprising the spider silk polypeptide $C_{16}$ and having a pH of >3.48 results in a negatively charged spider silk polypeptide $C_{16}$ film. Accordingly, the active agent added to this aqueous solution or dispersion should be positively charged at this pH in order achieve effective loading of the silk film.

In a ninth aspect, the present invention relates to the use of the coated silk film according to the first aspect for controlled and sustained release of at least one active agent. Preferably, the use is a non-therapeutic use. As to the definition of the active agent, it is referred to the first aspect of the present invention.

The active agent may be released from the silk film, particularly from the active agent release sheet being part of the silk film or forming the silk film, by diffusion and/or degradation upon exposure to a surrounding environment.

In one embodiment, the surrounding environment is a physiological environment (e.g. a physiological medium). It is preferred that the physiological environment (e.g. the physiological medium) is selected from the group consisting of a physiological buffered solution or a body fluid, e.g. blood, lymph or liquor. It is also preferred that the physiological environment is an organ (e.g. skin) or a part of an organ (e.g. tissue). The release of the active agent from the coated silk film can be induced by introducing the coated silk film into a physiological buffered aqueous solution or a body fluid such as blood, lymph or liquor, or by applying the coated silk film onto an organ (e.g. skin) or part of an organ (e.g. tissue).

In one another embodiment, the surrounding environment is a non-physiological environment (e.g. a non-physiological medium). It is preferred that the non-physiological environment (e.g. the non-physiological medium) is selected from the group consisting of an aqueous solution such as water or a buffered aqueous solution, an alcoholic solution, and an organic solution.

It should be further noted that the active agent(s) may be released by diffusion and/or degradation upon exposure to a surrounding intracorporeal or extracorporeal environment.

Preferably, the release of the active agent displays relatively linear kinetics, thereby providing a constant supply of the active agent over the release period.

It is preferred that less than 20%, preferably less than 15%, more preferably less than 10%, and most preferably less than 5%, e.g. less than 20, 19, 18, 17, 16, 15, 14, 13, 12, 11, 10, 9, 8, 7, 6, or 5%, of the active agent is released, particularly into the surrounding environment, within the first 24 hours.

It is, alternatively or additionally, preferred that more than 50%, preferably more than 70%, more preferably more than 80%, and most preferably 100% of the active agent is released, particularly into the surrounding environment, within 36 hours. It is, alternatively or additionally, preferred that more than 50%, preferably more than 70%, more preferably more than 80%, and most preferably 100% of the active agent is released, particularly into the surrounding environment, within 48 hours. It is, alternatively or additionally, preferred that more than 50%, preferably more than 70%, more preferably more than 80%, and most preferably 100% of the active agent is released, particularly into the surrounding environment, within 72 hours.

It is, alternatively or additionally, more preferred that more than 50%, preferably more than 70%, more preferably more than 80%, and most preferably 100% of the active agent is released, particularly into the surrounding environment, within 7 days. It is, alternatively or additionally, more preferred that more than 50%, preferably more than 70%, more preferably more than 80%, and most preferably 100% of the active agent is released, particularly into the surrounding environment, within 14 days. It is, alternatively or additionally, more preferred that more than 50%, preferably more than 70%, more preferably more than 80%, and most preferably 100% of the active agent is released, particularly into the surrounding environment, within 20 days. It is, alternatively or additionally, more preferred that more than 50%, preferably more than 70%, more preferably more than 80%, and most preferably 100% of the active agent is released, particularly into the surrounding environment, within 30 days. It is, alternatively or additionally, more preferred that more than 50%, preferably more than 70%, more preferably more than 80%, and most preferably 100% of the active agent is released, particularly into the surrounding environment, within 35 days.

It is, alternatively or additionally, even more preferred that more than 50%, preferably more than 70%, more preferably more than 80%, and most preferably 100% of the active agent is released, particularly into the surrounding environment, within 5 weeks. It is, alternatively or additionally, even more preferred that more than 50%, preferably more than 70%, more preferably more than 80%, and most preferably 100% of the active agent is released, particularly into the surrounding environment, within 6 weeks. It is, alternatively or additionally, even more preferred that more than 50%, preferably more than 70%, more preferably more than 80%, and most preferably 100% of the active agent is released, particularly into the surrounding environment, within 7 weeks. It is, alternatively or additionally, even more preferred that more than 50%, preferably more than 70%, more preferably more than 80%, and most preferably 100% of the active agent is released, particularly into the surrounding environment, within 8 weeks.

It is, alternatively or additionally, most preferred that more than 50%, preferably more than 70%, more preferably more than 80%, and most preferably 100% of the active agent is released, particularly into the surrounding environment, within 3 months. It is, alternatively or additionally, most preferred that more than 50%, preferably more than 70%, more preferably more than 80%, and most preferably 100% of the active agent is released, particularly into the surrounding environment, within 4 months. It is, alternatively or additionally, most preferred that more than 50%, preferably more than 70%, more preferably more than 80%, and most preferably 100% of the active agent is released, particularly into the surrounding environment, within 5 months. It is, alternatively or additionally, most preferred that more than 50%, preferably more than 70%, more preferably more than 80%, and most preferably 100% of the active agent is released, particularly into the surrounding environment, within 6 months. It is, alternatively or additionally, most preferred that more than 50%, preferably more than 70%, more preferably more than 80%, and most preferably 100% of the active agent is released, particularly into the surrounding environment, within 7 months. It is, alternatively or additionally, most preferred that more than 50%, preferably more than 70%, more preferably more than 80%, and most preferably 100% of the active agent is released, particularly into the surrounding environment, within 8 months. It is, alternatively or additionally, most preferred that more than 50%, preferably more than 70%, more preferably more than 80%, and most preferably 100% of the active agent is released, particularly into the surrounding environment, within 9 months. It is, alternatively or additionally, most preferred that more than 50%, preferably more than 70%, more preferably more than 80%, and most preferably 100% of the active agent is released, particularly into the surrounding environment, within 10 months.

In a tenth aspect, the present invention relates to a method of producing a water insoluble silk article comprising the steps of:
(i) providing a silk article, and
(ii) applying water vapour to the silk article, thereby rendering the silk article water insoluble.

Silk articles, e.g. silk films or fibers, produced, e.g. cast or spun, from an aqueous solution or a dispersion display a predominantly α-helical secondary structure. The inventors of the present invention found that the application of water vapour results in a transition to a β-sheet rich structure. While the silk articles, e.g. silk films or fibers, provided in step (i) can be dissolved in water, processed β-sheet rich silk articles, e.g. silk films or fibers, are water-insoluble.

For example, water-insoluble silk films are known in the art. However, these silk films have been rendered water-insoluble by treating them with methanol or ethanol, or by casting them from formic acid. Although methanol, ethanol, or formic acid is evaporated after silk film treatment/formation, residues of these substances might remain in the silk film. Thus, such water-insoluble silk films might have harmful side effects when administered to an individual. The silk articles, e.g. silk films or fibers, produced with the above method have the advantage that they have been rendered water-insoluble by simply applying water vapour. They do not comprise harmful compounds. Thus, they can be basis for a large number of innovative products in the cosmetical, medical, or pharmaceutical market. It is further possible to apply the water-insoluble silk articles, e.g. silk films or fibers, to several preferential objects including, but not limited to, meshes, scaffolds, patches, and nonwovens.

In one embodiment, the water vapour has a temperature of between 1° C. and 121° C., preferably of between 1° C. and 80° C., more preferably of between 4° C. and 50° C., even more preferably of between 15° C. and 40° C., and most preferably of between of between 19° C. or 20° C. (room temperature) and 35° C., e.g. a temperature of 19, 20, 21, 22, 23, 24, 25, 26, 27, 28, 29, 30, 31, 32, 33, 34, or 35° C. and/or the water vapour has a relative humidity of between 50% and 100%, preferably of between 50% and 90%, more preferably of between 60% and 90%, and most preferably of between 70% and 80%, e.g. a relative humidity of 70, 71, 72, 73, 74, 75, 76, 77, 78, 79, or 80%.

In one another embodiment, the silk article comprises at least one active agent. Preferably, the active agent is selected from the group consisting of a biological agent, a pharmaceutical agent, a cosmetic agent, a nutrient, and dietary supplement. As to the definition of the term "active agent" and as to the preferred embodiments of the biological agent, pharmaceutical agent, cosmetic agent, nutrient, or dietary supplement, it is referred to the first aspect of the present invention.

The silk article comprises a silk material. Preferably, the silk article comprises at least one silk polypeptide. Said silk polypeptide comprises at least two repetitive units. As to the definitions with respect to the silk polypeptide and as to the preferred embodiments of the silk polypeptide, it is referred to the first aspect of the present invention.

Preferably, the silk article is selected from the group consisting of a silk film, a silk particle, a silk fiber, a silk foam, a silk mesh, and a silk coating. It is preferred that the silk article, e.g. silk film or fiber, provided in step (i) is produced by the steps of:
(a) providing an aqueous solution or dispersion comprising or consisting of a silk material (e.g. at least one silk polypeptide) and optionally at least one active agent,
(b) forming a silk article, e.g. silk film or fiber, from the aqueous solution or dispersion comprising or consisting of a silk material (e.g. at least one silk polypeptide) and optionally at least one active agent.

In one embodiment, the silk article is a silk film and said silk film is formed in step (b) by applying the aqueous solution or dispersion comprising or consisting of a silk material (e.g. at least one silk polypeptide) and optionally at least one active agent on a support material and drying said aqueous solution or dispersion.

The application of the aqueous solution or dispersion comprising or consisting of a silk material (e.g. at least one silk polypeptide) and optionally at least one active agent may take place by casting, spraying, or dropping said aqueous solution or dispersion on a support material. The support material may be any solid support material such as polystyrene, glass, polytetrafluoroethylene, or silane.

The drying can be carried out, for example, by drying in the air, baking, using a heat chamber, a vacuum chamber, laminar flow (e.g. of a gas such as nitrogen or carbon dioxide), radiation, or a fan (at low temperatures, at room temperature or at elevated temperatures).

In one another embodiment, the silk article is a silk fiber and said silk fiber is formed in step (b) by spinning the silk fiber from the aqueous solution or dispersion comprising or consisting of a silk material (e.g. at least one silk polypeptide) and optionally at least one active agent. The spinning technique preferably is selected from the group consisting of wet spinning and electrospinning.

It is further preferred that the concentration of the at least one silk polypeptide in the aqueous solution is of between 0.1% (w/v) and 30% (w/v), preferably of between 0.5% (w/v) and 20% (w/v), and more preferably of between 1% (w/v) and 10% (w/v).

The aqueous solution or dispersion may be a buffered aqueous solution or dispersion, preferably TRIS buffer-HCl (pH 8), particularly 5 mM TRIS puffer-HCl (pH 8).

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

The following examples are merely illustrative of the present invention and should not be construed to limit the scope of the invention as indicated by the appended claims in any way.

EXAMPLES

Example 1: Production of Silk Films (A) Spray-dried $C_{16}$ proteins were dissolved in 6 M guanidinium thiocyanate and subsequently dialyzed against 5 mM Tris/HCl buffer, pH 8 at 4° C. The pH was measured using a pH meter. The protein solution was centrifuged for 15 min at 10000 rpm and filtered through a 0.45 μm cellulose acetate filter. The protein concentration was determined photometrically. The protein solution was finally diluted with Tris buffer to 2.5% w/v. Films (2.5×3 cm) were cast on the plastic foil A5 22/5B from mtv-messtechnik (Koeln, Germany) and dried in a laminar flow cabinet at room temperature overnight at 45% relative humidity (see FIG. 1A).

(B) Spray-dried $C_{16}$ proteins were dissolved in 6 M guanidinium thiocyanate and subsequently dialyzed against 5 mM Tris/HCl buffer, pH 9 at 4° C. The pH was settled using a pH meter. The protein solution was firstly centrifuged at 4° C. for 15 min at 10000 rpm and secondly filtered through a 0.45 µm cellulose acetate filter. Afterwards, the protein solution was dialyzed against 5 mM Tris/HCl buffer, pH 9 containing 10% of PEG 20 kDa at 4° C. The protein concentration was determined photometrically. The protein concentration of the casting solution was finally adjusted to 5% w/v. Films were cast on the plastic foil A5 22/5B from mtv-messtechnik (Koeln, Germany) at room temperature using the film applicator Coatmaster 510 (Erichsen, Hemer, Germany) having a casting knife of 2000 µm and with a velocity of 1 mm/sec. 2 ml of the casting solution were used to cast each film. During the whole film casting procedure, the film applicator was placed under the laminar flow cabinet. The films were dried at room temperature overnight in the laminar flow cabinet which was closed and switched off. The final films were obtained cutting samples of ca. 2.5×3 cm using a scalpel (see FIG. 1B).

Example 2: Remote Loading of Silk Films

A) Low molecular weight drugs (tetracain hydrochloride, ethacridine monohydrate lactate, nipagin and phenol red) were dissolved at a concentration of 0.5 mg/ml in highly purified water (HPW), Tris 5 mM pH 7, and formate buffer 5 mM, pH 3, respectively. After dissolving the drugs, all solutions were filtered through a 0.45 µm cellulose acetate filter.

For the remote loading process, the previously cast $C_{16}$ films were cut into pieces, weighed and placed into 24-well plates. At least four $C_{16}$ film samples were incubated with 1 ml of each drug solutions for 30 min at gently agitation of 2 rpm at room temperature. After removing the $C_{16}$ films, the quantities of the loaded drugs were calculated indirectly by measuring the remaining loading solutions photometrically. Finally, the loading and the loading-efficiency for each experimental condition were calculated (see Table 1).

For the remote loading of the model protein lysozyme, the loading solution was prepared by dissolving 1% w/v lysozyme in HPW. As before, three different $C_{16}$ films were weighed. Afterwards, $C_{16}$ films were incubated in a 6-well plate with 5 ml of the loading solution at gently agitation of 2 rpm at room temperature. After 30 min, $C_{16}$ films were removed and the loading solution was analysed photometrically at 280 nm. Spectra were recorded using a spectrophotometer. At physiological pH, spider silk films are negatively charged.

As mentioned above, the remote loading of the model protein Lysozyme was also considered. Lysozyme is positively charged at physiological pH. The remote loading of $C_{16}$ films with lysozyme performed in HPW demonstrated that it is possible to load high molecular weight molecules by remote loading (see Table 1).

TABLE 1

Remote loading of different low molecular weight (LMW) drugs and the model protein lysozyme. Loading efficiency (LE) and Loading (L) were determinate at different pH and different ionic strength. HPW stand for highly purified water.

| | pH 7 | | pH 3 | | HPW | |
|---|---|---|---|---|---|---|
| | LE (%) | L (%) | LE (%) | L (%) | LE (%) | L (%) |
| LMW drugs | | | | | | |
| Tetracaine HCl | 24.3 ± 7.7 | 2.5 ± 07 | 0.0 ± 0.0 | 0.0 ± 0.0 | 35.1 ± 8.3 | 3.8 ± 1.9 |
| Ethacridine lact. | 45.8 ± 2.7 | 3.5 ± 1.0 | 16.5 ± 5.4 | 2.4 ± 0.5 | 54.2 ± 3.2 | 3.3 ± 0.3 |
| Nipagin | 0.0 ± 0.0 | 0.0 ± 0.0 | 5.3 ± 2.3 | 0.5 ± 0.2 | 9.6 ± 4.3 | 0.8 ± 0.3 |
| Phenol red | 7.2 ± 2.0 | 0.7 ± 0.2 | 17.2 ± 5.0 | 1.8 ± 0.7 | 2.8 ± 1.3 | 0.3 ± 1.3 |
| Model Protein | | | | | | |
| Lysozyme | — | — | — | — | 22.8 ± 0.7 | 39.8 ± 1.8 |

Figure 2:
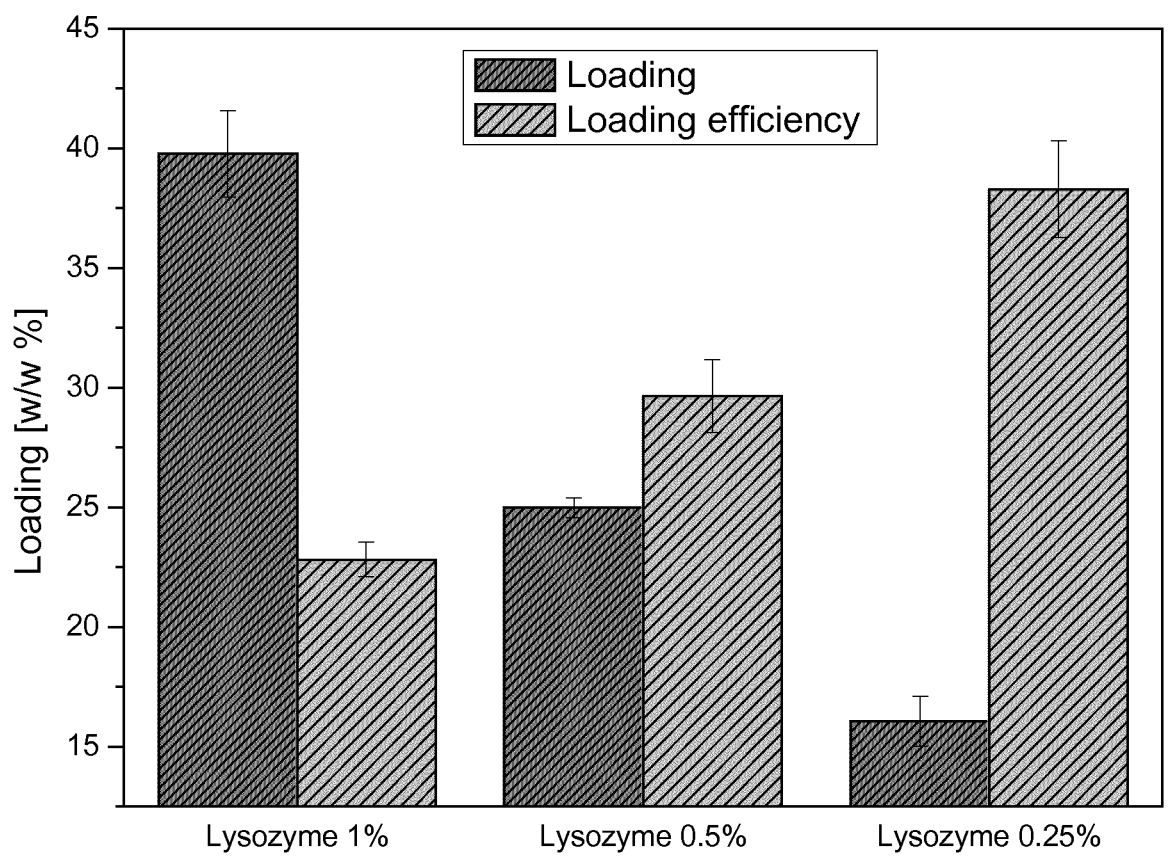
FIG. 2: Shows remote loading of lysozyme as a model protein. Loading efficiency and loading were determinate for lysozyme dissolved in high purified water (HPW). For the remote loading of lysozyme, the loading solution was prepared dissolving 1% w/v lysozyme in high purified water. Three different films were weighted, following by incubation in a 6-well plate with 5 ml of the loading solution at room temperature, at 2 rpm. After 30 min, films were removed and the loading solution was diluted 1:20 and analysed photometrically at 280 nm recording its spectra using a spectrophotometer (Agilent Technologies 8453, Oberhaching, Germany). A calibration curve was prepared using the original lysozyme solution. The same method was performed using as incubation medium of 0.5% and 0.25% of lysozyme.

B) For the remote loading of Lysozyme, the loading solution was prepared dissolving 1% w/v lysozyme in high purified water (HPW). Three different $C_{16}$ films were weighted, followed by incubation in a 6-well plate with 5 ml of the loading solution at gently agitation of 2 rpm at room temperature. After 30 min, $C_{16}$ films were removed and the loading solution was diluted 1:20 and analyzed photometrically at 280 nm. In particular, a spectra of this solution was subsequently recorded using a spectrophotometer (Agilent Technologies 8453, Oberhaching, Germany). A calibration curve was prepared using the original lysozyme solution. The same method was performed using an incubation medium with 0.5% and 0.25% of Lysozyme. The results are shown in FIG. 2.

Example 3: Cumulative Release of Paracetamol, FITC-BSA and FITC-Dextran (FD) from $C_{16}$ Films Cast from an Aqueous Solution A) Spray-dried $C_{16}$ proteins were dissolved in 6 M guanidinium thiocyanate and subsequently dialyzed against 5 mM Tris/HCl buffer, pH 8 at 4° C. The pH was measured using a pH meter. The protein solution was centrifuged at 10000 rpm for 15 min and filtered through a 0.45 µm cellulose acetate filter. The protein concentration was determined photometrically. The protein solution was finally diluted with Tris buffer to 2.5% w/v. Before casting the films, paracetamol was added and dissolved directly in the protein solution. Films (2.5×3 cm) were cast on the plastic foil A5 22/5B from mtv-messtechnik (Koeln, Germany) and dried in a laminar flow cabinet at room temperature overnight at 45% relative humidity. The resulting films contained 2.5 mg of drug. Three film samples containing paracetamol were incubated in 0.01 M PBS buffer, pH 7.4 at 37° C. At predetermined time points, the buffer was removed and replaced with fresh medium. The release buffer was analysed using a UV-Vis spectrophotometer.

Figure 6:
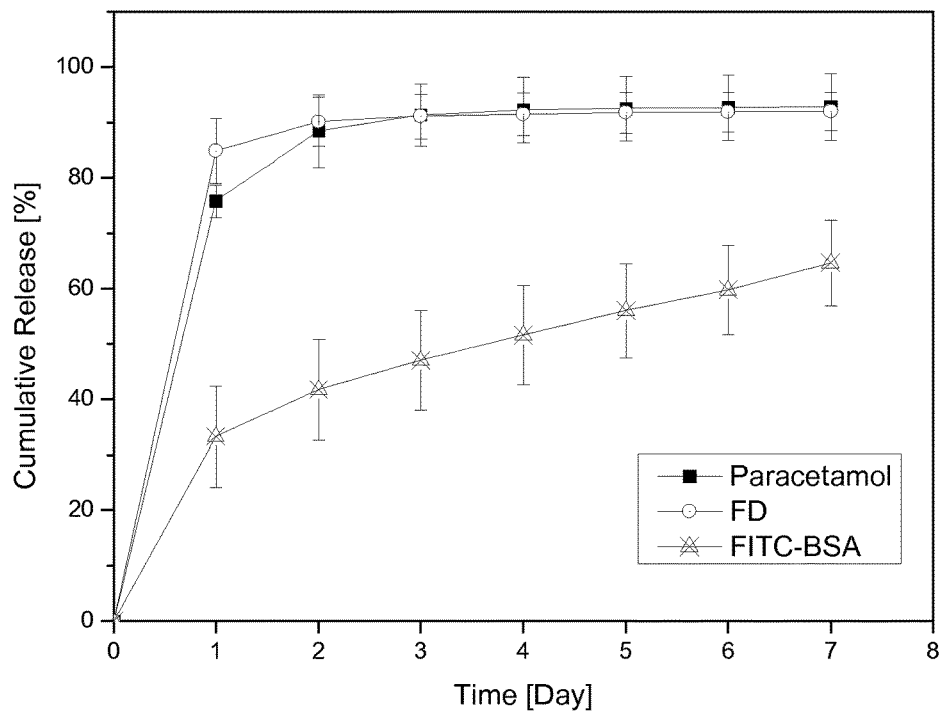
FIG. 6: Shows the cumulative release of paracetamol, FITC-dextran 21 kDa (FD) and FITC-BSA from $C_{16}$ films. Paracetamol: Before casting the $C_{16}$ films, paracetamol was added and dissolved directly in 2.5% $C_{16}$ protein solution. The resulting films contained each 2.5 mg of paracetamol. Three film samples containing paracetamol were incubated in 0.01 M PBS buffer pH 7.4 at 37° C. At predetermined time points, the buffer was removed and replaced with fresh medium. The release buffer was analyzed by NanoDrop 2000 (peqlab, Erlanger, Germany). FITC-BSA and FITC-dextran (FD): 20 mg/mL of FITC-BSA (MW 66.5 kDa) or FITC-dextran (FD) (MW 21 kDa) solution in 0.01 M PBS buffer pH 7.4 were directly mixed with the $C_{16}$ protein solution. Each film contained 1.3 mg of FITC-BSA or FD. Films containing the model drugs (n=3) were incubated in 0.01 M PBS buffer pH 7.4 at 37° C. At predetermined time points the buffer was removed and replaced with fresh medium. The release buffer was analyzed using the fluorescence spectrophotometer Cary Eclipse Varian (Agilent technology, Böblingen, Germany) applying an excitation wavelength of 490 nm and an emission of 520 nm. The drug which was not released was quantified by dissolving the film matrix in a 6 M GdmSCN solution. This solution was subsequently analyzed using a fluorescence spectrophotometer.

A 20 mg/ml FITC-BSA or FITC-dextran (FD) solution in 0.01 M PBS buffer, pH 7.4 was directly mixed with the $C_{16}$ protein solution. Films were cast as described above. Every film contained 25 mg of $C_{16}$ and 1.3 mg of FITC-BSA or FD, respectively. Films containing the substances were incubated in 0.01 M PBS buffer, pH 7.4 at 37° C. At predetermined time points, the buffer was removed and replaced with fresh medium. The release buffer was analysed using a fluorescence spectrophotometer applying an excitation wavelength of 490 nm and an emission of 520 nm. The substance which was not released was quantified by dissolving the film matrix in a 6M GdmSCN solution. This solution was subsequently analysed using a fluorescence spectrophotometer. The sum of the non-released substance and the released amount of substance was calculated as 100%. The results showed that the release depends on the molecular weight of the substances. Spider silk films showed to be an excellent drug carrier for small molecules, capable to completely release paracetamol and FITC-dextran (FD) in a short time period. The release of FITC-BSA, which is six times larger than the used dextran in terms of molecular weight, was observed to be slower. After direct loading with FITC-BSA, $C_{16}$ films released almost 65% of the model protein within one week. Interesting, after a burst release of approx. 30% on day 1, spider silk films released the protein BSA in a constant amount per day. The cumulative release of paracetamol, FITC-dextran 21 kDa (FD) and FITC-BSA from $C_{16}$ films casted from an aqueous solution is shown in FIG. 6.

Figure 3:
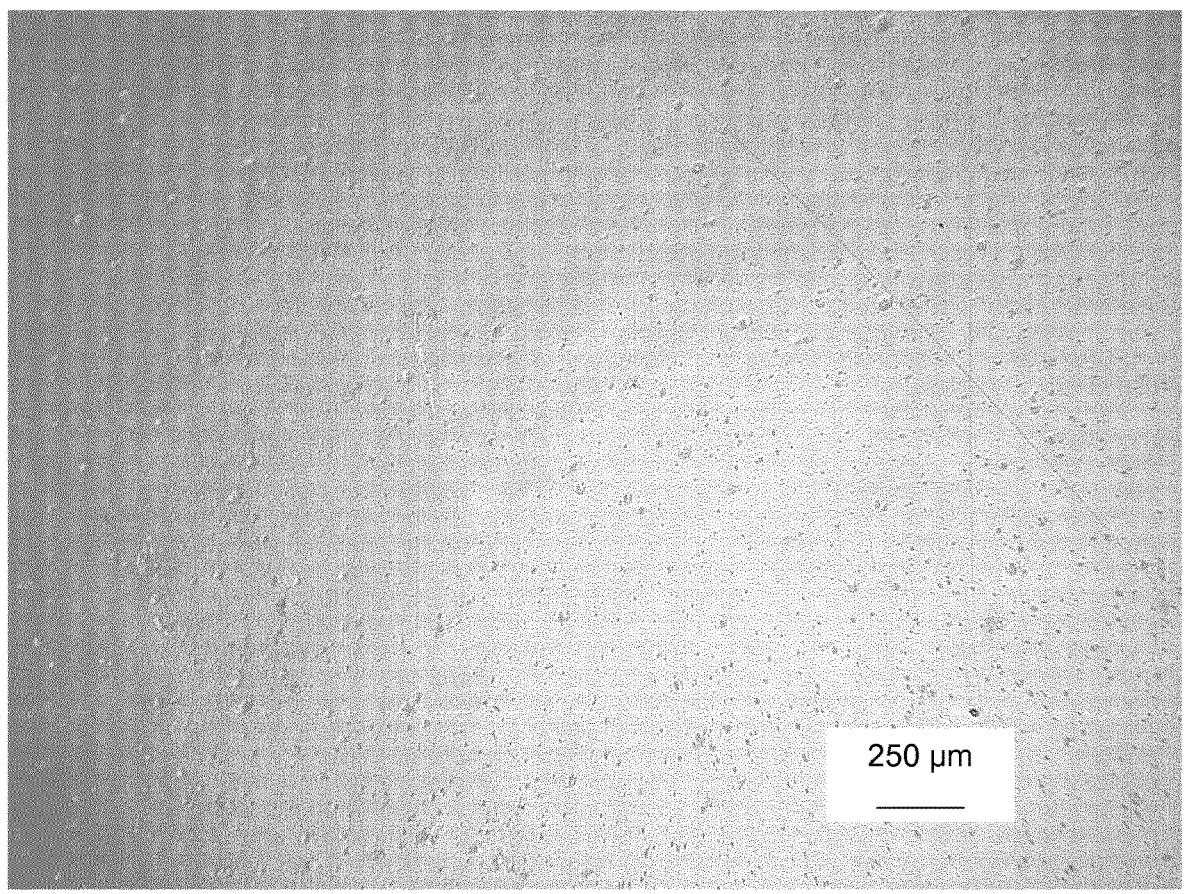
FIG. 3: Shows the surface of a spider silk film comprising $C_{16}$ and containing paracetamol as active agent. Before casting the spider silk film, paracetamol was added and dissolved directly in a 2.5% w/v $C_{16}$ protein solution (direct loading). The resulting spider silk film comprising $C_{16}$ contained 2.5 mg of paracetamol and optically appeared like unloaded films (FIG. 1). In particular, said spider silk film showed a smooth, transparent, and colorless surface. A picture of the film was taken by digital microscope Keyence VHX-500F (Keyence Corporation, Osaka, Japan). Scale bar: 250 μm.

B) Spider silk films comprising $C_{16}$ and containing paracetamol as active agent were prepared as described in Example 3A. The resulting spider silk films contained 2.5 mg of dissolved paracetamol and optically appeared like unloaded films showing a smooth, transparent, and colorless surface (see FIG. 3).

Example 4: Cumulative Release of FITC-BSA from Different Types of Spider Silk Films Spray-dried $C_{16}$ proteins were dissolved in 6 M guanidinium thiocyanate and subsequently dialyzed against 5 mM Tris/HCl buffer, pH 8 at 4° C. The pH was measured using a pH meter. The protein solution was centrifuged at 10000 rpm for 15 min and filtered through a 0.45 μm cellulose acetate filter. The protein concentration was determined photometrically. The protein solution was finally diluted with Tris buffer to 2.5% w/v.

Monolayer films were prepared by mixing a 20 mg/mL FITC-BSA solution in 0.01 M PBS buffer, pH 7.4 with the aqueous $C_{16}$ solution. Films (2.5×3 cm) were cast on the plastic foil A5 22/5B from mtv-messtechnik (Koeln, Germany) and dried in a laminar flow cabinet at room temperature overnight at 45% relative humidity. After casting, each film contained 1.3 mg of the model drug.

3-Layer films were prepared as follows: In a first step, a $C_{16}$ film layer containing FITC-BSA and glycerol was prepared by adding 1% w/v of glycerol directly to the casting solution comprising $C_{16}$ and by subsequently adding a 20 mg/ml FITC-BSA solution in 0.01 M PBS buffer, pH 7.4 to said casting solution. The film layer was cast as described above. The film layer contained 1.3 mg of FITC-BSA. In a second step, the $C_{16}$ film layer containing FITC-BSA and the plasticizer glycerol was positioned between two $C_{16}$ film layers. Said three film layers were pressed together applying 2000 N for 5 min. During this process, 3-Layer films were created where only the middle layer contained the model drug FITC-BSA.

In one case, sandwich films were additionally coated by dipping them in a 5% w/v $C_{16}$ solution (Coated 3-Layer films, sealed films). They were dried overnight at room temperature (RT). The 5% w/v $C_{16}$ solution was prepared by dialysis of the protein solution obtained by the method described above (Example 1).

7-Layer films were prepared pressing seven film layers together. 2000 N for 5 min were applied. In particular, one $C_{16}$ film layer comprising FITC-BSA and glycerol and six $C_{16}$ film layers, wherein glycerol containing $C_{16}$ film layers and glycerol free $C_{16}$ film layers were arranged in alteration, where pressed together.

Figure 9:
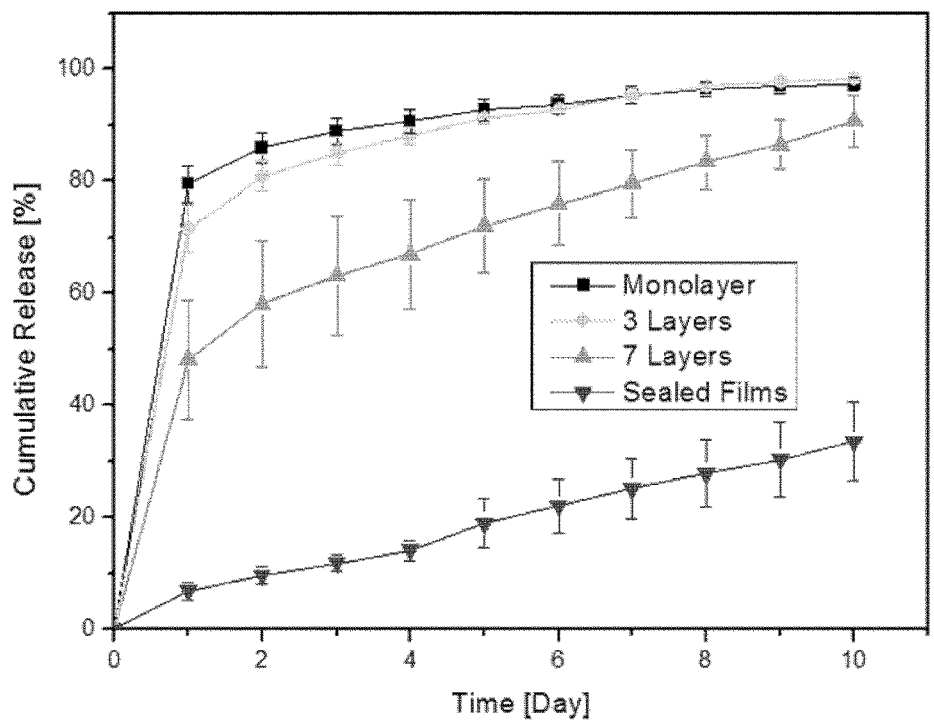
FIG. 9: Shows the cumulative release of FITC-BSA from different kind of $C_{16}$ films (n=3) and a coated $C_{16}$ film (n=3). Monolayer films were prepared by mixing a 20 mg/mL FITC-BSA solution in 0.01 M PBS buffer pH 7.4 with the $C_{16}$ protein solution. Each film contained 1.3 mg of the model drug FITC-BSA. 3 Layer films were prepared by positioning one $C_{16}$ film layer containing the model drug FITC-BSA and the plasticizer glycerin (1% w/v) between two $C_{16}$ film layers. The film layers were pressed together using the hydraulic press 5T (Maassen GmbH, Reutlingen, Germany) and applying 0.2 t for 5 min. Three-layer films were created where only the middle layer contained the model drug FITC-BSA. In one case, these sandwich films were coated by dipping them in a 5% w/v $C_{16}$ solution (Coated 3 Layers). 7 Layer films were prepared by pressing seven film layers together. 0.2 t for 5 min were applied. In particular, one $C_{16}$ film layer comprising the model drug FITC-BSA and the plasticizer glycerol as well as six $C_{16}$ film layers, wherein plasticizer containing $C_{16}$ film layers and plasticizer free $C_{16}$ film layers were arranged in alteration, were pressed together. Three samples of all these different kind of films were incubated in 0.01 M PBS buffer pH 7.4 at 37° C. At predetermined time points the buffer was removed and replaced with fresh medium. The release buffer was analyzed using the fluorescence spectrophotometer Cary Eclipse Varian (Agilent technology, Böblingen, Germany) applying an excitation wavelength of 490 nm and an emission of 520 nm. The drug which was not released, was quantified by dissolving the film matrix in a 6 M GdmSCN solution. This solution was subsequently analyzed by fluorescence spectrophotometer.

Three samples of all these different kind of films were incubated in 0.01 M PBS buffer, pH 7.4 at 37° C. At predetermined time points, the buffer was removed and replaced with fresh medium. The release buffer was analysed using a fluorescence spectrophotometer applying an excitation wavelength of 490 nm and an emission of 520 nm. The drug which was not released was quantified by dissolving the film matrix in a 6 M GdmSCN solution. This solution was subsequently analysed using a fluorescence spectrophotometer. The sum of the non-released substance and the released amount of substance was calculated as 100%. The results are shown in FIG. 9.

Example 5: Cumulative Release of FITC-BSA from Different Kinds of Coated Spider Silk Films (n=3)

Spray-dried $C_{16}$ proteins were dissolved in 6 M guanidinium thiocyanate and subsequently dialyzed against 5 mM Tris/HCl buffer, pH 8 at 4° C. The pH was measured using a pH meter. The protein solution was centrifuged at 10000 rpm for 15 min and filtered through a 0.45 μm cellulose acetate filter. The protein concentration was determined photometrically. The protein solution was finally diluted with Tris buffer to 2.5% w/v.

Monolayer films were prepared by mixing a 20 mg/ml FITC-BSA solution in 0.01 M PBS buffer, pH 7.4 with the aqueous $C_{16}$ solution. Films (2.5×3 cm) were cast on the plastic foil A5 22/5B from mtv-messtechnik (Koeln, Germany) and dried in a laminar flow cabinet at room temperature overnight at 45% relative humidity. After cast, each film contained 1.3 mg of FITC-BSA.

Sandwich films were prepared as following: In a first step, a $C_{16}$ film layer containing FITC-BSA and glycerol was prepared by adding 1% w/v of glycerol directly to the casting solution comprising $C_{16}$ and by subsequently adding a 20 mg/mL FITC-BSA solution in 0.01 M PBS buffer, pH 7.4 to said casting solution. The film layer was cast as described above. The film layer contained 1.3 mg of FITC-BSA. Typically, one $C_{16}$ film layer containing FITC-BSA and the plasticizer glycerol was positioned between two $C_{16}$ film layers. Said three film layers were pressed together by applying 2000 N for 5 min. During this process three-layer films were created, where only the middle layer contained the model drug FITC-BSA.

Finally, monolayer films containing the model drug FITC-BSA and the sandwiches were coated by dipping them in a 5% w/v $C_{16}$ solution. They were dried overnight at room temperature (RT). The 5% w/v $C_{16}$ solution was prepared by a second dialysis of the protein solution obtained by the method described above (Example 1).

The release of FITC-BSA from these two different systems was subsequently investigated. Three samples were incubated in 0.01 M PBS buffer, pH 7.4 at 37° C. At predetermined time points the buffer was removed and replaced with fresh medium. The release buffer was analyzed using a fluorescence spectrophotometer applying an excitation wavelength of 490 nm and an emission of 520 nm. The drug which was not released was quantified by dissolving the film matrix in a 6 M GdmSCN solution. This solution was subsequently analyzed using a fluorescence spectrophotometer. The sum of the non-released substance and the released amount of substance was calculated as 100%.

Figure 10:
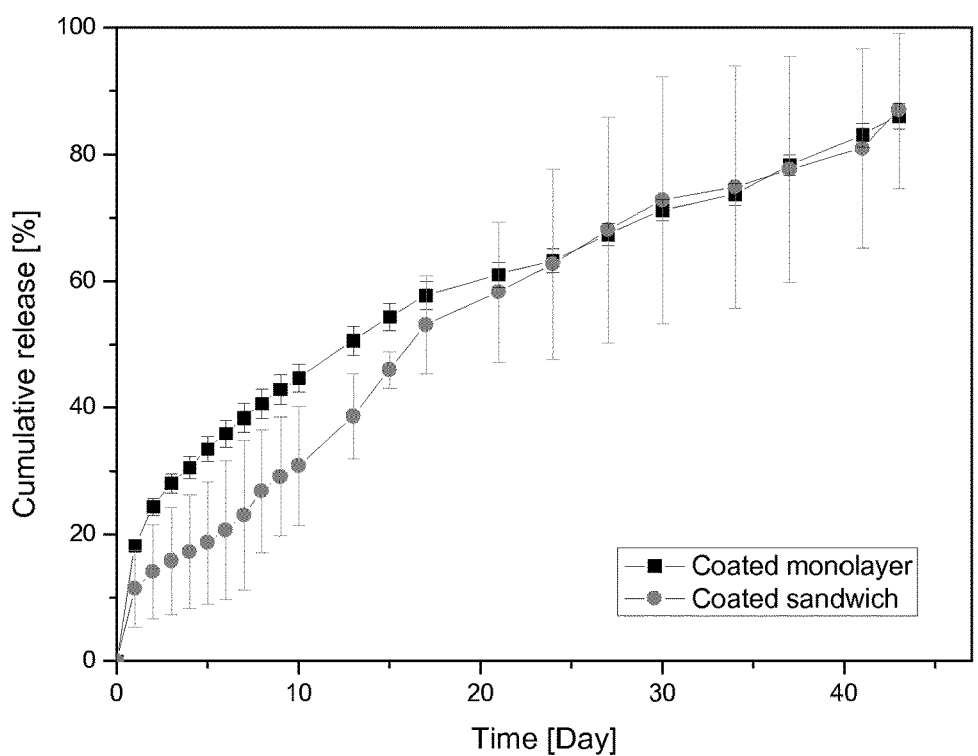
FIG. 10: Shows the cumulative release of FITC-BSA from different kind of coated $C_{16}$ silk films (n=3). Monolayer films were prepared by mixing a 20 mg/mL FITC-BSA solution in 0.01 M PBS buffer pH 7.4 with the $C_{16}$ protein solution. After casting, each film contained 1.3 mg of the model drug FITC-BSA. Sandwich films were prepared by positioning one $C_{16}$ film layer containing the model drug FITC-BSA and the plasticizer glycerol (1% w/v) between two $C_{16}$ film layers. The film layers were pressed together using the hydraulic press 5T (Maassen GmbH, Reutlingen, Germany). 0.2 t for 5 min were applied. Three-layer films were created where only the middle layer contained the model drug FITC-BSA. Finally, monolayer films containing the model drug FITC-BSA and the sandwiches (FIG. 4A) were coated by dipping them in a 5% w/v $C_{16}$ protein solution. They were dried overnight at RT in the dark. Three samples of these different kind of films were incubated in 0.01 M PBS buffer pH 7.4 at 37° C. At predetermined time points the buffer was removed and replaced with fresh medium. The release buffer was analyzed by fluorescence spectrophotometer Cary Eclipse Varian (Agilent technology, Böblingen, Germany) applying an excitation wavelength of 490 nm and an emission of 520 nm. The drug which was not released, was quantified by dissolving the film matrix in a 6 M GdmSCN solution. This solution was subsequently analyzed by fluorescence spectrophotometer.

By coated $C_{16}$ films, a release of the model drug FITC-BSA within 40 days with a zero kinetic order was achieved. The cumulative release of the model drug FITC-BSA from a coated monolayer and a coated sandwich is shown in FIG. 10.

Example 6: Cumulative Release of FITC-BSA from Different $C_{16}$ Films

Figure 7:
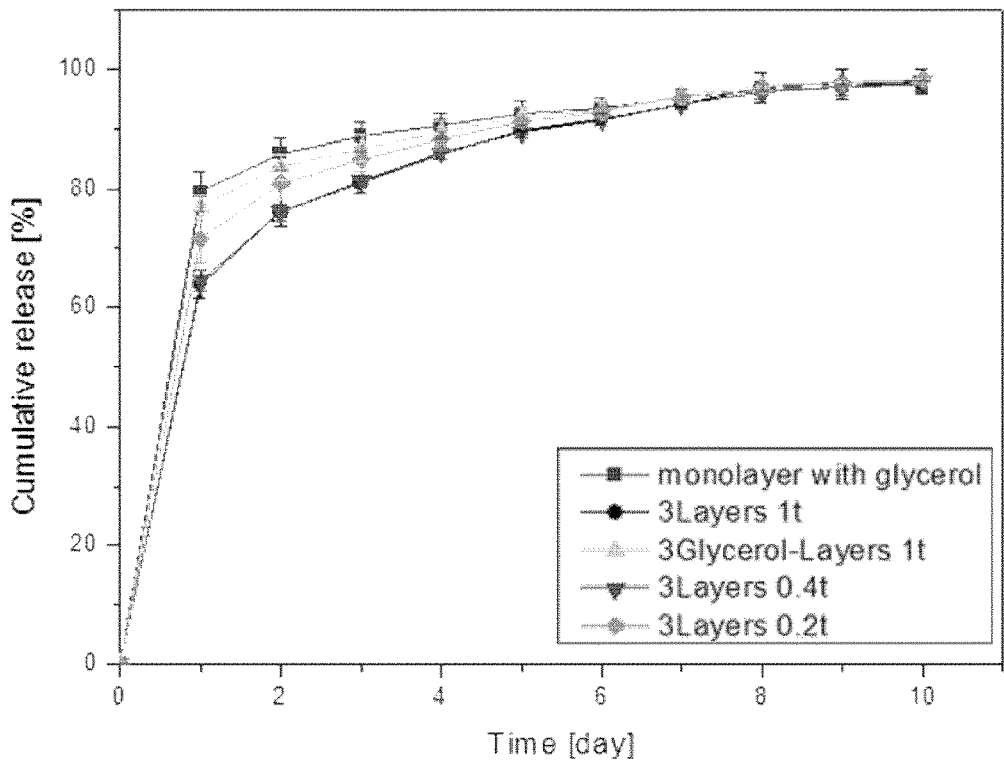
FIG. 7: Shows the cumulative release of the model drug FITC-BSA from different $C_{16}$ films (n=3). 1% w/v of glycerol and a 20 mg/mL FITC-BSA solution in 0.01 M PBS buffer pH 7.4 were directly mixed with the $C_{16}$ protein solution. Each film contained 1.3 mg of FITC-BSA (monolayer with plasticizer glycerol). Typically, one $C_{16}$ film layer containing the model drug FITC-BSA and the plasticizer glycerol was positioned between two $C_{16}$ film layers. Using the hydraulic press 5T (Maassen GmbH, Reutlingen, Germany), the film layers were pressed together by applying 0.2 t for 5 min (3Layers 0.2 t); 0.4 t for 5 min (3Layers 0.4 t); 1 t for 5 min (3Layers 1 t). During this process, three-layer films were created, whereby only the middle layer contained the model drug FITC-BSA. In one case, one $C_{16}$ film layer containing the model drug FITC-BSA and the plasticizer glycerol was positioned between two $C_{16}$ film layers containing the plasticizer glycerol. The film layers were pressed together using a hydraulic press by applying 1 t for 5 min (3 Glycerol-layers 1 t). Three samples of all these different kind of films were incubated in 0.01 M PBS buffer pH 7.4 at 37° C. At predetermined time points the buffer was removed and replaced with fresh medium. The release buffer was analyzed using the fluorescence spectrophotometer Cary Eclipse Varian (Agilent technology, Böblingen, Germany) applying an excitation wavelength of 490 nm and an emission of 520 nm. The drug which was not released, was quantified by dissolving the film matrix in a 6 M GdmSCN solution. This solution was subsequently analyzed using a fluorescence spectrophotometer.

In another experiment, the cumulative release of the model drug FITC-BSA from different $C_{16}$ films (n=3) has been evaluated. 1% w/v of glycerol and a 20 mg/mL FITC-BSA solution in 0.01 M PBS buffer pH 7.4 were directly mixed with the $C_{16}$ protein solution. Each film contained 1.3 mg of FITC-BSA (monolayer with plasticizer glycerol). Typically, one $C_{16}$ film layer containing the model drug FITC-BSA and the plasticizer glycerol was positioned between two $C_{16}$ film layers. Using the hydraulic press 5T (Maassen GmbH, Reutlingen, Germany), the film layers were pressed together by applying 0.2 t for 5 min (3Layers 0.2 t), 0.4 t for 5 min (3Layers 0.4 t) and 1 t for 5 min (3Layers 1 t). During this process, three-layer films were created, whereby only the middle layer contained the model drug FITC-BSA. In one case, one $C_{16}$ film layer containing the model drug FITC-BSA and the plasticizer glycerol was positioned between two $C_{16}$ film layers containing the plasticizer glycerol. The film layers were pressed together using a hydraulic press by applying 1 t for 5 min (3 Glycerol-layers 1 t). Three samples of all these different kind of films were incubated in 0.01 M PBS buffer pH 7.4 at 37° C. At predetermined time points the buffer was removed and replaced with fresh medium. The release buffer was analyzed using the fluorescence spectrophotometer Cary Eclipse Varian (Agilent technology, Böblingen, Germany) applying an excitation wavelength of 490 nm and an emission of 520 nm. The drug which was not released, was quantified by dissolving the film matrix in a 6 M GdmSCN solution. This solution was subsequently analyzed using a fluorescence spectrophotometer. FIG. 7 illustrates the cumulative release of the model drug FITC-BSA from different $C_{16}$ films.

Figure 8:
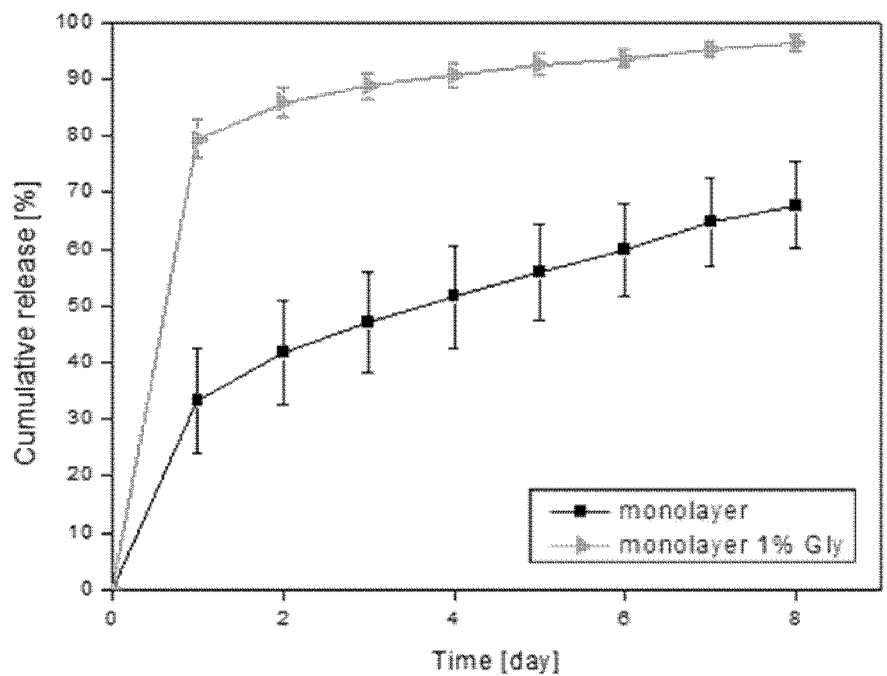
FIG. 8: Shows the effect of glycerol concentration on the release of FITC-BSA from $C_{16}$ films. (A) In one case, 1% w/v of the plasticizer glycerol and a 20 mg/mL FITC-BSA solution in 0.01 M PBS buffer pH 7.4 were directly mixed with the $C_{16}$ protein solution (monolayer with glycerol). In one another case, the plasticizer glycerol was not included in the casting solution (monolayer). After casting, each film contained 1.3 mg of FITC-BSA. Three samples of these two different variants of films were incubated in 0.01 M PBS buffer pH 7.4 at 37° C. At predetermined time points, the buffer was removed and replaced with fresh medium. The release buffer was analyzed using the fluorescence spectrophotometer Cary Eclipse Varian (Agilent technology, Böblingen, Germany) applying an excitation wavelength of 490 nm and an emission of 520 nm. The drug which was not released, was quantified by dissolving the film matrix in a 6 M GdmSCN solution. This solution was subsequently analyzed using a fluorescence spectrophotometer. The monolayer containing glycerol released the model drug BSA much quicker than the monolayer without glycerol. (B) Films were cast from a casting solution containing the model drug FITC-BSA and different concentrations of the plasticizer glycerol: 1%, 3% and 5% w/v. The release study was carried out as described in (A). A film containing more glycerol released the model drug BSA quicker than a film containing low glycerol. In particular, the film containing the model drug FITC-BSA and different concentrations of the plasticizer glycerol, namely 1%, 3% and 5% w/v, was part of a 3-layer $C_{16}$ film (n=3). Said film was positioned between two $C_{16}$ film layers. Thus, said film formed the middle layer of a 3-layer $C_{16}$ film. The middle layer was cast from a casting solution containing the $C_{16}$ protein, the model drug FITC-BSA and different concentrations of the plasticizer glycerol: 1%, 3% and 5% w/v. Glycerol and a 20 mg/mL FITC-BSA solution in 0.01 M PBS buffer pH 7.4 were directly mixed with the $C_{16}$ protein solution. Each film contained 1.3 mg of FITC-BSA and the defined concentration of glycerol (1%, 3% or 5% w/v). The other two $C_{16}$ film layers were cast from a casting solution containing the $C_{16}$ protein. As mentioned above, one $C_{16}$ film layer containing the model drug FITC-BSA and the plasticizer was positioned between two $C_{16}$ film layers. Using the hydraulic press 5T (Maassen GmbH, Reutlingen, Germany), the film layers were pressed together by applying 0.2 t for 5 min. During this process, three-layer films were created, whereby only the middle layer contained the model drug FITC-BSA and the plasticizer.
Figure 8:
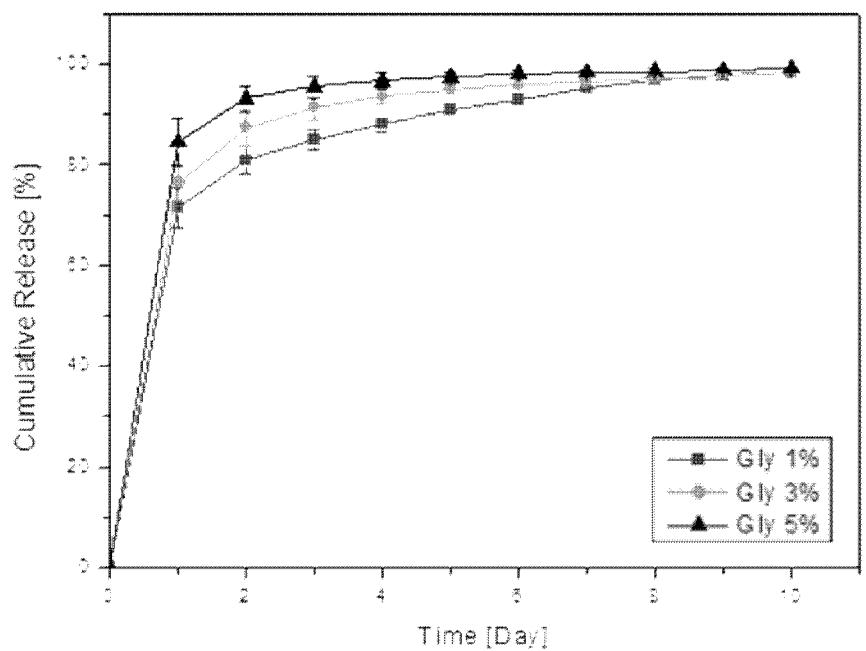

Example 7: Effect of Glycerol Concentration on the Release of FITC-BSA from $C_{16}$ Films In another experiment, the effect of glycerol concentration on the release of FITC-BSA from $C_{16}$ films is shown. In one case, 1% w/v of the plasticizer glycerol and a 20 mg/mL FITC-BSA solution in 0.01 M PBS buffer pH 7.4 were directly mixed with the $C_{16}$ protein solution (monolayer with glycerol). In one another case, the plasticizer glycerol was not included in the casting solution (monolayer). After casting, each film contained 1.3 mg of FITC-BSA. Three samples of these two different variants of films were incubated in 0.01 M PBS buffer pH 7.4 at 37° C. At predetermined time points, the buffer was removed and replaced with fresh medium. The release buffer was analyzed using the fluorescence spectrophotometer Cary Eclipse Varian (Agilent technology, Böblingen, Germany) applying an excitation wavelength of 490 nm and an emission of 520 nm. The drug which was not released, was quantified by dissolving the film matrix in a 6 M GdmSCN solution. This solution was subsequently analyzed using a fluorescence spectrophotometer. The monolayer containing glycerol released the model drug BSA much quicker than the monolayer without glycerol. The results of this experiment are illustrated in FIG. 8A.

Films were further cast from a casting solution containing the model drug FITC-BSA and different concentrations of the plasticizer glycerol: 1%, 3% and 5% w/v. The release study was carried out as described above (see also FIG. 8A). A film containing more glycerol released the model drug BSA quicker than a film containing low glycerol. In particular, the film containing the model drug FITC-BSA and different concentrations of the plasticizer glycerol, namely 1%, 3% and 5% w/v, was part of a 3-layer $C_{16}$ film (n=3). Said film was positioned between two $C_{16}$ film layers. Thus, said film formed the middle layer of a 3-layer $C_{16}$ film. The middle layer was cast from a casting solution containing the $C_{16}$ protein, the model drug FITC-BSA and different concentrations of the plasticizer glycerol: 1%, 3% and 5% w/v. Glycerol and a 20 mg/mL FITC-BSA solution in 0.01 M PBS buffer pH 7.4 were directly mixed with the $C_{16}$ protein solution. Each film contained 1.3 mg of FITC-BSA and the defined concentration of glycerol (1%, 3% or 5% w/v). The other two $C_{16}$ film layers were cast from a casting solution containing the $C_{16}$ protein. As mentioned above, one $C_{16}$ film layer containing the model drug FITC-BSA and the plasticizer was positioned between two $C_{16}$ film layers. Using the hydraulic press 5T (Maassen GmbH, Reutlingen, Germany), the film layers were pressed together by applying 0.2 t for 5 min. During this process, three-layer films were created, whereby only the middle layer contained the model drug FITC-BSA and the plasticizer. The results of this experiment are illustrated in FIG. 8B.

Example 8: Remote and Direct Loading

Figure 11:
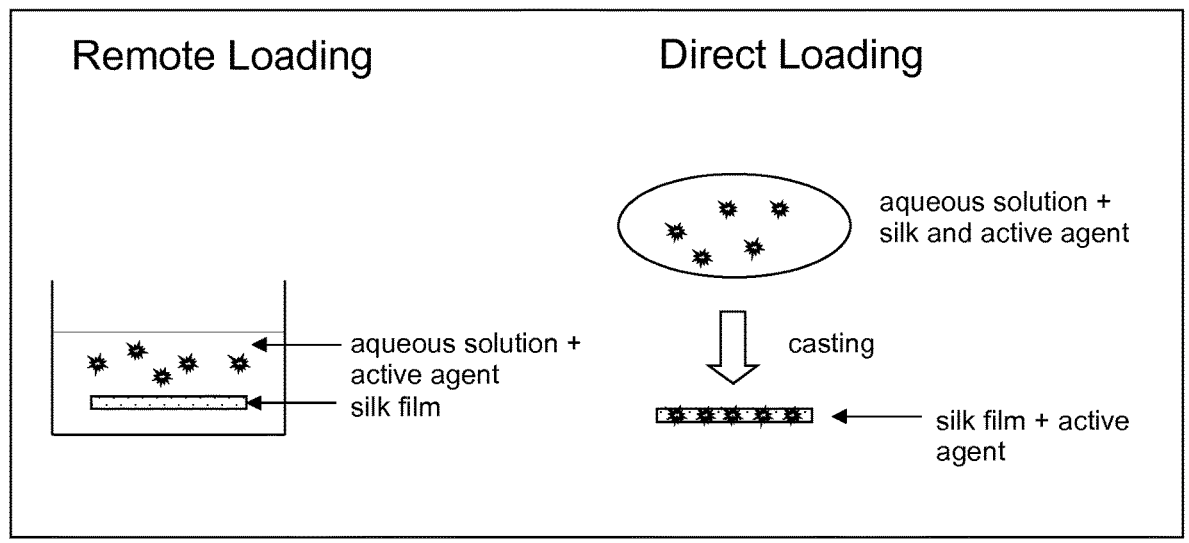
FIG. 11: Shows the remote loading and the direct loading. In the case of the remote-loading, $C_{16}$ silk films were incubated in a drug solution and the loading was mainly driven by electrostatic and hydrophilic/hydrophobic interactions. In the direct loading approach, drugs were directly incorporated into the casting $C_{16}$ protein solution: the drug was directly dissolved in the casting $C_{16}$ protein solution or, alternatively, the $C_{16}$ protein solution was mixed with a second solution containing the dissolved drug. The casting mixture loaded with the drug was cast.
Figure 12:
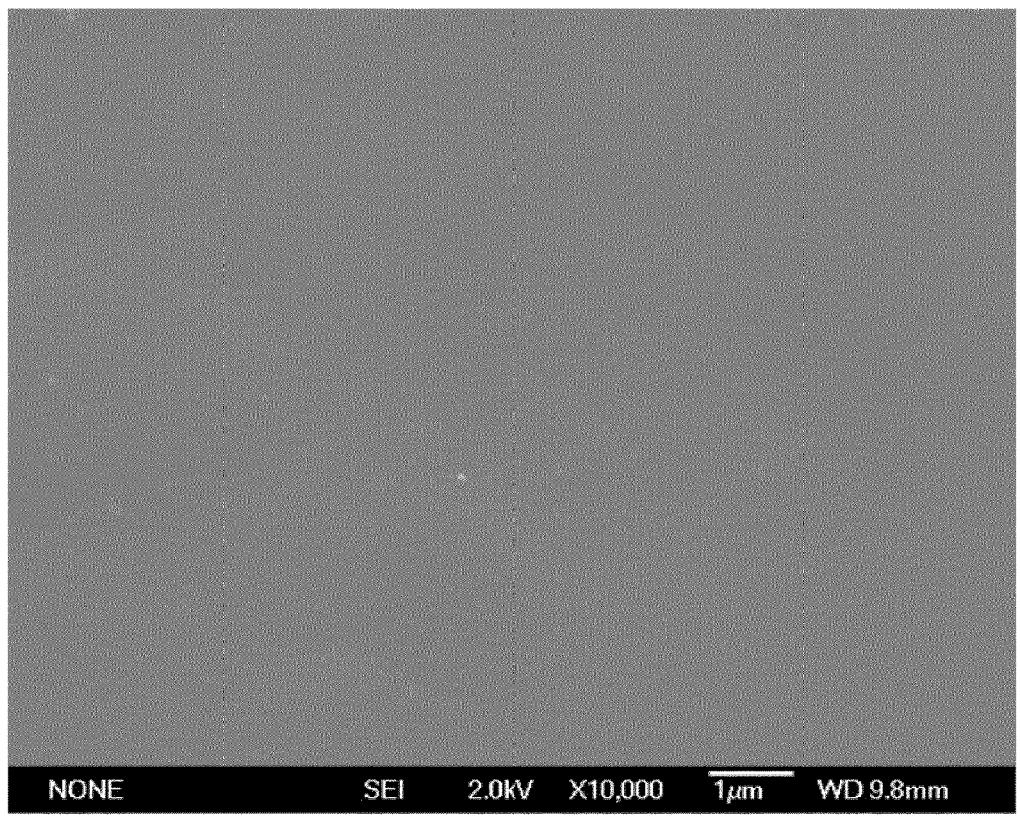
FIG. 12: Scanning electron micrographs (magnification: 10,000×) of a spider silk monolayer film comprising $C_{16}$. The film was cast at room temperature from an aqueous solution comprising $C_{16}$ on a plastic foil A5 22/5B from mtv-messtechnik (Koeln, Germany) by the solvent evaporation technique. The film was immobilized on Leit-Tabs (Plano GmbH, Wetzlar, Germany) to the sample holder. Samples were carbon sputtered under vacuum and analyzed by a Joel JSM-6500F field emission scanning electron microscope (Joel Inc., Peabody, USA). The film had a remarkably uniform and homogenous appearance.

Using the remote loading method, eADF4 ($C_{16}$) films were incubated in a drug solution. The loading of the drug into the $C_{16}$ films was mainly driven by electrostatic and hydrophilic/hydrophobic interactions. An alternative way of loading drugs is represented by the direct loading method. Using the direct loading method, the drug was directly dissolved in the casting spider silk solution or, alternatively, the spider silk solution was mixed with a second solution containing the dissolved drug. Subsequently, the films were cast. The advantage of the direct loading method is the one-step process and the known amount of the drug directly incorporated, which leads to the theoretical 100% of drug loading. FIG. 11 illustrates the remote and direct loading method.

Figure 13:
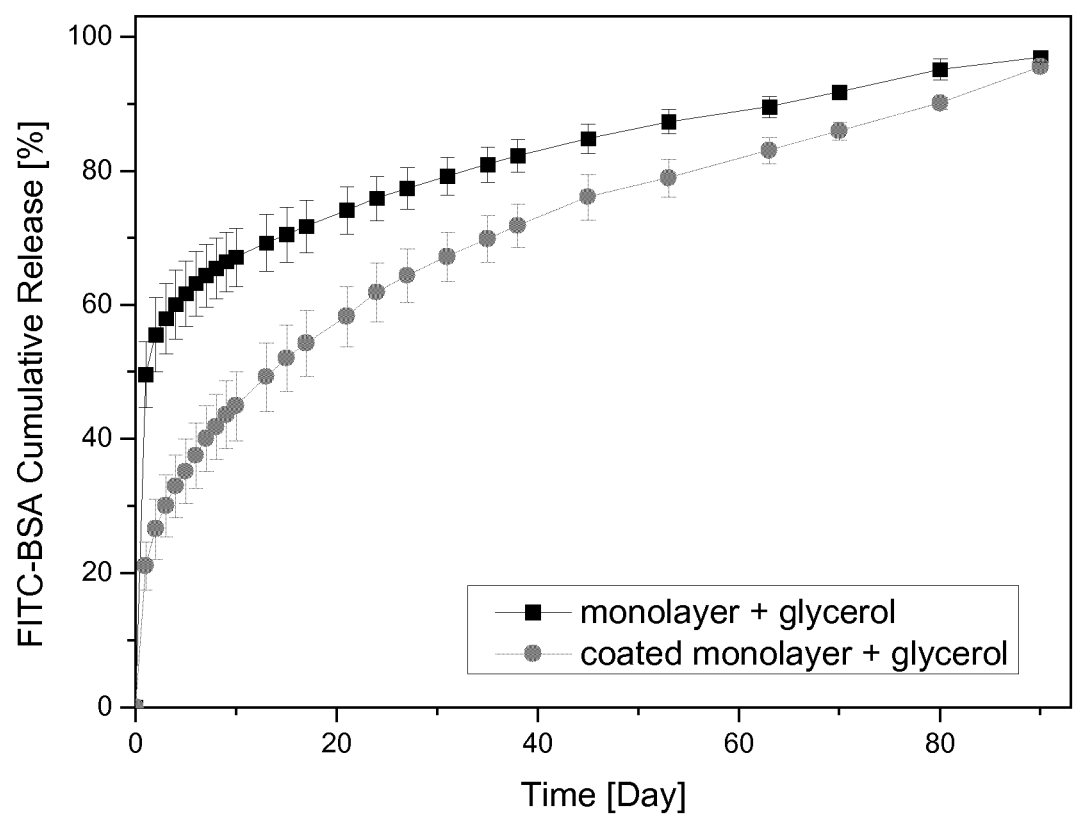
FIG. 13: FITC-BSA released from a spider silk monolayer film comprising $C_{16}$, the model drug FITC-BSA and 1% w/v glycerol (black, n=3) and FITC-BSA released from a coated spider silk monolayer film comprising $C_{16}$, the model drug FITC-BSA and 1% w/v glycerol (grey, n=3). The spider silk monolayer films were cast at room temperature from an aqueous solution comprising $C_{16}$, the model drug FITC-BSA and 1% w/v glycerol on a plastic foil A5 22/5B from mtv-messtechnik (Koeln, Germany) by the solvent evaporation technique. The coated spider silk monolayer films containing $C_{16}$, the model drug FITC-BSA and 1% w/v glycerol were further prepared by dipping them into a 5% w/v $C_{16}$ protein solution. They were dried overnight at room temperature (RT) in the dark. Coating of monolayers containing glycerol with a highly concentrated spider silk protein solution leads to the reduction of the release of FITC-BSA compared to uncoated monolayers containing glycerol.

Example 9: Cumulative Release of FITC-BSA from Monolayer Silk Films and Coated Monolayer Silk Films A further experiment has been performed where FITC-BSA was released from a spider silk monolayer film comprising $C_{16}$, the model drug FITC-BSA and 1% w/v glycerol (black, n=3) and FITC-BSA was released from a coated spider silk monolayer film comprising $C_{16}$, the model drug FITC-BSA and 1% w/v glycerol (grey, n=3). The spider silk monolayer films were cast at room temperature from an aqueous solution comprising $C_{16}$, the model drug FITC-BSA and 1% w/v glycerol on a plastic foil A5 22/5B from mtv-messtechnik (Koeln, Germany) by the solvent evaporation technique. The coated spider silk monolayer films containing $C_{16}$, the model drug FITC-BSA and 1% w/v glycerol were further prepared by dipping them into a 5% w/v $C_{16}$ protein solution. They were dried overnight at room temperature (RT) in the dark. Coating of monolayers containing glycerol with a highly concentrated spider silk protein solution leads to the reduction of the release of FITC-BSA compared to uncoated monolayers containing glycerol. The cumulative release of the model drug FITC-BSA from a monolayer with glycerol and a coated monolayer with glycerol is shown in FIG. 13.

---

The invention claimed is:

1. A coated silk film consisting of
   (i) one silk film layer comprising at least one active agent with a molecular weight between 50 Da and 150 kDa and having a top surface, a bottom surface, and two side surfaces; and
   (ii) one release modifying layer completely and continuously covering all surfaces of the silk film layer,
   wherein the coated silk film is made by first casting a silk film layer with a first silk polypeptide solution comprising the at least one active agent and drying the silk film layer, and then coating the silk film layer with a second silk polypeptide solution to form a release modifying layer completely and continuously covering all surfaces of the silk film layer, wherein each of the first and second silk polypeptide solutions is a 1-10% w/v silk polypeptide solution, and wherein each of the first and second silk polypeptides is $C_{16}$.

2. The coated silk film of claim 1, wherein the least one active agent has a molecular weight between 50 kDa and 150 kDa.

3. The coated silk film of claim 1, wherein the first silk polypeptide solution is a 2.5% w/v silk polypeptide solution, and the second silk polypeptide solution is a 5% w/v silk polypeptide solution.

4. The coated silk film of claim 1, wherein the active agent is selected from the group consisting of a biological agent, a pharmaceutical agent, a cosmetic agent, a nutrient, and a dietary supplement.

5. A method of producing a coated silk film comprising the steps of:
   (i) casting a silk film layer with a first silk polypeptide solution comprising at least one active agent with a molecular weight between 50 Da and 150 kDa and drying the silk film layer to provide one silk film layer comprising the at least one active agent and having a top surface, a bottom surface, and two side surfaces; and
   (ii) dipping the silk film layer in a second silk polypeptide solution to form a release modifying layer completely and continuously covering all surfaces of the silk film layer,
   wherein each of the first and second silk polypeptide solutions is a 1-10% w/v silk polypeptide solution, and wherein each of the first and second silk polypeptides is $C_{16}$.

6. The method of claim 5, wherein the least one active agent has a molecular weight between 50 kDa and 150 kDa.

7. The method of claim 5, wherein the first silk polypeptide solution is a 2.5% w/v silk polypeptide solution, and the second silk polypeptide solution is a 5% w/v silk polypeptide solution.

8. The method of claim 5, wherein the method further comprises the step of drying the release modifying layer.

9. The method of claim 5, wherein the method further comprises the step of applying pressure to the release modifying layer.

10. The method of claim 5, wherein the method further comprises the step of applying water vapour to the release modifying layer.

\* \* \* \* \*

SEQUENCE LISTING

```
<160> NUMBER OF SEQ ID NOS: 43

<210> SEQ ID NO 1
<211> LENGTH: 636
<212> TYPE: PRT
<213> ORGANISM: Araneus diadematus
<220> FEATURE:
<221> NAME/KEY: PEPTIDE
<222> LOCATION: (1)..(636)
<223> OTHER INFORMATION: ADF-3

<400> SEQUENCE: 1

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
                20                  25                  30

Ala Ala Ala Ala Ala Gly Gly Tyr Gly Pro Gly Ser Gly Gln Gln Gly
            35                  40                  45

Pro Ser Gln Gln Gly Pro Gly Gln Gln Pro Gly Gln Gly Pro
    50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gln Gly Pro Tyr Gly Pro
                85                  90                  95

Gly Ser Ser Ala Ala Ala Ala Ala Gly Gly Asn Gly Pro Gly Ser
                100                 105                 110

Gly Gln Gln Gly Ala Gly Gln Gln Gly Pro Gly Gln Gln Gly Pro Gly
            115                 120                 125

Ala Ser Ala Ala Ala Ala Ala Gly Gly Tyr Gly Pro Gly Ser Gly
        130                 135                 140

Gln Gln Gly Pro Gly Gln Gln Gly Pro Gly Gln Gly Pro Tyr Gly
145                 150                 155                 160

Pro Gly Ala Ser Ala Ala Ala Ala Ala Gly Gly Tyr Gly Pro Gly
                165                 170                 175

Ser Gly Gln Gly Pro Gly Gln Gln Gly Pro Gly Gln Gly Pro Tyr
            180                 185                 190

Gly Pro Gly Ala Ser Ala Ala Ala Ala Ala Gly Gly Tyr Gly Pro
        195                 200                 205

Gly Ser Gly Gln Gln Gly Pro Gly Gln Gln Gly Pro Gly Gln Gln Gly
    210                 215                 220

Pro Gly Gly Gln Gly Pro Tyr Gly Pro Gly Ala Ser Ala Ala Ala
225                 230                 235                 240

Ala Ala Gly Gly Tyr Gly Pro Gly Tyr Gly Gln Gln Gly Pro Gly Gln
                245                 250                 255

Gln Gly Pro Gly Gly Gln Gly Pro Tyr Gly Pro Gly Ala Ser Ala Ala
            260                 265                 270

Ser Ala Ala Ser Gly Gly Tyr Gly Pro Gly Ser Gly Gln Gln Gly Pro
        275                 280                 285

Gly Gln Gln Gly Pro Gly Gly Gln Gly Pro Tyr Gly Pro Gly Ala Ser
    290                 295                 300
```

Ala Ala Ala Ala Ala Ala Gly Gly Tyr Gly Pro Gly Ser Gly Gln Gln
305                 310                 315                 320

Gly Pro Gly Gln Gln Gly Pro Gly Gln Gln Gly Pro Gly Gln Gln Gly
            325                 330                 335

Pro Gly Gln Gln Gly Pro Tyr Gly Pro Gly Ala Ser Ala Ala Ala Ala
            340                 345                 350

Ala Ala Gly Gly Tyr Gly Pro Gly Ser Gly Gln Gln Gly Pro Gly Gln
            355                 360                 365

Gln Gly Pro Gly Gln Gln Gly Pro Gly Gln Gln Gly Pro Gly Gln Gln
    370                 375                 380

Gly Pro Gly Gln Gln Gly Pro Gly Gln Gln Gly Pro Gly Gln Gln Gly
385                 390                 395                 400

Pro Gly Gln Gln Gly Pro Gly Gln Gly Ala Tyr Gly Pro Gly Ala
            405                 410                 415

Ser Ala Ala Ala Gly Ala Ala Gly Gly Tyr Gly Pro Gly Ser Gly Gln
            420                 425                 430

Gln Gly Pro Gly Gln Gln Gly Pro Gly Gln Gln Gly Pro Gly Gln Gln
            435                 440                 445

Gly Pro Gly Gln Gln Gly Pro Gly Gln Gln Gly Pro Gly Gln Gln Gly
450                 455                 460

Pro Gly Gln Gln Gly Pro Tyr Gly Pro Gly Ala Ser Ala Ala Ala Ala
465                 470                 475                 480

Ala Ala Gly Gly Tyr Gly Pro Gly Ser Gly Gln Gln Gly Pro Gly Gln
            485                 490                 495

Gln Gly Pro Gly Gln Gln Gly Pro Gly Gln Gly Pro Tyr Gly Pro
            500                 505                 510

Gly Ala Ala Ser Ala Ala Val Ser Val Gly Gly Tyr Gly Pro Gln Ser
            515                 520                 525

Ser Ser Val Pro Val Ala Ser Ala Val Ala Ser Arg Leu Ser Ser Pro
530                 535                 540

Ala Ala Ser Ser Arg Val Ser Ser Ala Val Ser Ser Leu Val Ser Ser
545                 550                 555                 560

Gly Pro Thr Lys His Ala Ala Leu Ser Asn Thr Ile Ser Ser Val Val
            565                 570                 575

Ser Gln Val Ser Ala Ser Asn Pro Gly Leu Ser Gly Cys Asp Val Leu
            580                 585                 590

Val Gln Ala Leu Leu Glu Val Val Ser Ala Leu Val Ser Ile Leu Gly
            595                 600                 605

Ser Ser Ser Ile Gly Gln Ile Asn Tyr Gly Ala Ser Ala Gln Tyr Thr
610                 615                 620

Gln Met Val Gly Gln Ser Val Ala Gln Ala Leu Ala
625                 630                 635

<210> SEQ ID NO 2
<211> LENGTH: 410
<212> TYPE: PRT
<213> ORGANISM: Araneus diadematus
<220> FEATURE:
<221> NAME/KEY: PEPTIDE
<222> LOCATION: (1)..(410)
<223> OTHER INFORMATION: ADF-4

<400> SEQUENCE: 2

Ala Gly Ser Ser Ala Ala Ala Ala Ala Ala Ser Gly Ser Gly Gly
1               5                   10                  15

```
Tyr Gly Pro Glu Asn Gln Gly Pro Ser Gly Pro Val Ala Tyr Gly Pro
             20                  25                  30

Gly Gly Pro Val Ser Ser Ala Ala Ala Ala Ala Ala Gly Ser Gly
         35                  40                  45

Pro Gly Gly Tyr Gly Pro Glu Asn Gln Gly Pro Ser Gly Pro Gly Gly
         50                  55                  60

Tyr Gly Pro Gly Ser Gly Ser Ser Ala Ala Ala Ala Ala Ala Ala Ala
 65                  70                  75                  80

Ala Ser Gly Pro Gly Gly Tyr Gly Pro Gly Ser Gln Gly Pro Ser Gly
                 85                  90                  95

Pro Gly Gly Ser Gly Gly Tyr Gly Pro Gly Ser Gln Gly Ala Ser Gly
             100                 105                 110

Pro Gly Gly Pro Gly Ala Ser Ala Ala Ala Ala Ala Ala Ala Ala
             115                 120                 125

Ala Ser Gly Pro Gly Gly Tyr Gly Pro Gly Ser Gln Gly Pro Ser Gly
             130                 135                 140

Pro Gly Ala Tyr Gly Pro Gly Pro Gly Ser Ser Ala Ala Ala Ala
145                 150                 155                 160

Ala Ala Ala Ala Ser Gly Pro Gly Gly Tyr Gly Pro Gly Ser Gln Gly
                 165                 170                 175

Pro Ser Gly Pro Gly Val Tyr Gly Pro Gly Gly Pro Gly Ser Ser Ala
             180                 185                 190

Ala Ala Ala Ala Ala Gly Ser Gly Pro Gly Gly Tyr Gly Pro Glu
             195                 200                 205

Asn Gln Gly Pro Ser Gly Pro Gly Gly Tyr Gly Pro Gly Gly Ser Gly
             210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
                 245                 250                 255

Gly Pro Gly Ser Gln Gly Gly Ser Gly Pro Gly Ala Ser Ala Ala Ala
             260                 265                 270

Ala Ala Ala Ala Ser Gly Pro Gly Gly Tyr Gly Pro Gly Ser Gln
             275                 280                 285

Gly Pro Ser Gly Pro Gly Tyr Gln Gly Pro Ser Gly Pro Gly Ala Tyr
             290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
                 325                 330                 335

Ser Ser Gly Pro Thr Asn Gly Ala Ala Val Ser Gly Ala Leu Asn Ser
             340                 345                 350

Leu Val Ser Gln Ile Ser Ala Ser Asn Pro Gly Leu Ser Gly Cys Asp
             355                 360                 365

Ala Leu Val Gln Ala Leu Leu Glu Leu Val Ser Ala Leu Val Ala Ile
             370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                 405                 410

<210> SEQ ID NO 3
<211> LENGTH: 5
```

```
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: consensus peptide motif
<220> FEATURE:
<221> NAME/KEY: VARIANT
<222> LOCATION: (4)..(5)
<223> OTHER INFORMATION: Xaa is any amino acid, preferably in each case
      independently selected from A, S, G, Y, P, and Q

<400> SEQUENCE: 3

Gly Pro Gly Xaa Xaa
1               5

<210> SEQ ID NO 4
<211> LENGTH: 5
<212> TYPE: PRT
<213> ORGANISM: Araneus diadematus
<220> FEATURE:
<221> NAME/KEY: VARIANT
<222> LOCATION: (4)..(4)
<223> OTHER INFORMATION: Q at position 4 may also be alanine, serine,
      glycine, tyrosine, proline, or glutamine
<220> FEATURE:
<221> NAME/KEY: VARIANT
<222> LOCATION: (5)..(5)
<223> OTHER INFORMATION: Q at position 5 may also be alanine, serine,
      glycine, tyrosine, proline, or glutamine

<400> SEQUENCE: 4

Gly Pro Gly Gln Gln
1               5

<210> SEQ ID NO 5
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 5

Gly Pro Gly Ala Ser
1               5

<210> SEQ ID NO 6
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 6

Gly Pro Gly Ser Gly
1               5

<210> SEQ ID NO 7
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)
```

```
<400> SEQUENCE: 7

Gly Pro Gly Gly Tyr
1               5

<210> SEQ ID NO 8
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 8

Gly Pro Gly Gly Pro
1               5

<210> SEQ ID NO 9
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 9

Gly Pro Gly Gly Ala
1               5

<210> SEQ ID NO 10
<211> LENGTH: 5
<212> TYPE: PRT
<213> ORGANISM: Unknown
<220> FEATURE:
<223> OTHER INFORMATION: repetitive polypeptide motif found in phylum
      Arthropoda
<220> FEATURE:
<221> NAME/KEY: REPEAT
<222> LOCATION: (1)..(5)
<223> OTHER INFORMATION: peptide motif (resilin)

<400> SEQUENCE: 10

Gly Pro Gly Gly Gly
1               5

<210> SEQ ID NO 11
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 11

Gly Pro Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
```

```
<223> OTHER INFORMATION: Ax peptide motif

<400> SEQUENCE: 12

Ala Ala Ala Ala Ala
1               5

<210> SEQ ID NO 13
<211> LENGTH: 6
<212> TYPE: PRT
<213> ORGANISM: Araneus diadematus
<220> FEATURE:
<221> NAME/KEY: REPEAT
<222> LOCATION: (1)..(6)
<223> OTHER INFORMATION: Ax peptide motif (ADF 3)

<400> SEQUENCE: 13

Ala Ala Ala Ala Ala Ala
1               5

<210> SEQ ID NO 14
<211> LENGTH: 7
<212> TYPE: PRT
<213> ORGANISM: Araneus diadematus
<220> FEATURE:
<221> NAME/KEY: REPEAT
<222> LOCATION: (1)..(7)
<223> OTHER INFORMATION: Ax peptide motif (ADF-4)

<400> SEQUENCE: 14

Ala Ala Ala Ala Ala Ala Ala
1               5

<210> SEQ ID NO 15
<211> LENGTH: 8
<212> TYPE: PRT
<213> ORGANISM: Araneus diadematus
<220> FEATURE:
<221> NAME/KEY: REPEAT
<222> LOCATION: (1)..(8)
<223> OTHER INFORMATION: Ax peptide motif (ADF-4)

<400> SEQUENCE: 15

Ala Ala Ala Ala Ala Ala Ala Ala
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(9)
<223> OTHER INFORMATION: Ax peptide motif

<400> SEQUENCE: 16

Ala Ala Ala Ala Ala Ala Ala Ala Ala
1               5

<210> SEQ ID NO 17
<211> LENGTH: 10
<212> TYPE: PRT
<213> ORGANISM: Araneus diadematus
<220> FEATURE:
<221> NAME/KEY: REPEAT
<222> LOCATION: (1)..(10)
<223> OTHER INFORMATION: Ax peptide motif (ADF-4)
```

```
<400> SEQUENCE: 17

Ala Ala Ala Ala Ala Ala Ala Ala Ala
1               5                   10

<210> SEQ ID NO 18
<211> LENGTH: 9
<212> TYPE: PRT
<213> ORGANISM: Unknown
<220> FEATURE:
<223> OTHER INFORMATION: elastomeric protein (resilin) found commonly in
      phylum Arthropoda
<220> FEATURE:
<221> NAME/KEY: REPEAT
<222> LOCATION: (1)..(9)
<223> OTHER INFORMATION: peptide motif (based on resilin)

<400> SEQUENCE: 18

Gly Gly Arg Pro Ser Asp Thr Tyr Gly
1               5

<210> SEQ ID NO 19
<211> LENGTH: 9
<212> TYPE: PRT
<213> ORGANISM: Unknown
<220> FEATURE:
<223> OTHER INFORMATION: elastomeric protein (resilin) found commonly in
      phylum Arthropoda
<220> FEATURE:
<221> NAME/KEY: REPEAT
<222> LOCATION: (1)..(9)
<223> OTHER INFORMATION: peptide motif (based on resilin)

<400> SEQUENCE: 19

Gly Gly Arg Pro Ser Ser Ser Tyr Gly
1               5

<210> SEQ ID NO 20
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module A (ADF-3)

<400> SEQUENCE: 20

Gly Pro Tyr Gly Pro Gly Ala Ser Ala Ala Ala Ala Ala Ala Gly Gly
1               5                   10                  15

Tyr Gly Pro Gly Ser Gly Gln Gln
            20

<210> SEQ ID NO 21
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module C (ADF-4)

<400> SEQUENCE: 21

Gly Ser Ser Ala Ala Ala Ala Ala Ala Ala Ala Ser Gly Pro Gly Gly
1               5                   10                  15
```

```
Tyr Gly Pro Glu Asn Gln Gly Pro Ser Gly Pro Gly Gly Tyr Gly Pro
            20                  25                  30

Gly Gly Pro
        35

<210> SEQ ID NO 22
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(20)
<223> OTHER INFORMATION: Module Q (ADF-3)

<400> SEQUENCE: 22

Gly Pro Gly Gln Gln Gly Pro Gly Gln Gln Gly Pro Gly Gln Gln Gly
1               5                   10                  15

Pro Gly Gln Gln
            20

<210> SEQ ID NO 23
<211> LENGTH: 34
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(34)
<223> OTHER INFORMATION: Module S (Resilin)

<400> SEQUENCE: 23

Pro Gly Ser Ser Ala Ala Ala Ala Ala Ala Ala Ser Gly Pro Gly
1               5                   10                  15

Gln Gly Gln Gly Gln Gly Gln Gly Gln Gly Gly Arg Pro Ser Asp Thr
            20                  25                  30

Tyr Gly

<210> SEQ ID NO 24
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(39)
<223> OTHER INFORMATION: Module R (Resilin)

<400> SEQUENCE: 24

Ser Ala Ala Ala Ala Ala Ala Ala Gly Pro Gly Gly Asn Gly
1               5                   10                  15

Gly Arg Pro Ser Asp Thr Tyr Gly Ala Pro Gly Gly Asn Gly Gly
            20                  25                  30

Arg Pro Ser Ser Ser Tyr Gly
        35

<210> SEQ ID NO 25
<211> LENGTH: 24
<212> TYPE: PRT
<213> ORGANISM: Artificial Sequence
<220> FEATURE:
<223> OTHER INFORMATION: synthetic
```

```
<220> FEATURE:
<221> NAME/KEY: DOMAIN
<222> LOCATION: (1)..(24)
<223> OTHER INFORMATION: Module Ac

<400> SEQUENCE: 25

Gly Pro Tyr Gly Pro Gly Ala Ser Ala Ala Ala Ala Ala Ala Gly Gly
1               5                   10                  15

Tyr Gly Pro Gly Cys Gly Gln Gln
            20

<210> SEQ ID NO 26
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module Ak

<400> SEQUENCE: 26

Gly Pro Tyr Gly Pro Gly Ala Ser Ala Ala Ala Ala Ala Ala Gly Gly
1               5                   10                  15

Tyr Gly Pro Gly Lys Gly Gln Gln
            20

<210> SEQ ID NO 27
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Cc

<400> SEQUENCE: 27

Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Gly Tyr Gly Pro
            20                  25                  30

Gly Gly Pro
        35

<210> SEQ ID NO 28
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck1

<400> SEQUENCE: 28

Gly Ser Ser Ala Ala Ala Ala Ala Ala Ala Ser Gly Pro Gly Gly
1               5                   10                  15

Tyr Gly Pro Glu Asn Gln Gly Pro Lys Gly Pro Gly Gly Tyr Gly Pro
            20                  25                  30

Gly Gly Pro
        35
```

-continued

```
<210> SEQ ID NO 29
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck2

<400> SEQUENCE: 29

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Gly Tyr Gly Pro
                20                  25                  30

Gly Gly Pro
        35

<210> SEQ ID NO 30
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ckc

<400> SEQUENCE: 30

Gly Ser Ser Ala Ala Ala Ala Ala Ala Ala Ser Gly Pro Gly Gly
1               5                   10                  15

Tyr Gly Pro Lys Asn Gln Gly Pro Cys Gly Pro Gly Gly Tyr Gly Pro
                20                  25                  30

Gly Gly Pro
        35

<210> SEQ ID NO 31
<211> LENGTH: 124
<212> TYPE: PRT
<213> ORGANISM: Artificial Sequence
<220> FEATURE:
<223> OTHER INFORMATION: based on ADF-3
<220> FEATURE:
<221> NAME/KEY: DOMAIN
<222> LOCATION: (1)..(124)
<223> OTHER INFORMATION: NR3 (ADF-3)

<400> SEQUENCE: 31

Gly Ala Ala Ser Ala Ala Val Ser Val Gly Gly Tyr Gly Pro Gln Ser
1               5                   10                  15

Ser Ser Ala Pro Val Ala Ser Ala Ala Ala Ser Arg Leu Ser Ser Pro
                20                  25                  30

Ala Ala Ser Ser Arg Val Ser Ser Ala Val Ser Ser Leu Val Ser Ser
            35                  40                  45

Gly Pro Thr Asn Gln Ala Ala Leu Ser Asn Thr Ile Ser Ser Val Val
        50                  55                  60

Ser Gln Val Ser Ala Ser Asn Pro Gly Leu Ser Gly Cys Asp Val Leu
65                  70                  75                  80

Val Gln Ala Leu Leu Glu Val Val Ser Ala Leu Val Ser Ile Leu Gly
                85                  90                  95
```

```
Ser Ser Ser Ile Gly Gln Ile Asn Tyr Gly Ala Ser Ala Gln Tyr Thr
            100                 105                 110

Gln Met Val Gly Gln Ser Val Ala Gln Ala Leu Ala
        115                 120
```

<210> SEQ ID NO 32
<211> LENGTH: 109
<212> TYPE: PRT
<213> ORGANISM: Artificial Sequence
<220> FEATURE:
<223> OTHER INFORMATION: based on ADF-4
<220> FEATURE:
<221> NAME/KEY: DOMAIN
<222> LOCATION: (1)..(109)
<223> OTHER INFORMATION: NR4 (ADF-4)

<400> SEQUENCE: 32

```
Gly Ala Tyr Gly Pro Ser Pro Ser Ala Ser Ala Ser Val Ala Ser
1               5                   10                  15

Arg Leu Ser Ser Pro Ala Ala Ser Ser Arg Val Ser Ser Ala Val Ser
            20                  25                  30

Ser Leu Val Ser Ser Gly Pro Thr Asn Gly Ala Ala Val Ser Gly Ala
            35                  40                  45

Leu Asn Ser Leu Val Ser Gln Ile Ser Ala Ser Asn Pro Gly Leu Ser
50                  55                  60

Gly Cys Asp Ala Leu Val Gln Ala Leu Leu Glu Leu Val Ser Ala Leu
65                  70                  75                  80

Val Ala Ile Leu Ser Ser Ala Ser Ile Gly Gln Val Asn Val Ser Ser
            85                  90                  95

Val Ser Gln Ser Thr Gln Met Ile Ser Gln Ala Leu Ser
            100                 105
```

<210> SEQ ID NO 33
<211> LENGTH: 136
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(136)
<223> OTHER INFORMATION: derived from Latrodectus hesperus

<400> SEQUENCE: 33

```
Met Gly Gln Ala Asn Thr Pro Trp Ser Ser Lys Ala Asn Ala Asp Ala
1               5                   10                  15

Phe Ile Asn Ser Phe Ile Ser Ala Ala Ser Asn Thr Gly Ser Phe Ser
            20                  25                  30

Gln Asp Gln Met Glu Asp Met Ser Leu Ile Gly Asn Thr Leu Met Ala
        35                  40                  45

Ala Met Asp Asn Met Gly Gly Arg Ile Thr Pro Ser Lys Leu Gln Ala
        50                  55                  60

Leu Asp Met Ala Phe Ala Ser Ser Val Ala Glu Ile Ala Ala Ser Glu
65                  70                  75                  80

Gly Gly Asp Leu Gly Val Thr Thr Asn Ala Ile Ala Asp Ala Leu Thr
            85                  90                  95

Ser Ala Phe Tyr Gln Thr Thr Gly Val Val Asn Ser Arg Phe Ile Ser
            100                 105                 110

Glu Ile Arg Ser Leu Ile Gly Met Phe Ala Gln Ala Ser Ala Asn Asp
            115                 120                 125
```

Val Tyr Ala Ser Ala Gly Ser Gly
    130                 135

<210> SEQ ID NO 34
<211> LENGTH: 137
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(137)
<223> OTHER INFORMATION: derived from Latrodectus hesperus

<400> SEQUENCE: 34

Met Gly Gln Ala Asn Thr Pro Trp Ser Ser Lys Glu Asn Ala Asp Ala
1               5                   10                  15

Phe Ile Gly Ala Phe Met Asn Ala Ala Ser Gln Ser Gly Ala Phe Ser
                20                  25                  30

Ser Asp Gln Ile Asp Asp Met Ser Val Ile Ser Asn Thr Leu Met Ala
            35                  40                  45

Ala Met Asp Asn Met Gly Gly Arg Ile Thr Gln Ser Lys Leu Gln Ala
50                  55                  60

Leu Asp Met Ala Phe Ala Ser Ser Val Ala Glu Ile Ala Val Ala Asp
65                  70                  75                  80

Gly Gln Asn Val Gly Ala Ala Thr Asn Ala Ile Ser As

Ala Ala Ala Gly Gly Ala Gly Gln Gly Gly Tyr Gly Gly Leu Gly Asn
            115                 120                 125

Gln Gly Ala Gly Arg Gly Gly Gln Gly Ala Ala Ala Ala Ala Ala Gly
        130                 135                 140

Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala Ala
            165                 170                 175

Gly Gly Ala Gly Gln Gly Gly Tyr Gly Gly Leu Gly Gly Gln Gly Ala
            180                 185                 190

Gly Gln Gly Gly Tyr Gly Gly Leu Gly Ser Gln Gly Ala Gly Arg Gly
        195                 200                 205

Gly Leu Gly Gly Gln Gly Ala Gly Ala Ala Ala Ala Ala Ala Ala Gly
        210                 215                 220

Gly Ala Gly Gln Gly Gly Leu Gly Gly Gln Gly Ala Gly Gln Gly Ala
225                 230                 235                 240

Gly Ala Ser Ala Ala Ala Ala Gly Gly Ala Gly Gln Gly Gly Tyr Gly
            245                 250                 255

Gly Leu Gly Ser Gln Gly Ala Gly Arg Gly Gly Glu Gly Ala Gly Ala
        260                 265                 270

Ala Ala Ala Ala Ala Gly Gly Ala Gly Gln Gly Gly Tyr Gly Gly Leu
        275                 280                 285

Gly Gly Gln Gly Ala Gly Gln Gly Gly Tyr Gly Gly Leu Gly Ser Gln
        290                 295                 300

Gly Ala Gly Arg Gly Gly Leu Gly Gly Gln Gly Ala Gly Ala Ala Ala
305                 310                 315                 320

Ala Gly Gly Ala Gly Gln Gly Gly Leu Gly Gly Gln Gly Ala Gly Gln
            325                 330                 335

Gly Ala Gly Ala Ala Ala Ala Ala Gly Gly Ala Gly Gln Gly Gly
            340                 345                 350

Tyr Gly Gly Leu Gly Ser Gln Gly Ala Gly Arg Gly Gly Leu Gly Gly
        355                 360                 365

Gln Gly Ala Gly Ala Val Ala Ala Ala Ala Gly Gly Ala Gly Gln
        370                 375                 380

Gly Gly Tyr Gly Gly Leu Gly Ser Gln Gly Ala Gly Arg Gly Gly Gln
385                 390                 395                 400

Gly Ala Gly Ala Ala Ala Ala Ala Gly Gly Ala Gly Gln Arg Gly
            405                 410                 415

Tyr Gly Gly Leu Gly Asn Gln Gly Ala Gly Arg Gly Gly Leu Gly Gly
            420                 425                 430

Gln Gly Ala Gly Ala Ala Ala Ala Ala Gly Gly Ala Gly Gln
        435                 440                 445

Gly Gly Tyr Gly Gly Leu Gly Asn Gln Gly Ala Gly Arg Gly Gly Gln
        450                 455                 460

Gly Ala Ala Ala Ala Ala Gly Gly Ala Gly Gln Gly Gly Tyr Gly
465                 470                 475                 480

Leu Gly Ser Gln Gly Ala Gly Arg Gly Gly Gln Gly Ala Gly Ala Ala
            485                 490                 495

Ala Ala Ala Ala Val Gly Ala Gly Gln Glu Gly Ile Arg Gly Gln Gly
            500                 505                 510

Ala Gly Gln Gly Gly Tyr Gly Gly Leu Gly Ser Gln Gly Ser Gly Arg
        515                 520                 525

-continued

Gly Gly Leu Gly Gly Gln Gly Ala Gly Ala Ala Ala Ala Ala Gly
         530             535             540

Gly Ala Gly Gln Gly Gly Leu Gly Gly Gln Gly Ala Gly Gln Gly Ala
545             550             555             560

Gly Ala Ala Ala Ala Ala Gly Gly Val Arg Gln Gly Gly Tyr Gly
         565             570             575

Gly Leu Gly Ser Gln Gly Ala Gly Arg Gly Gly Gln Gly Ala Gly Ala
         580             585             590

Ala Ala Ala Ala Gly Gly Ala Gly Gln Gly Gly Tyr Gly Gly Leu
         595             600             605

Gly Gly Gln Gly Val Gly Arg Gly Gly Leu Gly Gly Gln Gly Ala Gly
         610             615             620

Ala Ala Ala Ala Gly Gly Ala Gly Gln Gly Gly Tyr Gly Gly Val Gly
625             630             635             640

Ser Gly Ala Ser Ala Ala Ser Ala Ala Ala Ser Arg Leu Ser Ser Pro
         645             650             655

Gln Ala Ser Ser Arg Val Ser Ser Ala Val Ser Asn Leu Val Ala Ser
         660             665             670

Gly Pro Thr Asn Ser Ala Ala Leu Ser Ser Thr Ile Ser Asn Val Val
         675             680             685

Ser Gln Ile Gly Ala Ser Asn Pro Gly Leu Ser Gly Cys Asp Val Leu
690             695             700

Ile Gln Ala Leu Leu Glu Val Val Ser Ala Leu Ile Gln Ile Leu Gly
705             710             715             720

Ser Ser Ser Ile Gly Gln Val Asn Tyr Gly Ser Ala Gly Gln Ala Thr
         725             730             735

Gln Ile Val Gly Gln Ser Val Tyr Gln Ala Leu
         740             745

<210> SEQ ID NO 36
<211> LENGTH: 627
<212> TYPE: PRT
<213> ORGANISM: Araneus diadematus
<220> FEATURE:
<221> NAME/KEY: PEPTIDE
<222> LOCATION: (1)..(627)
<223> OTHER INFORMATION: MaSp II

<400> SEQUENCE: 36

Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala
         20              25                  30

Ala Ala Ala Ala Gly Pro Gly Gly Tyr Gly Pro Gly Gln Gln Gly Pro
             35              40                  45

Gly Gly Tyr Gly Pro Gly Gln Gln Gly Pro Gly Arg Tyr Gly Pro Gly
         50              55                  60

Gln Gln Gly Pro Ser Gly Pro Gly Ser Ala Ala Ala Ala Ala Gly
65              70                  75                  80

Ser Gly Gln Gln Gly Pro Gly Tyr Gly Pro Arg Gln Gln Gly Pro
         85              90                  95

Gly Gly Tyr Gly Gln Gly Gln Gln Gly Pro Ser Gly Pro Gly Ser Ala
             100             105                 110

Ala Ala Ser Ala Ala Ala Ser Ala Glu Ser Gly Gln Gln Gly Pro
         115             120                 125

Gly Gly Tyr Gly Pro Gly Gln Gln Gly Pro Gly Gly Tyr Gly Pro Gly
            130                 135                 140

Gln Gln Gly Pro Gly Gly Tyr Gly Pro Gly Gln Gln Gly Pro Ser Gly
145                 150                 155                 160

Pro Gly Ser Ala Ala Ala Ala Ala Ala Ala Ser Gly Pro Gly Gln
                165                 170                 175

Gln Gly Pro Gly Gly Tyr Gly Pro Gly Gln Gln Gly Pro Gly Gly Tyr
                180                 185                 190

Gly Pro Gly Gln Gln Gly Pro Ser Gly Pro Gly Ser Ala Ala Ala
            195                 200                 205

Ala Ala Ala Ala Ser Gly Pro Gly Gln Gln Gly Pro Gly Gly Tyr Gly
            210                 215                 220

Pro Gly Gln Gln Gly Pro Gly Gly Tyr Gly Pro Gly Gln Gln Gly Leu
225                 230                 235                 240

Ser Gly Pro Gly Ser Ala Ala Ala Ala Ala Ala Gly Pro Gly Gln
                245                 250                 255

Gln Gly Pro Gly Gly Tyr Gly Pro Gly Gln Gln Gly Pro Ser Gly Pro
            260                 265                 270

Gly Ser Ala Ala Ala Ala Ala Ala Ala Gly Pro Gly Gly Tyr
            275                 280                 285

Gly Pro Gly Gln Gln Gly Pro Gly Gly Tyr Gly Pro Gly Gln Gln Gly
            290                 295                 300

Pro Ser Gly Ala Gly Ser Ala Ala Ala Ala Ala Ala Gly Pro Gly
305                 310                 315                 320

Gln Gln Gly Leu Gly Gly Tyr Gly Pro Gly Gln Gln Gly Pro Gly Gly
            325                 330                 335

Tyr Gly Pro Gly Gln Gln Gly Pro Gly Gly Tyr Gly Pro Gly Ser Ala
            340                 345                 350

Ser Ala Ala Ala Ala Ala Ala Gly Pro Gly Gln Gln Gly Pro Gly Gly
            355                 360                 365

Tyr Gly Pro Gly Gln Gln Gly Pro Ser Gly Pro Gly Ser Ala Ser Ala
            370                 375                 380

Ala Ala Ala Ala Ala Ala Gly Pro Gly Gly Tyr Gly Pro Gly Gln
385                 390                 395                 400

Gln Gly Pro Gly Gly Tyr Ala Pro Gly Gln Gln Gly Pro Ser Gly Pro
            405                 410                 415

Gly Ser Ala Ser Ala Ala Ala Ala Ala Ala Gly Pro Gly Gly
            420                 425                 430

Tyr Gly Pro Gly Gln Gln Gly Pro Gly Gly Tyr Ala Pro Gly Gln Gln
            435                 440                 445

Gly Pro Ser Gly Pro Gly Ser Ala Ala Ala Ala Ala Ala Ala Ala
            450                 455                 460

Gly Pro Gly Gly Tyr Gly Pro Ala Gln Gln Gly Pro Ser Gly Pro Gly
465                 470                 475                 480

Ile Ala Ala Ser Ala Ala Ser Ala Gly Pro Gly Gly Tyr Gly Pro Ala
                485                 490                 495

Gln Gln Gly Pro Ala Gly Tyr Gly Pro Gly Ser Ala Val Ala Ala Ser
            500                 505                 510

Ala Gly Ala Gly Ser Ala Gly Tyr Gly Pro Gly Ser Gln Ala Ser Ala
            515                 520                 525

Ala Ala Ser Arg Leu Ala Ser Pro Asp Ser Gly Ala Arg Val Ala Ser
            530                 535                 540

Ala Val Ser Asn Leu Val Ser Ser Gly Pro Thr Ser Ala Ala Leu
545                 550                 555                 560

Ser Ser Val Ile Ser Asn Ala Val Ser Gln Ile Gly Ala Ser Asn Pro
            565                 570                 575

Gly Leu Ser Gly Cys Asp Val Leu Ile Gln Ala Leu Leu Glu Ile Val
            580                 585                 590

Ser Ala Cys Val Thr Ile Leu Ser Ser Ser Ile Gly Gln Val Asn
        595                 600                 605

Tyr Gly Ala Ala Ser Gln Phe Ala Gln Val Val Gly Ser Val Leu
    610                 615                 620

Ser Ala Phe
625

<210> SEQ ID NO 37
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG cys1

<400> SEQUENCE: 37

Gly Cys Gly Gly Gly Gly Gly Ser Gly Gly Gly Gly
1               5                   10

<210> SEQ ID NO 38
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG cys2

<400> SEQUENCE: 38

Gly Cys Gly Gly Gly Gly Gly Gly
1               5

<210> SEQ ID NO 39
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(14)
<223> OTHER INFORMATION: TAG cys3

<400> SEQUENCE: 39

Gly Cys Gly Gly Ser Gly Gly Gly Ser Gly Gly Gly Gly
1               5                   10

<210> SEQ ID NO 40
<211> LENGTH: 5
<212> TYPE: PRT
<213> ORGANISM: Unknown
<220> FEATURE:
<223> OTHER INFORMATION: repetitive polypeptide motif found in phylum
      Arthropoda
<220> FEATURE:
<221> NAME/KEY: REPEAT

```
<222> LOCATION: (1)..(5)
<223> OTHER INFORMATION: peptide motif (resilin)

<400> SEQUENCE: 40

Gly Pro Gly Gln Gly
1               5

<210> SEQ ID NO 41
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG lys1

<400> SEQUENCE: 41

Gly Lys Gly Gly Gly Gly Gly Ser Gly Gly Gly Gly
1               5                   10

<210> SEQ ID NO 42
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG lys2

<400> SEQUENCE: 42

Gly Lys Gly Gly Gly Gly Gly Gly
1               5

<210> SEQ ID NO 43
<211> LENGTH: 35
<212> TYPE: PRT
<213> ORGANISM: Artificial sequence
<220> FEATURE:
<223> OTHER INFORMATION: synthetic
<220> FEATURE:
<221> NAME/KEY: domain
<222> LOCATION: (1)..(35)
<223> OTHER INFORMATION: Ckappa

<400> SEQUENCE: 43

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Tyr Gly Pro
                20                  25                  30

Gly Gly Pro
        35
```